(12) United States Patent
Niitsu et al.

(10) Patent No.: US 11,084,779 B2
(45) Date of Patent: *Aug. 10, 2021

(54) CATIONIC LIPIDS FOR THERAPEUTIC AGENT DELIVERY FORMULATIONS

(71) Applicant: Nitto Denko Corporation, Osaka (JP)

(72) Inventors: Yoshiro Niitsu, Hokkaido (JP); Victor Knopov, Oceanside, CA (US); Joseph E. Payne, Oceanside, CA (US); Zheng Hou, San Diego, CA (US); John A. Gaudette, Poway, CA (US); Violetta Akopian, Oceanside, CA (US); Richard P. Witte, San Diego, CA (US); Mohammad Ahmadian, Carlsbad, CA (US); Loren A. Perelman, San Diego, CA (US); Yasunobu Tanaka, Osaka (JP); Priya Karmali, San Diego, CA (US); Sridhar C. Nagarajan, San Diego, CA (US)

(73) Assignee: Nitto Denko Corporation, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/700,304

(22) Filed: Dec. 2, 2019

(65) Prior Publication Data

US 2020/0199064 A1 Jun. 25, 2020

Related U.S. Application Data

(60) Continuation of application No. 15/919,098, filed on Mar. 12, 2018, now Pat. No. 10,532,975, which is a continuation of application No. 15/005,569, filed on Jan. 25, 2016, now Pat. No. 9,963,424, which is a continuation of application No. 14/256,306, filed on
(Continued)

(51) Int. Cl.

| | |
|---|---|
| A61K 31/713 | (2006.01) |
| C07C 237/08 | (2006.01) |
| A61K 47/54 | (2017.01) |
| A61K 9/00 | (2006.01) |
| A61K 9/10 | (2006.01) |
| A61K 9/127 | (2006.01) |
| A61K 47/18 | (2017.01) |
| C12N 15/113 | (2010.01) |
| C07C 323/60 | (2006.01) |
| C07C 333/04 | (2006.01) |

(52) U.S. Cl.
CPC .......... *C07C 237/08* (2013.01); *A61K 9/0019* (2013.01); *A61K 9/10* (2013.01); *A61K 9/1271* (2013.01); *A61K 31/713* (2013.01); *A61K 47/186* (2013.01); *A61K 47/543* (2017.08); *C07C 323/60* (2013.01); *C07C 333/04* (2013.01); *C12N 15/113* (2013.01)

(58) Field of Classification Search
None
See application file for complete search history.

(56) References Cited

U.S. PATENT DOCUMENTS

| 4,501,729 A | 2/1985 | Boucher et al. |
|---|---|---|
| 5,138,045 A | 8/1992 | Cook et al. |

(Continued)

FOREIGN PATENT DOCUMENTS

| CN | 101855237 A | 10/2010 |
|---|---|---|
| DE | 19641672 A1 | 4/1998 |

(Continued)

OTHER PUBLICATIONS

Australia Patent Application No. 2012267467; Office Action; dated Jul. 11, 2016; 3 pages.

(Continued)

*Primary Examiner* — Samantha L Shterengarts
(74) *Attorney, Agent, or Firm* — Knobbe, Martens, Olson & Bear, LLP

(57) ABSTRACT

Here described is a composition comprising a compound of formula I:

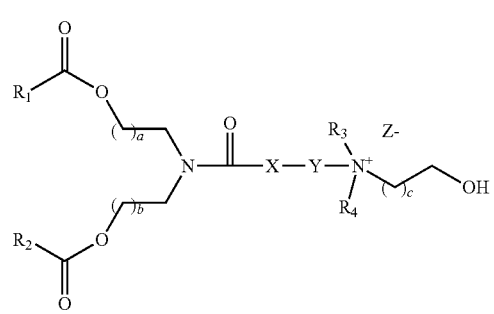

wherein $R_1$ and $R_2$ is independently selected from a group consisting of $C_{10}$ to $C_{18}$ alkyl, $C_{12}$ to $C_{18}$ alkenyl, and oleoyl group; $R_3$ and $R_4$ are independently selected from a group consisting of $C_1$ to $C_6$ alkyl, and $C_2$ to $C_6$ alkanol; X is selected from a group consisting of —$CH_2$—, —S—, and —O— or absent; Y is selected from —$(CH_2)_n$—, —$S(CH_2)_n$—, —$O(CH_2)_n$—, thiophene, —$SO_2(CH_2)_n$—, and ester; n=1-4; a=1-4; b=1-4; c=1-4; and $Z^-$ is a counterion.

40 Claims, 6 Drawing Sheets

Specification includes a Sequence Listing.

Related U.S. Application Data

Apr. 18, 2014, now Pat. No. 9,242,001, which is a division of application No. 13/492,650, filed on Jun. 8, 2012, now Pat. No. 9,011,903.

(60) Provisional application No. 61/494,710, filed on Jun. 8, 2011.

(56) References Cited

U.S. PATENT DOCUMENTS

| | | | |
|---|---|---|---|
| 5,214,136 | A | 5/1993 | Lin et al. |
| 6,153,737 | A | 11/2000 | Manoharan et al. |
| 6,180,613 | B1 | 1/2001 | Kaplitt et al. |
| 6,235,886 | B1 | 5/2001 | Manoharan et al. |
| 6,270,806 | B1 | 8/2001 | Liversidge et al. |
| 6,335,434 | B1 | 1/2002 | Guzaev et al. |
| 6,372,714 | B1 | 4/2002 | Tanaka et al. |
| 6,468,551 | B1 | 10/2002 | Diec et al. |
| 6,528,631 | B1 | 3/2003 | Cook et al. |
| 6,534,484 | B1 | 3/2003 | Wheeler et al. |
| 6,565,885 | B1 | 5/2003 | Tarara et al. |
| 6,582,728 | B1 | 6/2003 | Platz et al. |
| 6,586,410 | B1 | 7/2003 | Wheeler et al. |
| 6,586,524 | B2 | 7/2003 | Sagara |
| 6,592,904 | B2 | 7/2003 | Platz et al. |
| 6,613,735 | B2 | 9/2003 | Tanaka et al. |
| 6,635,683 | B1 | 10/2003 | Taira et al. |
| 6,815,432 | B2 | 11/2004 | Wheeler et al. |
| 6,858,224 | B2 | 2/2005 | Wheeler et al. |
| 6,858,225 | B2 | 2/2005 | Semple et al. |
| 7,799,565 | B2 | 9/2010 | MacLachlan et al. |
| 7,807,815 | B2 | 10/2010 | MacLachlan et al. |
| 7,833,992 | B2 | 11/2010 | Vargeese et al. |
| 7,901,708 | B2 | 3/2011 | MacLachlan et al. |
| 7,915,399 | B2 | 3/2011 | MacLachlan et al. |
| 7,982,027 | B2 | 7/2011 | MacLachlan et al. |
| 8,058,069 | B2 | 11/2011 | Yaworski et al. |
| 8,741,867 | B2 | 6/2014 | Niitsu et al. |
| 9,011,903 | B2 | 4/2015 | Niitsu et al. |
| 9,242,001 | B2 | 1/2016 | Niitsu et al. |
| 9,393,315 | B2 | 7/2016 | Niitsu et al. |
| 9,456,984 | B2 | 10/2016 | Niitsu et al. |
| 9,944,671 | B2 | 4/2018 | Hinkle et al. |
| 9,963,424 | B2 | 5/2018 | Niitsu et al. |
| 2003/0161791 | A1 | 8/2003 | Bentley et al. |
| 2004/0037780 | A1 | 2/2004 | Parsons et al. |
| 2007/0161596 | A1 | 7/2007 | McSwiggen et al. |
| 2008/0193512 | A1 | 8/2008 | Niitsu et al. |
| 2009/0105179 | A1 | 4/2009 | Yu et al. |
| 2011/0200527 | A1 | 8/2011 | Xu et al. |
| 2013/0171127 | A1 | 7/2013 | Niitsu et al. |
| 2013/0171240 | A1 | 7/2013 | Niitsu et al. |
| 2013/0210744 | A1 | 8/2013 | Niitsu et al. |
| 2017/0081663 | A1 | 3/2017 | Niitsu et al. |

FOREIGN PATENT DOCUMENTS

| | | | |
|---|---|---|---|
| EP | 1842557 | A1 | 10/2007 |
| JP | 61-089286 | A | 5/1986 |
| JP | 61-136584 | A | 6/1986 |
| JP | 2001-501639 | A | 2/2001 |
| JP | 2005-507934 | A | 3/2005 |
| JP | 2006-254877 | A | 9/2006 |
| JP | 2006-522140 | A | 9/2006 |
| JP | 2010-539245 | A | 12/2010 |
| JP | 2016-153477 | A | 8/2016 |
| RU | 2 203 268 | C2 | 4/2003 |
| TW | 201000134 | | 1/2010 |
| TW | I569814 | B | 2/2017 |
| WO | WO 96/30036 | | 10/1996 |
| WO | WO 1998/013025 | A1 | 4/1998 |
| WO | WO 2003/037385 | A1 | 5/2003 |
| WO | WO 2004/013280 | A2 | 2/2004 |
| WO | WO 2004/089311 | A2 | 10/2004 |
| WO | WO 2008/132723 | A2 | 11/2008 |
| WO | WO 2009/036368 | A2 | 3/2009 |
| WO | WO 2010/014117 | A1 | 2/2010 |
| WO | WO 2010/029760 | A1 | 3/2010 |
| WO | WO 2010/061880 | A1 | 6/2010 |
| WO | WO 2012/170957 | A2 | 12/2012 |

OTHER PUBLICATIONS

European Patent Application No. 15181729.3; Office Action—Article 94(3); dated Nov. 7, 2016; 6 pages.

Russia Patent Application No. 2013158456/04; Office Action; dated Apr. 22, 2016; 10 pages.

Abu-Lila et al., "Oxaliplatin encapsulated in PEG-coated cationic liposomes induces significant tumor growth suppression via a dual-targeting approach in a murine solid tumor model," J. Controlled Release, Jul. 2009, 137(1), 8-14.

Abu-Lila et al., "Oxaliplatin targeting to angiogenic vessels by PEGylated cationic liposomes suppresses the angiogenesis in a dorsal air sac mouse model," J. Controlled Release, Feb. 2009, 134(1), 18-25.

Choi et al., "Effect of Poly(ethylene glycol) Grafting on Polyethylenimine as a Gene Transfer Vector in vitro," Bull. Korean Chem. Soc., Jan. 2001, 22(1), 46-52.

Diebold et al., "Mannose Polyethylenimine Conjugates for Targeted DNA Delivery into Dendritic Cells," J. Biol. Chem., Jul. 1999, 274(27), 19087-19094.

Epa et al., "Downregulation of the p75 Neurotrophin Receptor in Tissue Culture and In Vivo, Using .beta.-Cyclodextrin-Adamantane-Oligonucleotide Conjugates," Antisense Nuc. Acid Drug Dev., Dec. 2000, 10(6), 469-478.

Erbacher et al., "Transfection and physical properties of various saccharide, poly(ethylene glycol), and antibody-derivatized polyethylenimines (PEI)," J. Gene Med., May-Jun. 1999, 1(3), 210-222.

Feril Jr., et al., "Ultrasound enhances liposome-mediated gene transfection," Ultrasonics Sonochemistry, Aug. 2005, 12(6), 489-493.

Fingl et al., "The Pharmacological Basis of Therapeutics," 1975, Chapter 1, p. 1.

Godbey et al., "Poly(ethylenimine) and its role in gene delivery," J. Controlled Release, Aug. 1999, 60(2-3), 149-160.

Godbey et al., "Tracking the intracellular path of poly(ethylenimine)/DNA complexes for gene delivery," PNAS, Apr. 1999, 96(9), 5177-5181.

Hada et al., "The first synthesis of PEG-carotenoid conjugates," Chemical Abstracts Services, XP002690323, Apr. 2011, 8 pages.

Hao et al., "Phorbol Ester-Potentiated Liposomal Transfection to Monocytic PLB-985 Cells," J. Biochem., Dec. 2000, 128(6), 989-998.

International Patent Application No. PCT/US2012/041753; International Search Report dated Jan. 30, 2013, 8 pages.

Ishiwata et al., "Characteristics and biodistribution of cationic liposomes and their DNA complexes," J. of Controlled Release, Oct. 2000, 69(1), 139-148.

Justus et al., "Synthesis, Liposomal Preparation, and in Vitro Toxicity of Two Novel Dodecaborate Cluster Lipids for Boron Neutron Capture Therapy," Bioconjugate Chem., Jul.-Aug. 2007, 18(4), 1287-1293.

Kikuchi et al., "Development of novel cationic liposomes for efficient gene transfer into peritoneal disseminated tumor," Hum. Gene Ther., Apr. 1999, 10(6), 947-955.

Kusumoto et al., "Gene transfer effects on various cationic amphiphiles in CHO cells," Cytotechnology, Jun. 2006, 51(2), 57-66.

Li et al., "Synthesis of polyethylene glycol (PEG) derivatives and PEGylated-peptide biopolymer conjugates," Biomacromolecules, Jul.-Aug. 2003, 4(4), 1055-1067.

Moon et al., "Regulation of adipocyte differentiation by PEGylated all-trans retinoic acid: reduced cytotoxicity and attenuated lipid accumulation," J. Nutr. Biochemistry, May 2007, 18(5), 322-331.

Nakashima et al., "Design of a Lipid Bilayer Electrical Device. Strong Chemical Structure Dependence and Molecular Mechanisms

(56) References Cited

OTHER PUBLICATIONS on the Phase Transition-Dependent Electrical Impedance Responses of the Device in Air," J. Phys. Chem. B, Jan. 1997, 101(2), 215-220.
Nakashima et al., "Design of a Lipid Bilayer Electrical Device. Strong Chemical Structure Dependence and Molecular Mechanisms on the Phase Transition-Dependent Electrical Impedance Responses of the Device in Air," J. Phys. Chem. B, May 1998, 102(22), 4440 (Additions/Corrections).
Ogris et al., "DNA/polyethylenimine transfection particles: Influence of ligands, polymer size, and PEGylation on internalization and gene expression," AAPS PharmSci, Sep. 2001, 3(3), 43-53.
Radwan et al., "Cationic liposome-mediated gene delivery: Biophysical study and mechanism of internalization," Archives of Biochem. and Biophysics, Feb. 2003, 410(2), 246-253.
Schreiber et al., "Disperse multiphase systems linked by covalent bonds into a network," Chemical Abstracts Services, XP002690325, 1999, 1 page.
Serikawa et al., "A new cationic liposome for efficient gene delivery with serum into cultured human cells: a quantitative analysis using two independent fluorescent probes," Biochimica et Biophysica Acta, Aug. 2000, 1467(2), 419-430.
Serikawa et al., "Enhancement of Gene Expression Efficiency Using Cationic Liposomes on Ovarian Cancer Cells," Drug Deliv., Nov. 2008, 15(8), 523-529.
Simantov et al., "Dopamine-Induced Apoptosis in Human Neuronal Cells: Inhibition by Nucleic Acids Antisense to the Dopamine Transporter," Neuroscience, Sep. 1996, 74(1), 39-50.
Solodin et al., "Synthesis of Novel Cationic Lipids with a Guanidine Group. Cationic Lipids , 3.sup.1," Synlett, Jul. 1996, 7, 617-618.
Sommer et al., "The Spread and Uptake Pattern of Intracerebrally Administered Oligonucleotides in Nerve and Glial Cell Populations of the Rat Brain," Antisense Nuc. Acid Drug Dev., Apr. 1998, 8(2), 75-85.
Tachibana et al., "An assessment of relative transcriptional availability from nonviral vectors," Int. J. Pharm., Feb. 2004, 270(1-2), 315-321.
Tachibana et al., "Effect of Cationic Liposomes in an in Vitro Transcription and Translation System," Biol. Pharm. Bull., Apr. 2002, 25(4), 529-531.
Tagami et al., "Effect of siRNA in PEG-coated siRNA-lipoplex on anti-PEG IgM production," J. Controlled Release, Aug. 2009, 137(3), 234-240.
Thomas et al., "Enhancing polyethylenimine's delivery of plasmid DNA into mammalian cells," PNAS, Nov. 2002, 99(23), 14640-14645.
Umebayashi et al., "Inhibitory effects of three-component hybrid liposomes containing cationic lipids without drugs on the growth of human renal tumor cells in vitro," Biol. Pharm. Bull., Sep. 2008, 31(9), 1816-1817.
China Patent Application No. 201280027912.7; Office Action; dated Nov. 15, 2014; 11 pages.
Sato et al.; Resolution of liver cirrhosis using A-coupled liposomes to deliver siRNA against a collagen-specific chaperone; Nature Biotechnology; Apr. 2008; 26(4); p. 431-442.
King et al.; "Determination of cobalt, copper, mercury, and nickel as bis(2-hydroxyethyl)dithiocarbamate complexes by high-performance liquid chromatography"; Analytical Chemistry; 1987; 59(5); p. 703-708.
Taiwan Patent Application No. 101120615; Office Action; dated Feb. 9, 2017; 7 pages.
Pedersen et al.; "Liposomal Formulation of Retinoids Designed for Enzyme Triggered Release"; Journal of Medicinal Chemistry; vol. 53 No. 9; 2010; p. 3782-3792.
Japan Patent Application No. 2016-006249; Office Action—Reason for Refusal; dated Nov. 17, 2016; 13 pages, (contains English Translation).
Chiu et al.; "siRNA function in RNAi: A chemical modification analysis"; RNA; vol. 9 No. 9; 2003; p. 1034-1048.
TW Patent Application No. 105140746; Office Action; dated Dec. 4, 2017; 9 pages.
Bentley et al.; "Water-soluble polymer conjugates of retinoic acid"; Caesar Accession No. 1091; CAPLUS 2003:356296; Shearwater Corporation; accessed Jan. 15, 2013; 4 pages.
Horimoto et al.; "Liquid Crystal Compositions"; CAPLUS Accession No. 1987:11469; 1 page.
Horimoto et al.; "Liquid Crystal Compositions"; CAPLUS Accession No. 1987:59428; 2 pages.
Diec et al.; "Cosmetic or Dermatological Crosslinked Microemulsions"; CAPLUS Accession No. 1998:239092; 2 pages.
Schreiber et al.; "Crosslinked Structures with Double Lipid Membranes or Based on Peptides"; CAPLUS Accession No. 1998:208404; 2 pages.
Bentley et al.; "Water-Soluble Polymer Conjugates of Retinoic Acid"; CAPLUS Accession No. 2003-356296; 4 pages.
Hada et al.; "The first synthesis of PEG-carotenoid conjugates"; Tetrahedron Letters; vol. 52 No. 25; 2011; p. 3195-3197.
Canada Patent Application No. 2836925; Office Action; dated Feb. 26, 2018; 4 pages.
Korean Patent Application No. 10-2014-7000572; Notice of Preliminary Rejection; dated Jul. 11, 2018; 17 pages.
Australian Patent Application No. 2017203075; Examination Report; dated Jun. 19, 2018; 4 pages.
Japan Patent Application No. 2017-203199; Reasons for Refusal; dated Oct. 19, 2018; 8 pages.
China Patent Application No. 201710081577.3; Office Action; dated Aug. 28, 2018; 13 pages.
Canada Patent Application No. 2,837,101; Office Action; dated Apr. 11, 2018; 5 pages.
Korean Patent Application No. 10-2014-7000573; Notice of Preliminary Rejection; dated Feb. 15, 2019; 11 pages.
Korean Patent Application No. 10-2018-7034794; Notice of Preliminary Rejection; dated Feb. 15, 2019; 12 pages.
Korean Patent Application No. 10-2018-7034790; Notice of Preliminary Rejection; dated Feb. 15, 2019; 15 pages.
China Patent Application No. 201710081577.3; Second Office Action; dated May 7, 2019; 7 pages.
Canada Patent Application No. 2,837,101; Office Action; dated Aug. 27, 2019; 4 pages.
Li Xianzhen et al.; Biological Chemistry; Huazhong University of Science and Technology Press; Jun. 2008; p. 52-55.
Shen Renquan et al.; Biochemistry Course; Higher Education Press; Dec. 1993; p. 38-44.
China Patent Application No. 201710081577.3; Third Office Action; dated Oct. 8, 2019; 9 pages.
Taiwan Patent Application No. 105140746; Office Action; dated Jun. 11, 2020; 4 pages.
Cong, Y., et al., Superior Medical Reference Laboratory Medicine, Military Medical Press, Jan. 31, 2007, vol. 1, p. 16.
Hu, J., et al., Handbook of Materia Medica (4th Edition), Jindun Press, Mar. 31, 2009, p. 345.
Lin, P., et al., Biochemistry, People's Military Medical Press, Jun. 30, 2006, p. 135.
Office Action issued in the corresponding Chinese Patent Application No. 201710081858.9 dated Jun. 28, 2020.
Office Action and Search Report dated Jan. 13, 2021 for Russian Patent Application No. 2017135548/04(061959).

CATIONIC LIPIDS FOR THERAPEUTIC AGENT DELIVERY FORMULATIONS

CROSS REFERENCE TO RELATED APPLICATION

This application is a continuation of U.S. patent application Ser. No. 15/919,098, filed Mar. 12, 2018, which is a continuation of U.S. patent application Ser. No. 15/005,569, filed Jan. 25, 2016, now U.S. Pat. No. 9,963,424, issued May 8, 2018, which is a continuation of U.S. patent application Ser. No. 14/256,306, filed Apr. 18, 2014, now U.S. Pat. No. 9,242,001, issued Jan. 26, 2016, which is a divisional of U.S. patent application Ser. No. 13/492,650, filed Jun. 8, 2012, now U.S. Pat. No. 9,011,903, issued Apr. 21, 2015, which claims the benefit of U.S. Provisional Application No. 61/494,710, filed Jun. 8, 2011, which are herein incorporated by reference in their entireties.

SEQUENCE LISTING

The instant application contains a Sequence Listing which has been submitted electronically in ASCII format and is hereby incorporated by reference in its entirety. Said ASCII copy, created on Dec. 5, 2019, is named 101025_000074_SL.txt, which is 4,699 bytes in size.

TECHNICAL FIELD

The description herein is directed to a composition comprising cationic lipids for enhancing the delivery of therapeutic agents.

BACKGROUND

A number of techniques are available for delivering a therapeutic agent such as siRNA into a cell, including the use of viral transfection systems and non-viral transfection systems. Non-viral transfection systems can include, for example, polymers, lipids, liposomes, micelles, dendrimers, and nanomaterials. Examples of polymers that have previously been studied for cell transfection include cationic polymers such as poly(L-lysine), polyethyleneimine, chitosan, and poly(2-dimethylamino)ethyl methacrylate.

Each type of system has its respective advantages and drawbacks. For example, viral systems can yield high transfection efficiency, but may not be as safe as some non-viral systems. In addition, viral systems can be complicated and/or expensive to prepare. Non-viral transfection systems, such as cationic polymers, have been reported to transfer plasmid DNA into cells. However, some drawbacks to the use of cationic polymers include their toxicity to cells and/or their lack of stability.

As such, there is a pressing need for new compounds, compositions, and methods of using cationic components to improve delivery of therapeutic drugs, including nucleic acids, to cells, tissues and organisms.

SUMMARY

One aspect of the description herein is a composition comprising a compound of formula I

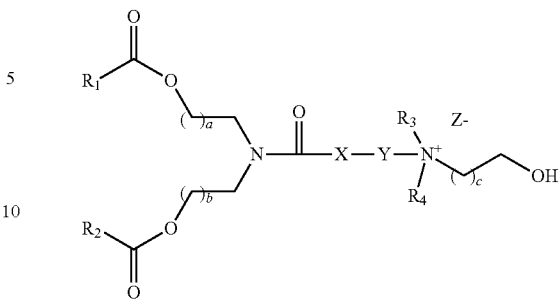

wherein $R_1$ and $R_2$ are independently selected from a group consisting of $C_{10}$ to $C_{18}$ alkyl, $C_{12}$ to $C_{18}$ alkenyl, and oleoyl group; $R_3$ and $R_4$ are independently selected from a group consisting of $C_1$ to $C_6$ alkyl, and $C_2$ to $C_6$ alkanol; X is selected from a group consisting of —$CH_2$—, —S—, and —O— or absent; Y is selected from —$(CH_2)_n$—, —$S(CH_2)_n$—, —$O(CH_2)_n$—, thiophene, —$SO_2(CH_2)_n$—, and ester; n=1-4; a=1-4; b=1-4; c=1-4; and $Z^-$ is a counterion, or an enantiomer, stereoisomer, or diastereoisomer thereof.

Preferably, $R_1$ and $R_2$ are independently selected from $C_{10}$ to $C_{18}$ alkyl, and $C_{12}$ to $C_{18}$ alkenyl. Preferably, $R_3$ and $R_4$ are each independently $C_1$-$C_3$ alkyl, most preferably methyl or at least one of $R_3$ and $R_4$ is —$CH_2CH_2OH$. Preferably, a, b, and c are 1.

The composition preferably further comprises a drug, more preferably one that directly or indirectly inhibits physicochemical actions of stellate cells involved in promotion of fibrosis, e.g., wherein the drug inhibits actions of stellate cells selected from the group consisting of transforming growth factor-beta (TGFβ) inhibitors, matrix metalloproteinase (MMP) production promotors, hepatocyte growth factors (HGF), angiotensin, tissue inhibitor of metalloproteinase (TIMP) production inhibitors, platelet-derived growth factor (PDGF), sodium channel inhibitor, apoptosis inhibitors, adiponectin, Rho kinase inhibitor, and heat shock protein 47 (HSP47). The apoptosis inhibitor preferably is herbal compound 861 (Cpd 861) or gliotoxin. Preferably, the drug controls the metabolism of an extracellular matrix, e.g., by targeting an extracellular matrix constituent molecule, including collagen.

The drug preferably comprises a nucleic acid, particularly nucleic acid selected from the group consisting of oligonucleotides, siRNA, and DNA or RNA expression vectors. The nucleic acid is preferably formulated or complexed with polyethyleneimine (PEI) or PEI derivatives, particularly PEI derivatives selected from the group consisting of galactose PEI, cholesterol PEI, antibody derivatized PEI, and polyethylene glycol-PEI derivatives.

The composition preferably is selected from the group consisting of a polymer micelle, a liposome, an emulsion, a microsphere, and a nanosphere, most preferably a liposome comprising one or more lipid bilayers, wherein the lipid bilayers comprise the cationic lipid of formula I. The cationic lipid of formula I preferably is at a concentration of 5 mol % to 50 mol % of the lipid bilayer.

The preferred cationic lipid of the composition is selected from the group consisting of HEDX-12, HEDC, Pr-HEDC, HE-Et-DC, HE-Pr-DC, HES104, HE-DODC-DLin, HE2-DODC, HE-DODC, HE-Et-DODC, HE-Pr-DODC, HES104DO, and HETU104DO

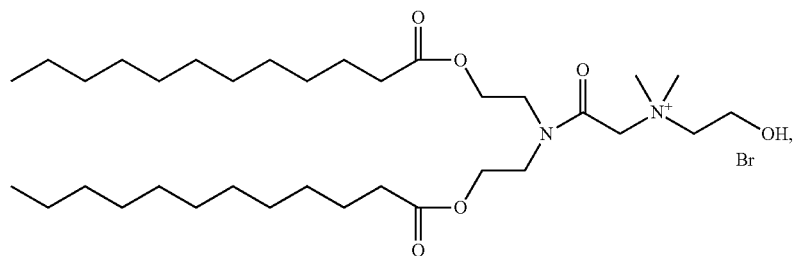
HEDC-12
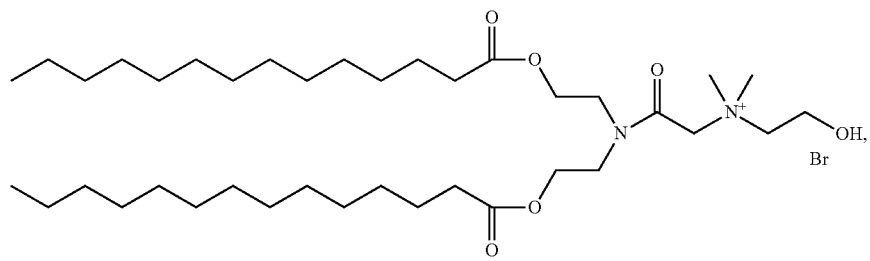
HEDC
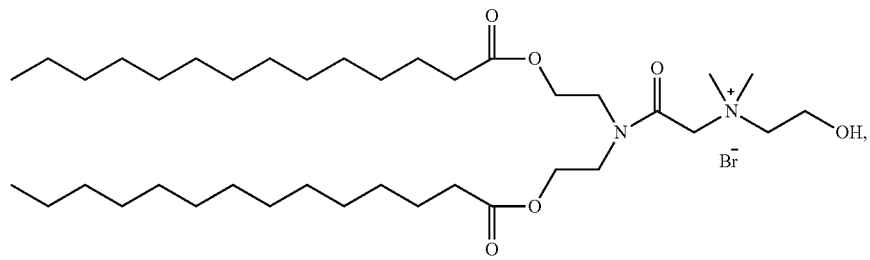
Pr-HEDC
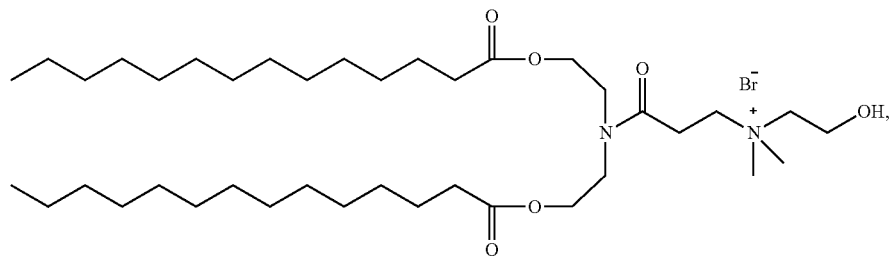
HE-Et-DC
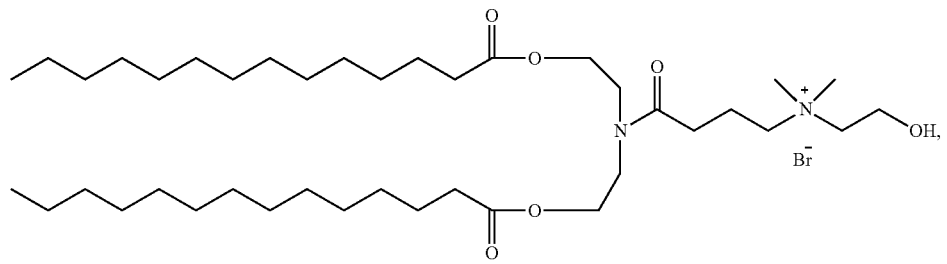
HE-Pr-DC
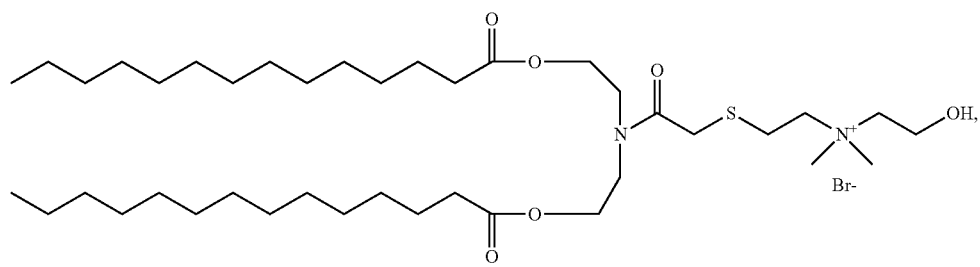
HES104

-continued
HE-DODC-DLin
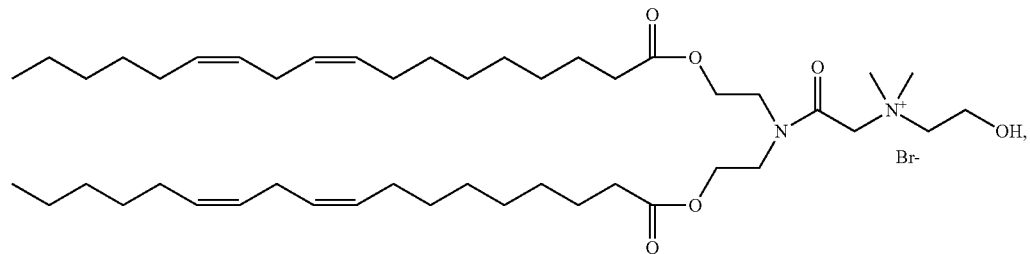
HE2-DODC
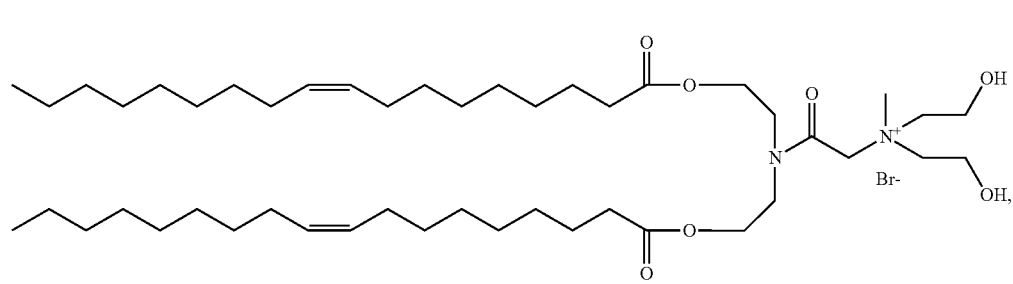
HE-DODC
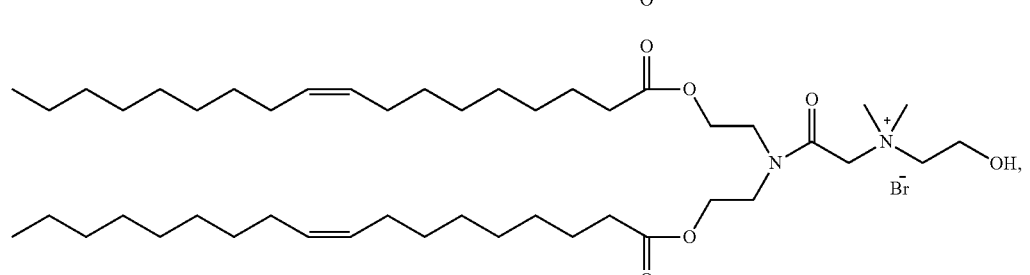
HE-Et-DODC
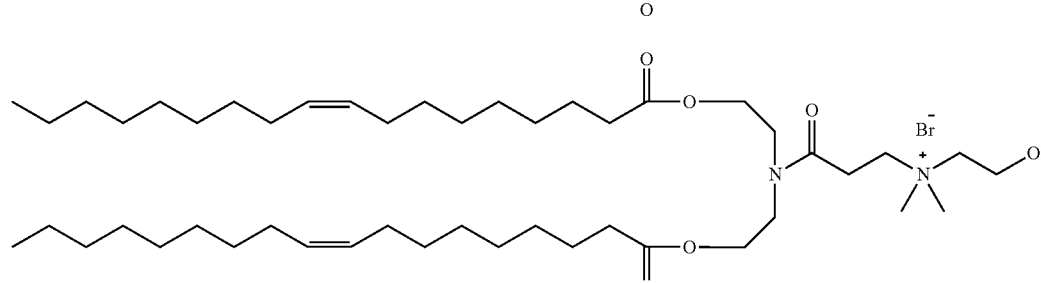
HE-Pr-DODC
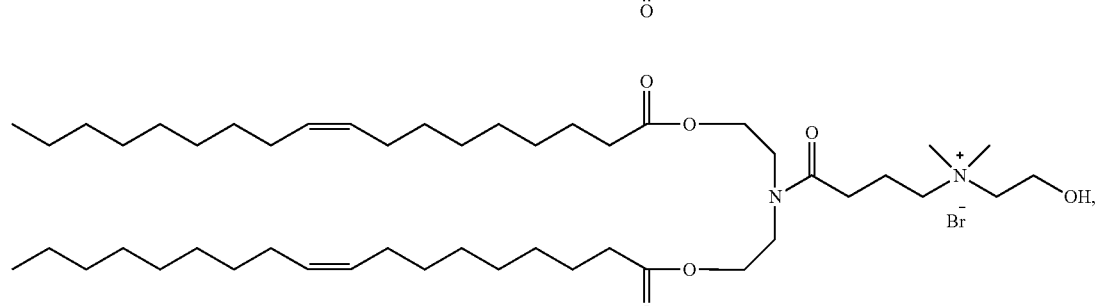
HES104DO
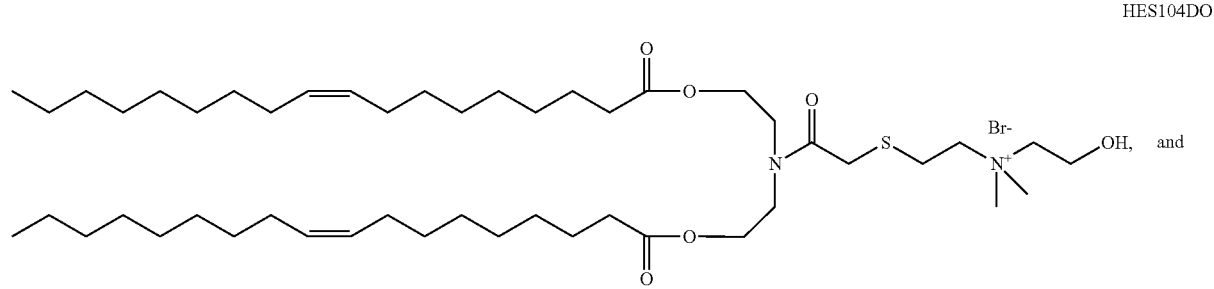
and

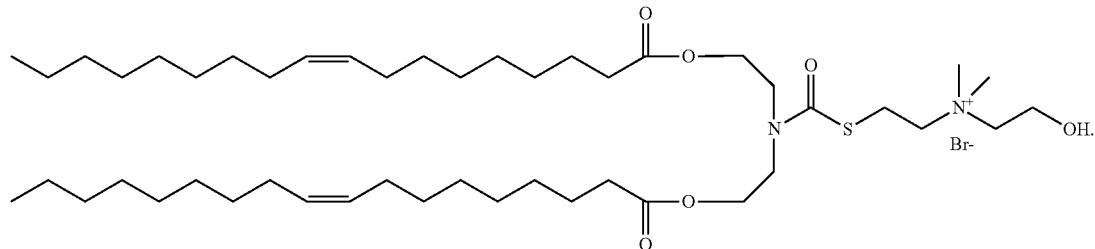

HETU104DO

The composition alternatively further comprises an ionizable cationic lipid, e.g., S104

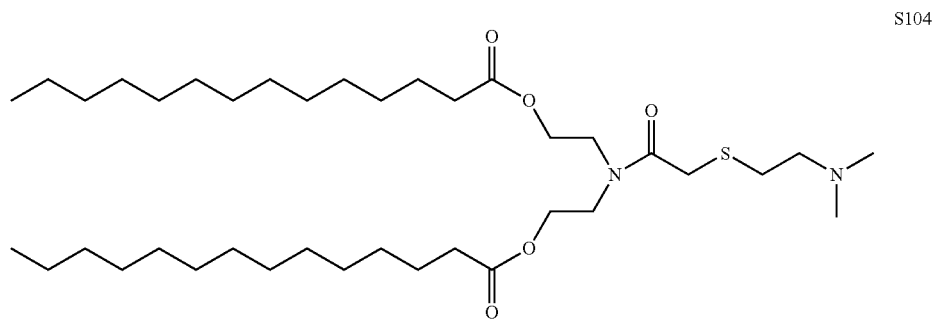 [SMILES: CCCCCCCCCCCCCC(=O)OCCN(CCOC(=O)CCCCCCCCCCCCC)C(=O)CSCCN(C)C]

S104

The ionizable cationic lipid is preferably at a concentration of 5 to 45 mol % of the lipid bilayer.

The composition alternatively further comprises a non-cationic lipid, preferably selected from the group consisting of lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Alternatively, the non-cationic lipid is a sterol selected from the group consisting of cholesterol, cholestanol, cholestanone, cholestenone, coprostanol, cholesteryl-2'-hydroxyethyl ether, cholesteryl-4'-hydroxybutyl ether, and mixtures thereof.

Another aspect of the description herein is a pharmaceutical formulation comprising the composition comprising a compound of formula I and a pharmaceutically acceptable excipient. One possible pharmaceutically acceptable excipient is a preservative selected from the group consisting of sodium benzoate, ascorbic acid and esters of p-hydroxybenzoic acid. Another possible pharmaceutically acceptable excipient is selected from, alcohols, esters, sulfated aliphatic alcohols, sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose; coconut oil, olive oil, sesame oil, peanut oil, soya, cellulose acetate phthalate, methyl acetate-methacrylate copolymer, and ester phthalates.

One pharmaceutically formulation is suitable for aerosolized administration to the lung, preferably further comprising excipients selected from the group consisting of dichlorodifluoromethane, trichlorofluoromethane, dichlorotetrafluoroethane, ethanol, emulsifiers, oleic acid, or sorbitan trioleate, anti-oxidants, flavoring agents, and mixtures thereof.

Another pharmaceutical formulation is suitable for parenteral administration, preferably further comprising excipients selected from the group consisting of water, saline, sodium carboxymethyl cellulose, sorbitol, dextran, dextrose, mannitol, lactose, lecithin, albumin, sodium glutamate, cysteine hydrochloride, Hanks's solution, Ringer's solution, and physiological saline buffer.

Another pharmaceutical formulation is suitable for administration to the central nervous system (CNS) or peripheral nervous system (PNS), preferably suitable for intrathecal and intracerebroventricular administration, implantation of catheters and pumps, direct injection or perfusion at the site of injury or lesion, injection into the brain arterial system, or by chemical or osmotic opening of the blood-brain barrier.

Another pharmaceutical formulation is suitable for intramuscular injection, preferably further comprising excipients selected from polymeric or hydrophobic materials, and ion exchange resins.

Another pharmaceutical formulation is suitable for administration via injection, subcutaneously, intraperitoneally, intravenously, intramuscularly, intradermally, intraorbitally, intracapsularly, intraspinally, or intrasternally, or infusion pump delivery.

Another pharmaceutical formulation is suitable for administration locally by injection directly in the renal or cardiac area by depot implantation.

DETAILED DESCRIPTION OF ILLUSTRATIVE EMBODIMENTS

Figure 1:
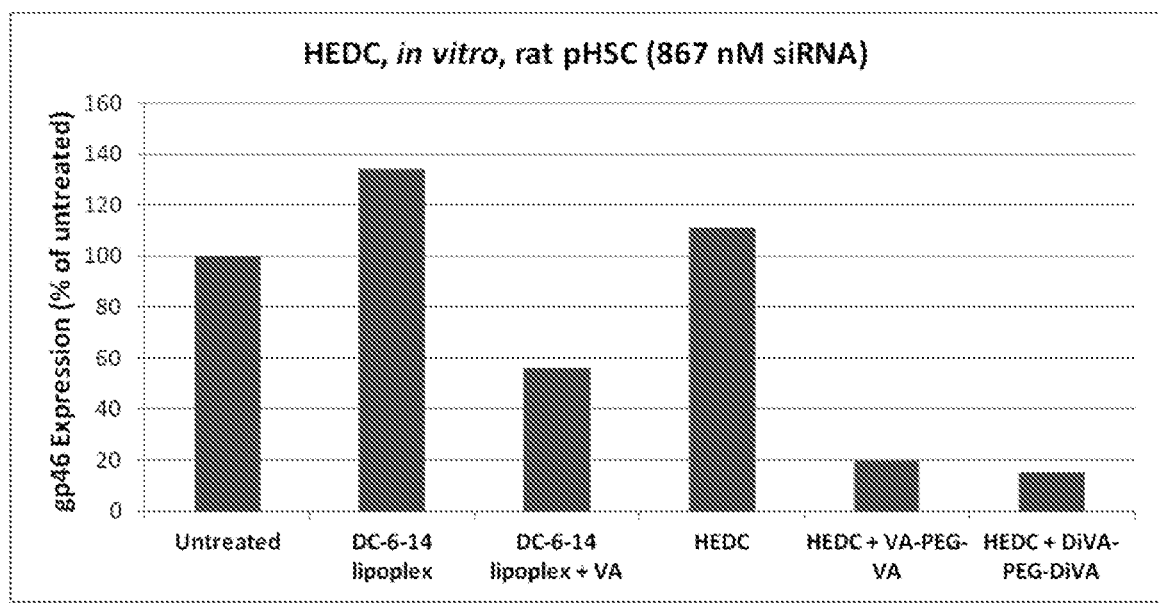
FIG. 1 depicts knockdown efficacy of certain embodiments of the description. This includes HEDC liposomes compared to DC-6-14 lipoplex controls.

Within the scope of the description are compounds of formula I

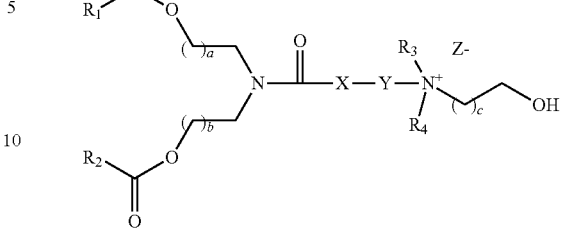

wherein $R_1$ and $R_2$ is independently selected from a group consisting of $C_{10}$ to $C_{18}$ alkyl, $C_{12}$ to $C_{18}$ alkenyl, and oleoyl group; $R_3$ and $R_4$ are independently selected from a group consisting of $C_1$ to $C_6$ alkyl, and $C_2$ to $C_6$ alkanol; X is selected from a group consisting of —$CH_2$—, —S—, and —O— or absent; Y is selected from —$(CH_2)_n$—, —$S(CH_2)_n$—, —$O(CH_2)_n$—, thiophene, —$SO_2(CH_2)_n$—, and ester; n=1-4; a=1-4; b=1-4; c=1-4; and $Z^-$ is a counterion.

Compounds of the description herein are also referred to herein as being within the class of compounds known as "cationic lipids." Cationic lipids are compounds that include at least one lipid moiety and a positively charged nitrogen associated with a counterion. "Lipids" are understood in the art to be comprised of a hydrophobic alkyl or alkenyl moiety and a carboxylic acid or ester moiety.

It has heretofore been discovered that the amino-alkyl-hydroxyl (—N-alkyl-OH) moiety of the compounds of formula I imparts properties to the formulations of the description herein not previously seen with other cationic lipids previously reported. Formulations of the description herein include compounds of formula I result in superior reduction in protein expression, as compared to formulations that do not include compounds of formula I. Particularly surprising is the ability of formulations of the description herein that include compounds of formula I to reduce the expression of heat shock protein 47 (HSP47), SERPHINH1.

Preferred compounds of the description herein include those wherein $R_1$ and $R_2$ are each independently $C_{10}$-$C_{30}$ alkyl. In more preferred embodiments, $R_1$ and $R_2$ are each independently $C_{10}$-$C_{20}$ alkyl. In even more preferred embodiments, $R_1$ and $R_2$ are each independently $C_{12}$-$C_{18}$ alkyl. Particularly preferred embodiments include those wherein $R_1$ and $R_2$ are each independently $C_{13}$-$C_{17}$ alkyl. Most preferred are those compounds wherein $R_1$ and $R_2$ are each $C_{13}$ alkyl.

In other embodiments, $R_1$ and $R_2$ are each independently $C_{10}$-$C_{30}$ alkenyl. In more preferred embodiments, $R_1$ and $R_2$ are each independently $C_{10}$-$C_{20}$ alkenyl. In still other embodiments, $R_1$ and $R_2$ are each independently $C_{12}$-$C_{18}$ alkenyl. In yet other embodiments, $R_1$ and $R_2$ are each independently $C_{13}$-$C_{17}$ alkenyl. Most preferred compounds of the description herein include those wherein $R_1$ and $R_2$ are each $C_{17}$ alkenyl.

Also for compounds of formula I, $R_3$ and $R_4$ are independently selected from a group consisting of $C_1$ to $C_6$ alkyl. In preferred embodiments, $R_3$ and $R_4$ are each independently $C_1$-$C_3$ alkyl. Most preferably, $R_3$ and $R_4$ are each methyl. In other embodiments, at least one of $R_3$ and $R_4$ are —$CH_2CH_2OH$.

Most preferred are those compounds of formula I, wherein a, b, and c are all 1.

Z can be any nitrogen counterion, as that term is readily understood in the art. Preferred nitrogen counterions include halogens, with chloride and bromide being particularly preferred and mesylate (SO$_3$CH$_3$$^-$). In contrast to other cationic lipids previously described wherein the effect of the cationic lipid depends on the counterion, the efficacy of compounds of formula I, surprisingly, do not appear to be related to the counterion selected.

Exemplary compounds of formula I include the following compounds.

HEDC-12

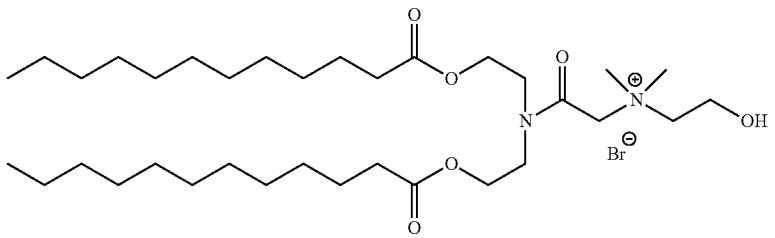

HEDC

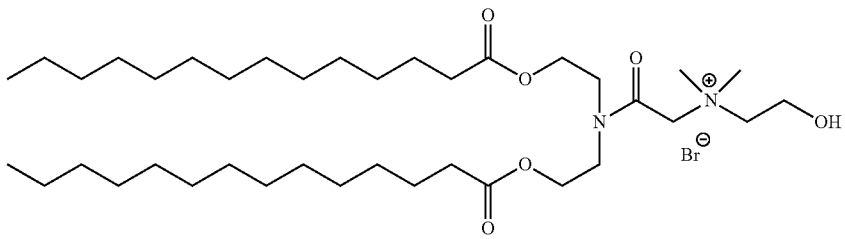

Pr-HEDC

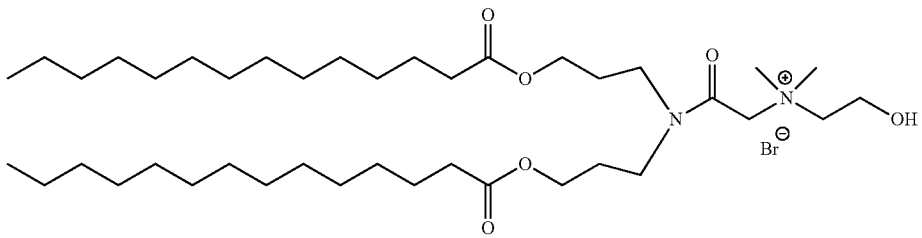

HE-Et-DC

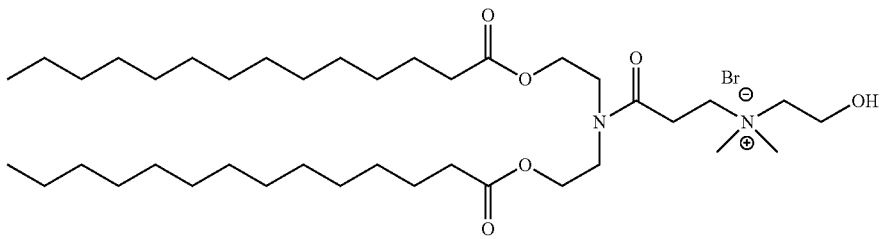

HE-Pr-DC

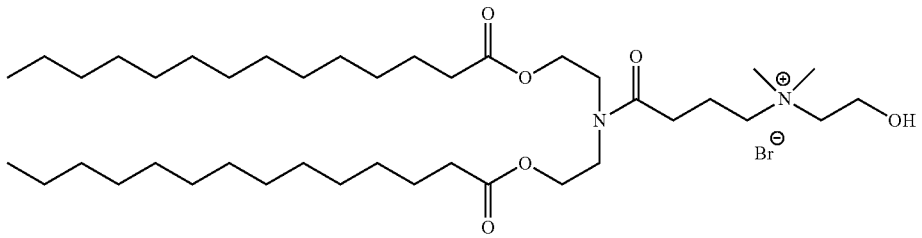

HES104

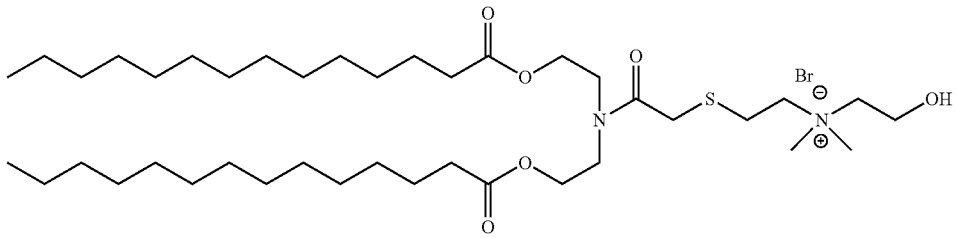

-continued
HE-DODC-DLin
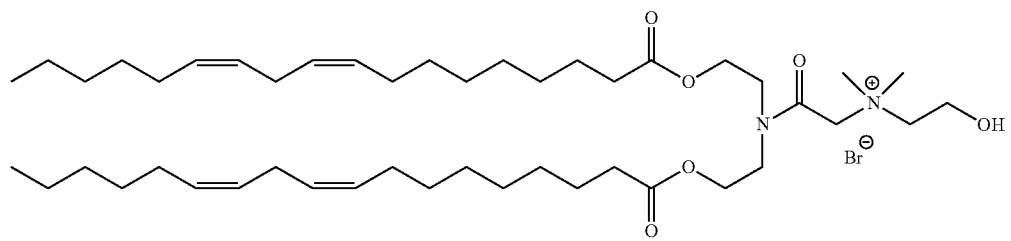
HE2-DODC
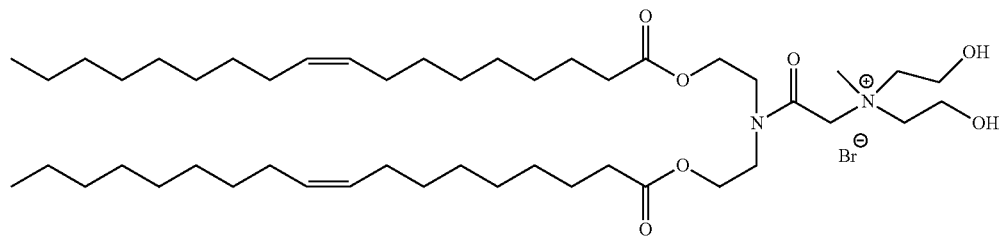
HE-DODC
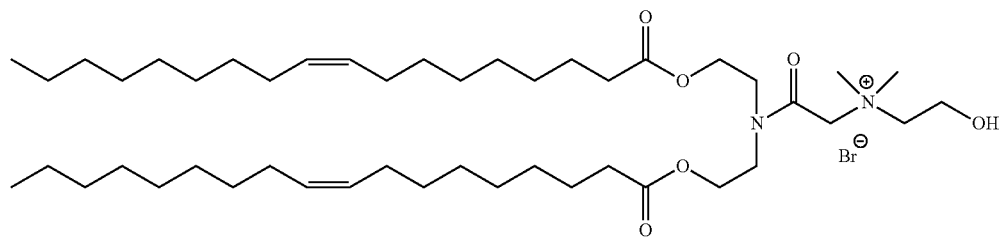
DE-Et-DODC
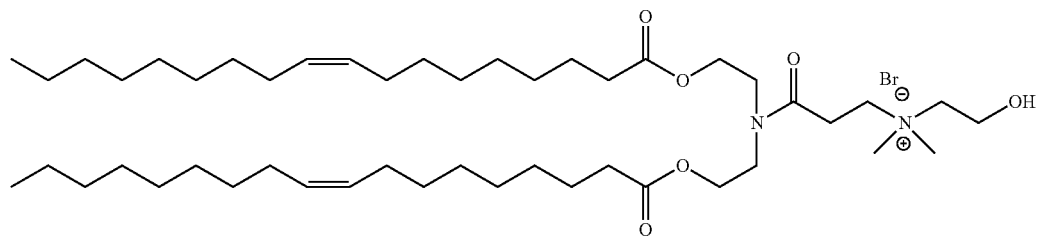
HE-Pr-DODC
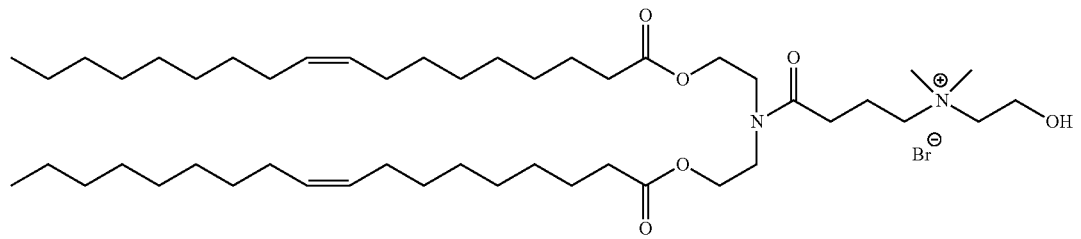
HES104DO
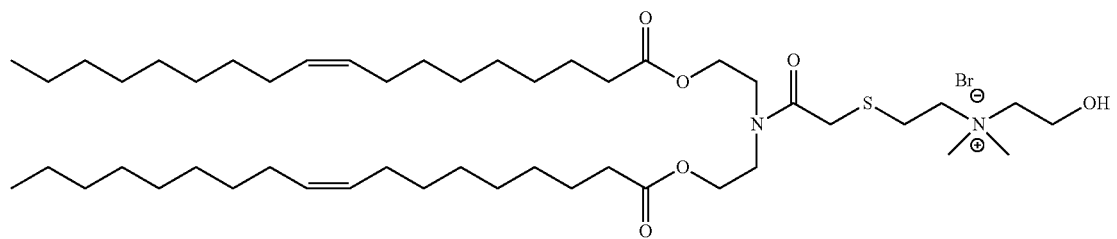

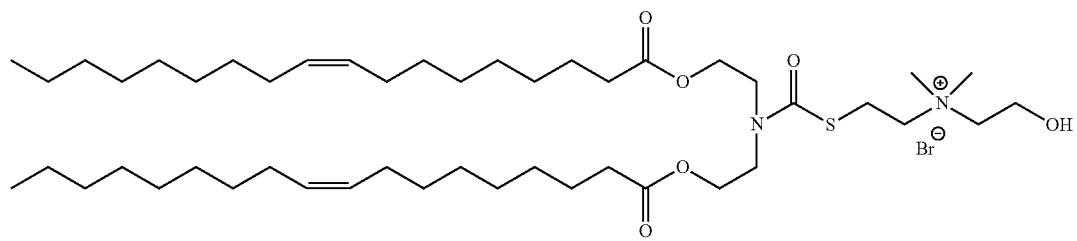

HETU104DO

Any siRNA molecule can be used within the scope of the description herein. In some embodiments, the siRNA 15 includes an antisense sequence to the mRNA coding sequence for human hsp47 exemplified by SEQ ID NO: 1, consisting of the following ribonucleotide sequence.

```
ucuuuggcuu uuuuggcgg agcuggggcg cccuccggaa gcguuuccaa cuuuccagaa   60
guuucucggg acgggcagga gggggugggg acugccauau auagaucccg ggagcagggg  120
agcgggcuaa gaguagaauc gugucgcggc ucgagagcga gagucacguc ccggcgcuag  180
cccagcccga cccaggccca ccguggugca cgcaaaccac uuccuggcca ugcgcucccu  240
ccugcuucuc agcgccuucu gccuccugga ggcggcccug gccgccgagg ugaagaaacc  300
ugcagccgca gcagcuccug gcacugcgga gaaguugagc cccaaggcgg ccacgcuugc  360
cgagcgcagc gccggccugg ccuucagcuu guaccaggcc auggccaagg accaggcagu  420
ggagaacauc cuggugucac ccgugguggu ggccucgucg cuagggcucg ugucgcuggg  480
cggcaaggcg accacggcgu cgcaggccaa ggcagugcug agcgccgagc agcugcgcga  540
cgaggaggug cacgccggcc ugggcgagcu gcugcgcuca cucagcaacu ccacggcgcg  600
caacgugacc uggaagcugg gcagccgacu guacggaccc agcucaguga gcuucgcuga  660
ugacuucgug cgcagcagca agcagcacua caacugcgag cacuccaaga ucaacuuccg  720
cgacaagcgc agcgcgcugc aguccaucaa cgaguggggcc gcgcagacca ccgacggcaa  780
gcugcccgag gucaccaagg acguggagcg cacggacggc gcccugcuag ucaacgccau  840
guucuucaag ccacacuggg augagaaauu ccaccacaag augguggaca accguggcuu  900 caugugugacu cgguccuaua ccgugggugu caugaugaug caccggacag gcucuacaa  960 cuacuacgac gacgagaagg aaaagcugca aaucguggag augccccugg cccacaagcu 1020
cuccagccuc aucauccuca ugccccauca cguggagccu cucgagcgcc uugaaaagcu 1080
gcuaaccaaa gagcagcuga agaucuggau ggggaagaug cagaagaagg cuguugccau 1140
cuccuugccc aagggugugg uggaggugac ccaugaccug cagaaacacc uggcugggcu 1200
gggccugacu gaggccauug acaagaacaa ggccgacuug ucacgcaugu caggcaagaa 1260
ggaccuguac cuggccagcg uguuccacgc caccgccuuu gaguuggaca cagauggcaa 1320
ccccuuugac caggacaucu acgggcgcga ggagcugcgc agccccaagc uguucuacgc 1380 cgaccaccc uucaucuucc uagugcggga cacccaaagc ggcucccugc uauucauugg 1440
gcgccugguc cggccuaagg gugacaagau gcgagacgag uuauagggcc ucagggugca 1500
cacaggaugg caggaggcau ccaaaggcuc cugagacaca ugggugcuau uggguuggg 1560 ggggaggugua gguaccagcc uuggauacuc caugggugg ggguggaaaa acagaccggg 1620
guucccgugu gccugagcgg accuuccag cuagaauuca cuccacuugg acaugggccc 1680
cagauaccau gaugcugagc ccggaaacuc cacauccugu gggaccuggg ccauagucau 1740
```

```
                                    -continued
ucugccugcc cugaaagucc cagaucaagc cugccucaau caguauucau auuuauagcc 1800
agguaccuuc ucaccuguga gaccaaauug agcuagggyg gucagccagc ccucuucuga 1860
cacuaaaaca ccucagcugc cucccagcu cuaucccaac cucucccaac uauaaaacua 1920
ggugcugcag ccccugggac caggcacccc cagaaugacc uggccgcagu gaggcggauu 1980
gagaaggagc ucccaggagg ggcuucuggg cagacucugg ucaagaagca ucgugucugg 2040
cguugugggg augaacuuuu uguuuuguuu cuuccuuuuu uaguucuuca aagauaggga 2100
gggaaggggg aacaugagcc uuuguugcua ucaauccaag aacuuauuug uacauuuuuu 2160
uuuucaauaa aacuuuucca augacauuuu guuggagcgu ggaaaaaa           2208
```

For example, the siRNA preferably consist of

```
                                           (SEQ. ID. NO. 2)
Sense (5'->3')     GGACAGGCCUCUACAACUATT
                                           (SEQ. ID. NO. 3)
Antisense (3'->5') TTCCUGUCCGGAGAUGUUGAU.
```

Such compositions also preferably include an aqueous medium. Preferably, such compositions consist essentially of at least one compound of formula I in a charge complex with the siRNA. Such compositions including a compound of formula I and siRNA can further comprise a liquid medium. In one embodiment, the liquid medium is suitable for injection into a living organism. Liquid media within the scope of any of the described embodiments of the description herein can be aqueous, that is, be comprises entirely of an aqueous solvent, and to include salts, buffers, and/or other pharmaceutical excipients. In another embodiment, the liquid media preferably consist of an aqueous solvent in combination with another liquid solvent such as, for example, an organic solvent. Liquid media within the scope of any of the described embodiments of the description herein also preferably include at least one organic solvent.

Organic solvents are known in the art per se and include $C_1$ to $C_4$ alcohols, dimethyl sulfoxide ("DMSO"), and the like. Those liquid media that include a mixture of water and at least one organic solvent are also within the scope of any of the embodiments of the description herein.

Also within the scope of the description herein are compositions that comprise at least one compound of formula I and a liposome. Some embodiments can include mixtures of compounds of formula I and a liposome. Other embodiments can include a liposome and one or more compounds of formula I in addition to cationic lipids that are not within the scope of formula I.

Compositions of the description herein that include at least one compound of formula I and a liposome that further comprises one or more retinoid conjugates. In preferred embodiments of the description herein, the retinoid conjugate is present at a concentration of about 0.3 to about 30 weight percent, based on the total weight of the composition or formulation, which is equivalent to about 0.1 to about 10 mol %, which is equivalent to a molar ratio of about 0.1 to about 10. Preferably, the retinoid conjugate is a retinoid-linker-lipid molecule or a retinoid-linker-retinoid molecule.

An example of a retinoid conjugates include those compounds of formula II:

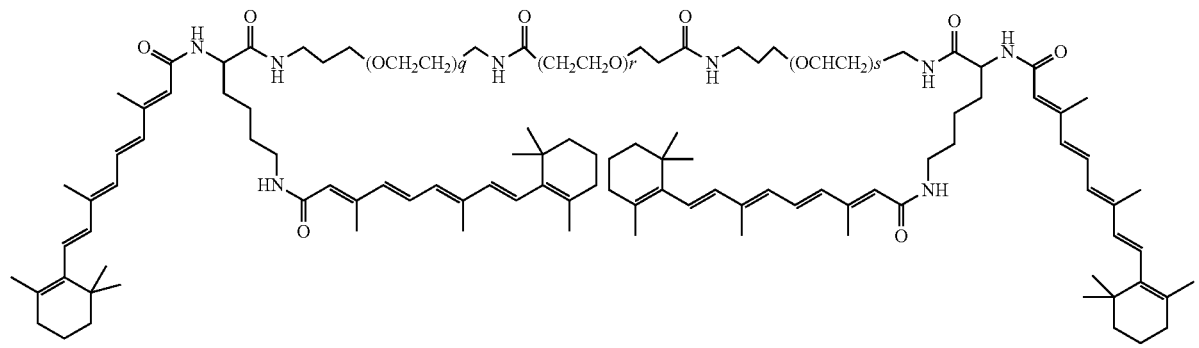

wherein q, r, and s are each independently 1, 2, 3, 4, 5, 6, 7, 8, 9, or 10, and enantiomers and diastereomers thereof.

Preferred compounds of formula II include those wherein q, r, and s are each independently 1, 2, 3, 4, 5, 6, or 7. More preferred are those compounds of formula II wherein q, r, and s are each independently 3, 4, or 5. Most preferred are those compounds of formula II wherein q is 3, r is 5, and s is 3. One example of a compound of formula II is DiVA-PEG-DiVA, which has the following structure.

PEG-lipids include PEG-phospholipids and PEG-ceramides such as, for example, PEG2000-DSPE, PEG2000-DPPE, PEG2000-DMPE, PEG2000-DOPE, PEG1000-DSPE, PEG1000-DPPE, PEG1000-DMPE, PEG1000-DOPE, PEG550-DSPE, PEG550-DPPE, PEG-550DMPE, PEG-1000DOPE, PEG-BML, PEG-cholesterol. PEG2000-ceramide, PEG1000-ceramide, PEG750-ceramide, PEG550-ceramide.

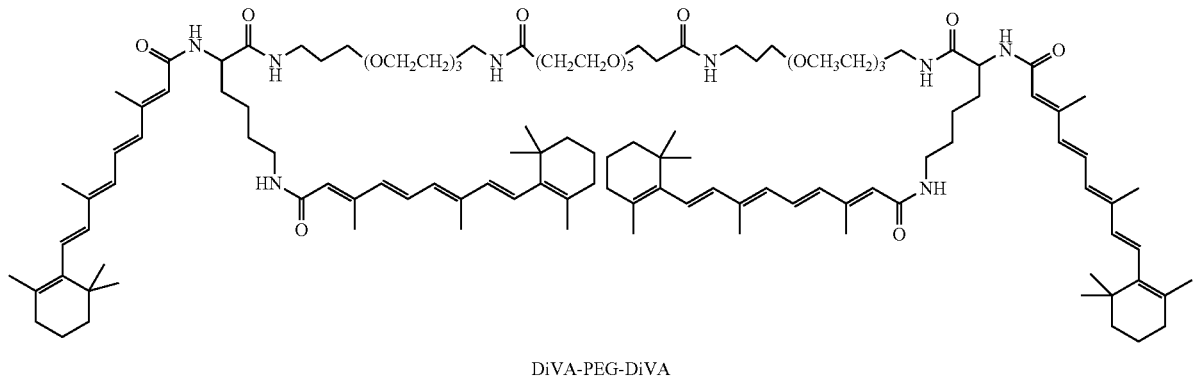

DiVA-PEG-DiVA

Di-vitamin A-PEG-di-vitamin A (DiVA-PEG-DiVA) includes stereocenters and all enantiomers and diastereomers are considered to be within the scope of the description herein.

The concentration of cationic lipids in compositions of the description herein, including those cationic lipids of formula I, can be from 1 to about 80 weight percent, based on the total weight of the lipid composition. More preferably, the concentration is from 1 to about 75 weight percent. Even more preferably, the concentration is from about 30 to about 75 weight percent. A concentration of from about 30 to about 75 weight percent corresponds to about 30 to 60 mol % and a molar ratio of about 30-60. Most preferred are those compositions having a cationic lipid concentration of about 50 weight percent. In formulations that contain a mixture of an ionizable cationic lipid and a quaternary amine cationic lipid of formula I, the preferred mol % is from 5% to 45 mol %, with even more preferred mixture at approximately 20 mol % of the ionizable cationic lipid and 20 mol % of the quaternary amine cationic lipid for formula I.

Such compositions preferably also include an aqueous medium. The cationic lipids, including those of formula I, are encapsulated within the liposome in such embodiments and are inaccessible to the aqueous medium. Furthermore, the cationic lipids, including those of formula I, are preferably localized on the outer surface of the liposome and be accessible to the aqueous medium.

Compositions of the description herein that include at least one compound of formula I and a liposome, and optionally a retinoid conjugate such as a compound of formula II, can also include siRNA.

In some embodiments, the siRNA are encapsulated by the liposome so that the siRNA is inaccessible to the aqueous medium. In other embodiments, the siRNA is not encapsulated by the liposome. In such embodiments, the siRNA is complexed on the outer surface of the liposome. In these embodiments, the siRNA is accessible to the aqueous medium.

The forgoing compositions also preferably include PEG-conjugated lipids, which are known in the art per se. Suitable For example, liposomes within the scope of the description herein are prepared using various PEG-lipids, incorporated using co-solubilization methods described herein. These formulations comprised cationic lipid:DOPE:cholesterol:DiVA-PEG-DiVA:PEG lipid (50:10:38:5:2 molar ratio) and each formulation was tested in the pHSC in vitro assay described herein using human/rat HSP-47-C siRNA at a concentration of 200 nM. The results are shown in the following table.

| PEG-Lipid | gp46 Gene Knockdown (%) | Std. Dev. |
|---|---|---|
| Untreated | 0 | 5.6 |
| RNAimax Control | 50.0 | 7.9 |
| PEG-BML | 95.5 | 1.7 |
| PEG1000-DMPE | 93.2 | 0.8 |
| PEG1000-DPPE | 92.8 | 1.3 |
| PEG1000-DSPE | 93.5 | 0.8 |
| PEG1000-DOPE | 90.7 | 2.5 |
| PEG2000-Ceramide | 91.8 | 1.0 |
| PEG2000-DMPE | 93.7 | 3.4 |
| PEG2000-DPPE | 91.1 | 1.4 |
| PEG2000-DSPE | 89.4 | 1.7 |

The foregoing compositions of the description herein include one or more phospholipids such as, for example, 1,2-distearoyl-sn-glycero-3-phosphocholine ("DSPC"), dipalmitoylphosphatidylcholine ("DPPC"), 1,2-dipalmitoyl-sn-glycero-3-phosphoethanolamine ("DPPE"), and 1,2-dioleoyl-sn-glycero-3-phosphoethanolamine ("DOPE"). Preferably, the helper lipid is DOPE.

In addition to the cationic lipid of Formula I, other lipids are useful. These include ionizable cationic lipids, including S104 consisting of the following formula.

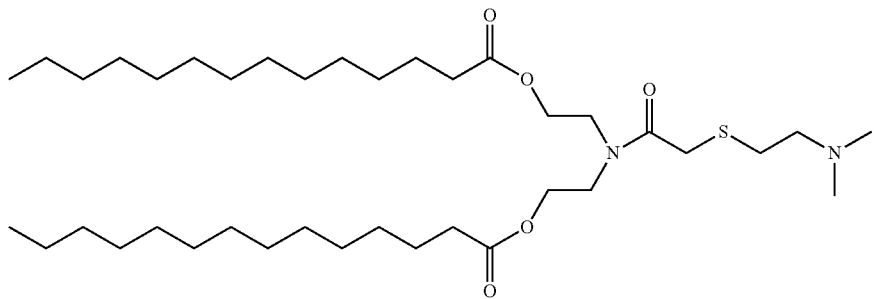

S104

Delivery formulations preferably consist of a cationic lipid of Formula I in combination with an ionizable cationic lipid. An ionizable cationic lipid preferably include, e.g., S104. The ionizable cationic lipid preferably is present at a concentration of 0 to 45 mol %, including a concentration selected from 5, 10, 15, 20, 25, 30, 35 40, and 45 mol %.

Also within the scope of the description herein are pharmaceutical formulations that include any of the aforementioned compositions in addition to a pharmaceutically acceptable carrier or diluent. Pharmaceutical formulations of the description herein include at least one therapeutic agent. Preferably, the therapeutic agent is an siRNA. It is envisioned that any siRNA molecule is within the scope of the description herein.

In preferred formulations of the description herein including siRNA, the siRNA is encapsulated by the liposome. In other embodiments, the siRNA is outside of the liposome. In those embodiments, the siRNA can be complexed to the outside of the liposome.

A useful range of cationic lipid:siRNA (lipid nitrogen to siRNA phosphate ratio, "N:P") is 0.2 to 5.0. Particularly preferred range of N:P is 1.5 to 2.5 for compositions and formulations of the description herein.

Preferred formulations of the description herein include those comprising HEDC:S104:DOPE:cholesterol:PEG-DMPE:DiVA-PEG-DiVA (20:20:30:25:5:2 molar ratio). Even more preferred embodiments include those HEDC:S104:DOPE:cholesterol:PEG-DMPE:DiVA-PEG-DiVA formulations wherein the DiVA-PEG-DiVA is co-solubilized.

Other preferred formulations of the description herein include those comprising HE-DODC:S104:DOPE:cholesterol:PEG-DMPE:DiVA-PEG-DiVA (20:20:30:25:5:2 molar ratio). Even more preferred embodiments include those HE-DODC:S104:DOPE:cholesterol:PEG-DMPE:DiVA-PEG-DiVA formulations wherein the DiVA-PEG-DiVA is co-solubilized.

Other preferred formulations of the description herein include those comprising DC-6-14:DOPE:cholesterol:DiVA-PEG-DiVA (40:30:30:5, molar ratios). In even more preferred embodiments, those formulations comprising DC-6-14:DOPE:cholesterol:DiVA-PEG-DiVA include DiVA-PEG-DiVA that is co-solubilized.

Also within the scope of the description herein are methods of delivering a therapeutic agent to a patient. These methods comprise providing a pharmaceutical formulation including any of the foregoing compositions and a pharmaceutically acceptable carrier or diluent, and administering the pharmaceutical formulation to the patient.

Definitions

As used herein, "alkyl" refers to a straight or branched fully saturated (no double or triple bonds) hydrocarbon group, for example, a group having the general formula $-C_nH_{2n+1}$. The alkyl group preferably have 1 to 50 carbon atoms (whenever it appears herein, a numerical range such as "1 to 50" refers to each integer in the given range; e.g., "1 to 50 carbon atoms" means that the alkyl group preferably consist of 1 carbon atom, 2 carbon atoms, 3 carbon atoms, etc., up to and including 50 carbon atoms, although the present definition also covers the occurrence of the term "alkyl" where no numerical range is designated). The alkyl group also preferably is a medium size alkyl having 1 to 30 carbon atoms or a lower alkyl having 1 to 5 carbon atoms. The alkyl group of the compounds is designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl and the like.

As used herein, "alkenyl" refers to an alkyl group that contains in the straight or branched hydrocarbon chain one or more double bonds. An alkenyl group is unsubstituted or substituted. When substituted, the substituent(s) is selected from the same groups disclosed above with regard to alkyl group substitution unless otherwise indicated.

As used herein, "alkynyl" refers to an alkyl group that contains in the straight or branched hydrocarbon chain one or more triple bonds. An alkynyl group is unsubstituted or substituted. When substituted, the substituent(s) is selected from the same groups disclosed above with regard to alkyl group substitution unless otherwise indicated.

As used herein, "halogen" refers to F, Cl, Br, and I.

As used herein, "mesylate" refers to $-SO_3CH_3$.

As used herein, the term "pharmaceutical formulation" refers to a mixture of a composition disclosed herein with one or more other chemical components, such as diluents or additional pharmaceutical carriers. The pharmaceutical formulation facilitates administration of the composition to an organism. Multiple techniques of administering a pharmaceutical formulation exist in the art including, but not limited to injection and parenteral administration.

As used herein, the term "pharmaceutical carrier" refers to a chemical compound that facilitates the incorporation of a compound into cells or tissues. For example dimethyl sulfoxide (DMSO) is selected from carriers that facilitate the uptake of many organic compounds into the cells or tissues of an organism.

As used herein, the term "diluent" refers to chemical compounds diluted in water that will dissolve the formulation of interest (e.g., the formulation that can include a compound, a retinoid, a second lipid, a stabilizing agent, and/or a therapeutic agent) as well as stabilize the biologically active form of the formulation. Salts dissolved in buffered solutions are utilized as diluents in the art. One commonly used buffered solution is phosphate-buffered saline because it mimics the salt conditions of human blood. Since buffer salts control the pH of a solution at low concentrations, a buffered diluent rarely modifies the biological activity of the formulation. As used herein, an "excipient" refers to an inert substance that is added to a formulation to provide, without limitation, bulk, consistency, stability, binding ability, lubrication, disintegrating ability, etc., to the composition. A "diluent" is a type of excipient.

As used herein, "therapeutic agent" refers to a compound that, upon administration to a mammal in a therapeutically effective amount, provides a therapeutic benefit to the mammal. A therapeutic agent is referred to herein as a drug. Those skilled in the art understand that the term "therapeutic agent" is not limited to drugs that have received regulatory approval. A "therapeutic agent" preferably is operatively associated with a compound as described herein, a retinoid, and/or a second lipid. For example, a second lipid as described herein can form a liposome, and the therapeutic agent can be operatively associated with the liposome, e.g., as described herein.

As used herein, "lipoplex formulations" refer to those formulations wherein the siRNA is outside of the liposome. In preferred lipoplex formulations, the siRNA is complexed to the outside of the liposome. Other preferred lipoplex formulations include those wherein the siRNA is accessible to any medium present outside of the liposome.

As used herein, "liposome formulations" refer to those formulations wherein the siRNA is encapsulated within the liposome. In preferred liposome formulations, the siRNA is inaccessible to any medium present outside of the liposome.

As used herein, the term "co-solubilized" refers to the addition of a component to the cationic lipid mixture before addition of an aqueous medium and resulting formation of the vesicle.

As used herein, the term "decorated" refers to the addition of a component after vesicle formation in an aqueous solvent, in which the component is preferentially localized on the surface of the vesicle accessible to the aqueous medium outside of the vesicle.

As used herein, "DC-6-14" refers to the following cationic lipid compound:

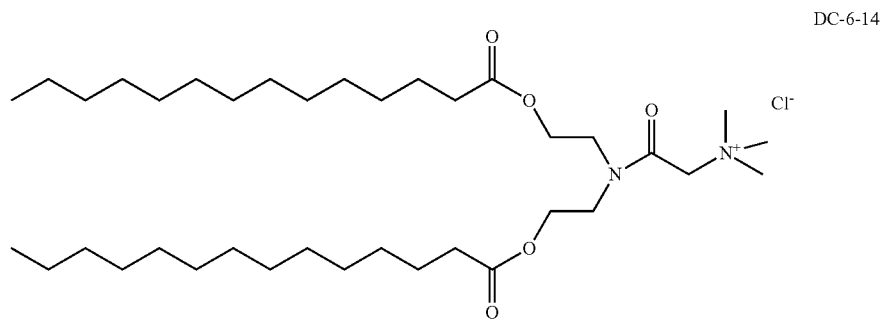 [SMILES: CCCCCCCCCCCCCC(=O)OCCN(CCOC(=O)CCCCCCCCCCCCC)C(=O)C[N+](C)(C)C ; [Cl-]]

DC-6-14

As used herein, "VA-PEG-VA" refers to the following compound:

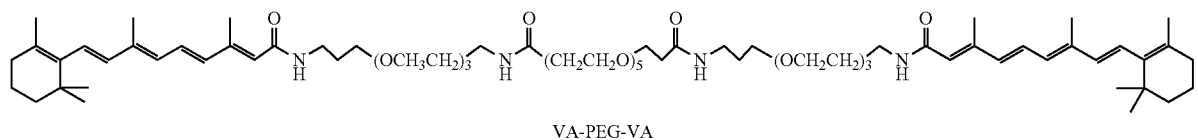

VA-PEG-VA

VA-PEG-VA can be prepared according to methods known in the art. A preferred method for prepared VA-PEG-VA is depicted in the following scheme:

As used herein, a "retinoid" is a member of the class of compounds consisting of four isoprenoid units joined in a head-to-tail manner, see Moss, BIOCHEMICAL NOMENCLATURE AND RELATED DOCUMENTS. "Vitamin A" is the generic descriptor for retinoids exhibiting qualitatively the biological activity of retinol. As used herein, retinoid refers to natural and synthetic retinoids including first generation, second generation, and third generation retinoids. Examples of naturally occurring retinoids include, but are not limited to, (1) 11-cis-retinal, (2) all-trans retinol, (3) retinyl palmitate, (4) all-trans retinoic acid, and (5) 13-cis-retinoic acids. Furthermore, the term "retinoid" encompasses retinols, retinals, retinoic acids, retinoids, and derivatives thereof.

As used herein, "retinoid conjugate" refers to a molecule that includes at least one retinoid moiety.

As used herein, "retinoid-linker-lipid molecule" refers to a molecule that includes at least one retinoid moiety attached to at least one lipid moiety through at least one linker such as, for example, a PEG moiety.

As used herein, "retinoid linker-retinoid molecule" refers to a molecule that includes at least one retinoid moiety attached to at least one other retinoid moiety (which is the same or different) through at least one linker such as, for example, a PEG moiety.

As used herein, the terms "lipid" and "lipophilic" are used herein in their ordinary meanings as understood by those skilled in the art. Non-limiting examples of lipids and lipophilic groups include fatty acids, sterols, $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl, $C_5$-$C_{50}$ heteroaryl, $C_2$-$C_{50}$ alkynyl, $C_2$-$C_{50}$ heteroalkynyl, $C_2$-$C_{50}$ carboxyalkenyl, and $C_2$-$C_{50}$ carboxyheteroalkenyl. A fatty acid is a saturated or unsaturated long-chain monocarboxylic acid that contains, for example, 12 to 24 carbon atoms A lipid is characterized as being essentially water insoluble, having a solubility in water of less than about 0.01% (weight basis). As used herein, the terms "lipid moiety" and "lipophilic moiety" refers to a lipid or portion thereof that has become attached to another group. For example, a lipid group is attached to another compound (e.g., a monomer) by a chemical reaction between a functional group (such as a carboxylic acid group) of the lipid and an appropriate functional group of a monomer.

As used herein, "siRNA" refers to small interfering RNA, also known in the art as short interfering RNA or silencing RNA. siRNA is a class of double stranded RNA molecules that have a variety of effects known in the art, the most notable being the interference with the expression of specific genes and protein expression.

As used herein, "encapsulated by the liposome" refers to a component being substantially or entirely within the liposome structure.

As used herein, "accessible to the aqueous medium" refers to a component being able to be in contact with the aqueous medium.

As used herein, "inaccessible to the aqueous medium" refers to a component not being able to be in contact with the aqueous medium.

As used herein, "complexed on the outer surface of the liposome" refers to a component being operatively associated with the outer surface of the liposome in an aqueous solvent and accessible to aqueous medium outside of the liposome.

As used herein, "localized on the outer surface of the liposome" refers to a component being at or near the outer surface of the liposome in an aqueous solvent and accessible to aqueous medium outside of the liposome.

As used herein, "charge complexed" refers to an electrostatic association.

As used herein, the term "operatively associated" refers to an electronic interaction between a compound as described herein, a therapeutic agent, a retinoid, and/or a second lipid. Such interaction is a chemical bond, including, but not limited to, a covalent bond, a polar covalent bond, an ionic bond, an electrostatic association, a coordinate covalent bond, an aromatic bond, a hydrogen bond, a dipole, or a van der Waals interaction. Those of ordinary skill in the art understand that the relative strengths of such interactions vary widely.

The term "liposome" is used herein in its ordinary meaning as understood by those skilled in the art, and refers to a lipid bilayer structure that contains lipids attached to polar, hydrophilic groups which form a substantially closed structure in aqueous media. In some embodiments, the liposome can be operatively associated with one or more compounds, such as a therapeutic agent and a retinoid. A liposome is preferably comprised of a single lipid bilayer (i.e., unilamellar) or two or more lipid bilayers (i.e., multilamellar). While the interior of a liposome consists of a variety of compounds, the exterior of the liposome is accessible to the aqueous formulation comprising the liposome. A liposome can be approximately spherical or ellipsoidal in shape.

Nucleic acid delivery systems include, for example, aqueous and nonaqueous gels, creams, multiple emulsions, microemulsions, liposomes, ointments, aqueous and nonaqueous solutions, lotions, aerosols, hydrocarbon bases and powders, and preferably contain excipients such as solubilizers, permeation enhancers (e.g., fatty acids, fatty acid esters, fatty alcohols and amino acids), and hydrophilic polymers (e.g., polycarbophil and polyvinylpyrolidone).

In addition to the cationic lipid of Formula I, other lipids are useful. These include ionizable cationic lipids, including S104, as shown as follows.

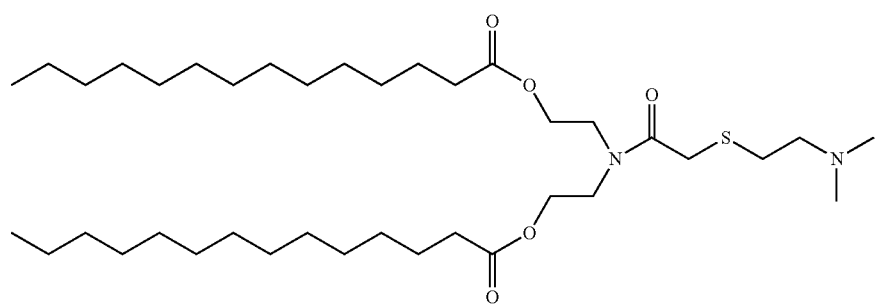

S104

Delivery formulations consist of a cationic lipid of Formula I in combination with an ionizable cationic lipid. An ionizable cationic lipid preferably includes, e.g., S104. The ionizable cationic lipid preferably is present at a concentration of 0 to 45 mol %, including a concentration selected from 5, 10, 15, 20, 25, 30, 35, 40, and 45 mol %.

A lipid conjugated to a polyethylene glycol molecule (PEG), preferably is present in the liposome particles. PEG-lipids include 1,2-dimyristoleoyl-sn-glycero-3-phosphoethanolamine-N-PEG (PEG-DMPE)

1,2-dipalmitoyl-sn-glycero-3-phosphoethanolamine-N-PEG (PEG-DPPE), 1,2-distearoyl-sn-glycero-3-phosphoethanolamine-N-PEG (PEG-DSPE), or 1,2-dioleoyl-sn-glycero-3-phosphoethanolamine-N-PEG (PEG-DOPE) and/or PEG-ceramide.

Delivery formulations consists of a cationic lipid of Formula I in combination with a PEG-lipid. The PEG-lipid preferably is at a concentration of 0 to 15 mol %, preferably 1 to 10 mol %, including a concentration selected from 1, 2, 3, 4, 5, 6, 7, 8, 9, and 10 mol %.

Non-limiting examples of non-cationic lipids include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

In certain embodiments, the amount of phospholipid present in particles comprises from about 0 mol % to about 55 mol %, more specifically at a concentration selected from the 5, 10, 15, 20, 25, 30, 35, 40, 45, 50, and 55 mol %. As a non-limiting example, the phospholipid is DOPE.

Additional examples of non-cationic lipids include sterols such as cholesterol and derivatives thereof such as cholestanol, cholestanone, cholestenone, coprostanol, cholesteryl-2'-hydroxyethyl ether, cholesteryl-4'-hydroxybutyl ether, and mixtures thereof.

In certain embodiments, the cholesterol or cholesterol derivative present in particles comprises from about 0 mol % to about 55 mol %, more specifically at a concentration selected from the 5, 10, 15, 20, 25, 30, 35, 40, 45, 50, and 55 mol %. As a non-limiting example, cholesterol is present in the lipid particles.

In certain other embodiments, the cholesterol present in lipid particles containing a mixture of phospholipid and cholesterol comprises from about 30 mol % to about 40 mol %, from about 30 mol % to about 35 mol %, or from about 35 mol % to about 40 mol % of the total lipid present in the particle. As a non-limiting example, a lipid particle comprising a mixture of phospholipid and cholesterol preferably at about 34 mol % of the total lipid present in the particle.

In further embodiments, the cholesterol present in lipid particles containing a mixture of phospholipid and cholesterol comprises from about 10 mol % to about 30 mol %, from about 15 mol % to about 25 mol %, or from about 17 mol % to about 23 mol % of the total lipid present in the particle. As a non-limiting example, a lipid particle comprising a mixture of phospholipid and cholesterol preferably comprise cholesterol at about 20 mol % of the total lipid present in the particle.

The retinoid or retinoid conjugate useful for delivery of nucleic acid is in a state in which it is dissolved in or mixed with a medium that can dissolve or retain it.

Any retinoid or retinoid conjugate is actively accumulated by stellate cells; examples of retinoid include, but are not limited to, tretinoin, adapalene, retinol palmitate, and in particular vitamin A, saturated vitamin A, retinoic acid, and retinal. Examples of the retinoid-conjugate include PEG-retinoid conjugates. The description herein utilizes the property of stellate cells to positively incorporate a retinoid and/or a retinoid conjugate, and by using the retinoid and/or retinoid conjugate as a drug carrier or by bonding to or being included in another drug carrier component, a desired material or body is transported specifically to stellate cells. A retinoid is a member of the class of compounds having a skeleton in which four isoprenoid units are bonded in a head-to-tail manner. See Moss, "Biochemical Nomenclature and Related Documents," 2nd Ed. Portland Press, pp. 247-251 (1992). Vitamin A is a generic descriptor for a retinoid qualitatively showing the biological activity of retinol. The retinoid in the description herein promotes specific substance delivery to a cancer cell and a CAF (that is, the substance is targeted at these cells). Such a retinoid is not particularly limited, and examples thereof include retinol, vitamin A, saturated vitamin A, retinal, retinoic acid, an ester of retinol and a fatty acid, an ester of an aliphatic alcohol and retinoic acid, etretinate, tretinoin, isotretinoin, adapalene, acitretine, tazarotene, and retinol palmitate, and vitamin A analogues such as fenretinide, and bexarotene. Retinoid-conjugates include PEG-conjugates, e.g., diVA-PEG-diVA and VA-PEG-VA.

The drug carrier of the description herein therefore preferably contains a drug carrier component other than a retinoid and/or retinoid-conjugate. Such a component is not particularly limited, and any component known in the fields of medicine and pharmacy is used, but it is preferable for it to be capable of including a retinoid and/or retinoid conjugate. Furthermore, the drug carrier of the description herein preferably contains a substance that improves incorporation into stellate cells, for example, retinol-binding protein (RBP). The bonding or inclusion of the retinoid and/or retinoid conjugate with the drug carrier of the description herein is also carried out by bonding or including the retinoid and/or retinoid conjugate with another component of the drug carrier by chemical and/or physical methods. Alternatively, bonding or inclusion of the retinoid and/or retinoid conjugate with the drug carrier of the description herein is also carried out by mixing the retinoid and/or retinoid conjugate having formation-affinity and basic components of the drug carrier, into the drug carrier components during preparation of the drug carrier.

The amount of retinoid and/or retinoid conjugate bonded to or included in the drug carrier of the description herein preferably is 0.01 mol % to 20 mol % as a ratio relative to the drug carrier components, preferably 0.2 mol % to 10 mol %, and more preferably 0.5 mol % to 5 mol %, including a concentration selected from the values 0.5, 1.0, 1.5, 2.0. 2.5, 3.0, 3.5, 4.0, 4.5, and 5.0 mol %.

In certain embodiments, the description herein provides for a liposome to be produced via mixing in a chamber. This includes a process that provides an aqueous solution comprising a nucleic acid such as an interfering RNA in a first reservoir, providing an organic lipid solution in a second reservoir, and mixing the aqueous solution with the organic lipid solution such that the organic lipid solution mixes with the aqueous solution so as to produce a liposome encapsulating the nucleic acid (e.g., siRNA) in a gradient of organic solvent concentration.

The liposome formed using the mixing method typically have a size of from about 40 nm to about 250 nm, from about 50 nm to about 150 nm, from about 60 nm to about 150 nm. The particles thus formed do not aggregate and are optionally sized to achieve a uniform particle size.

The drug carrier of the description herein is in any form suitable for transporting to target stellate cells, and examples of the form include, but are not limited to, polymer micelle, liposome, emulsion, microsphere, and nanosphere. Furthermore, the drug carrier of the description herein preferably includes in its interior the substance that is to be transported, be attached to the exterior of the substance that is to be transported, or be mixed with the substance that is to be transported as long as the retinoid and/or retinoid conjugate included therein is at least partially exposed on the exterior of the preparation before it reaches the stellate cells at the latest.

The drug carrier of the description herein specifically targets stellate cells and enables a desired effect such as, for example, inhibition or prevention of fibrosis to be exhibited with the maximum effect and minimum side effects by efficiently transporting to stellate cells a desired material or body such as, for example, a drug for controlling the activity or growth of stellate cells. The material or body that the present drug carrier delivers is not particularly limited, but it preferably has a size that enables physical movement in a living body from an administration site to the liver, pancreas, etc., where stellate cells are present. The drug carrier of the description herein therefore can transport not only a material such as an atom, a molecule, a compound, a protein, or a nucleic acid but also a body such as a vector, a virus particle, a cell, a drug release system constituted from one or more elements, or a micromachine. The material or body preferably has the property of exerting some effect on stellate cells, and examples thereof include one that labels stellate cells and one that controls the activity or growth of stellate cells.

Therefore, one embodiment of the present description is a drug for controlling the activity or growth of stellate cells that the drug carrier delivers, particularly any drug that directly or indirectly inhibits the physicochemical actions of stellate cells involved in the promotion of fibrosis, and examples thereof include, but are not limited to, TGFβ activity inhibitors such as a truncated TGFβ type II receptor and a soluble TGFβ type II receptor, growth factor preparations such as HGF and expression vectors therefor, MMP production promoters such as an MMP gene-containing adenovirus vector, TIMP production inhibitors such as an antisense TIMP nucleic acid, a PPARγ ligand, cell activation inhibitors and/or cell growth inhibitors such as an angiotensin activity inhibitor, a PDGF activity inhibitor, and a sodium channel inhibitor, and also apoptosis inducers such as compound 861 and gliotoxin, adiponectin, and a compound having Rho kinase inhibitory activity such as (+)-trans-4-(1-aminoethyl)-1-(4-pyridylcarbamoyl)cyclohexane. Furthermore, the 'drug for controlling the activity or growth of stellate cells' in the description herein is preferably is any drug that directly or indirectly promotes the physicochemical actions of stellate cells directly or indirectly involved in the inhibition of fibrosis, and examples thereof include, but are not limited to, a drug for promoting a collagen degradation system, e.g., MMP production promoters such as an MMP expression vector, HGF, and drugs having HGF-like activity such as HGF analogues and expression vectors therefor.

Other examples of the drug for controlling the activity or growth of stellate cells in the description herein include a drug for controlling the metabolism of an extracellular matrix such as collagen, for example, a substance having an effect in inhibiting the expression of a target molecule, such as siRNA, ribozyme, and antisense nucleic acid (including RNA, DNA, PNA, or a composite thereof), a substance having a dominant negative effect, and vectors expressing same, that target, for example, an extracellular matrix constituent molecule produced by stellate cells or target one or more molecules that have the function of producing or secreting the extracellular matrix constituent molecule.

The description herein also relates to a medicine for treating a stellate cell-related disorder, the medicine containing the drug carrier and the drug for controlling the activity or growth of stellate cells, and relates to the use of the drug carrier in the production of a pharmaceutical composition for treating a stellate cell-related disorder. The stellate cell-related disorder referred to herein means a disorder in which stellate cells are directly or indirectly involved in the process of the disorder, that is, the onset, exacerbation, improvement, remission, cure, etc., of the disorder, and examples thereof include hepatic disorders such as hepatitis, in particular chronic hepatitis, hepatic fibrosis, hepatic cirrhosis, and liver cancer, and pancreatic disorders such as pancreatitis, in particular chronic pancreatitis, pancreatic fibrosis, and pancreatic cancer.

In the medicine of the description herein, the drug carrier preferably includes a drug in its interior, be attached to the exterior of a drug-containing substance, or be mixed with a drug as long as the retinoid and/or retinoid-conjugate included in the drug carrier is at least partially exposed on the exterior of the preparation before it reaches the stellate cells at the latest. Therefore, depending on the route of administration or manner in which the drug is released, the medicine preferably is covered with an appropriate material, such as, for example, an enteric coating or a material that disintegrates over time, or is incorporated into an appropriate drug release system.

The description herein includes a drug carrier or medicine preparation kit containing one or more containers, one or more drug carrier constituents, a retinoid and/or a retinoid conjugate, and/or a drug, and an essential component for the drug carrier or the medicine, provided in the form of the kit. The kit contains, in addition to those components described above, a preparation method or an administration method for the drug carrier and the medicine. Furthermore, the kit of the description herein preferably contains all components for completing the drug carrier or the medicine but need not necessarily contain all of the components. The kit of the description herein therefore need not contain a reagent or a solvent that is normally available at a place of medical treatment, an experimental facility, such as, for example, sterile water, saline, or a glucose solution.

The description herein further relates to a method for treating a stellate cell-related disorder, the method including administering an effective amount of the medicine to a subject in need thereof. The effective amount referred to here is an amount that suppresses onset of the target disorder, reduces symptoms thereof, or prevents progression thereof, and is preferably an amount that prevents onset of the target disorder or cures the target disorder. It is also preferably an amount that does not cause an adverse effect that exceeds the benefit from administration. Such an amount is determined as appropriate by an in vitro test using cultured cells, or by a test in a model animal such as a mouse, a rat, a dog, or a pig, and such test methods are well known to a person skilled in the art.

In the method of the description herein, the term "subject" means any living individual, preferably an animal, more preferably a mammal, and yet more preferably a human individual. In the description herein, the subject is healthy or affected with some disorder, and in the case of treatment of a disorder being intended, the subject typically means a subject affected with the disorder or having a risk of being affected.

Furthermore, the term "treatment" includes all types of medically acceptable prophylactic and/or therapeutic intervention for the purpose of the cure, temporary remission, prevention, etc., of a disorder. For example, when the disorder is hepatic fibrosis, the term "treatment" includes medically acceptable intervention for various purposes including delaying or halting the progression of fibrosis, regression or disappearance of lesions, prevention of the onset of fibrosis, or prevention of recurrence.

The description herein also relates to a method for delivering a drug to stellate cells using the drug carrier. This method includes, but is not limited to, a step of supporting a substance to be delivered on the drug carrier, and a step of administering or adding the drug carrier carrying the substance to be delivered to a stellate cell-containing living body or medium, such as, for example, a culture medium. These steps are achieved as appropriate in accordance with any known method, the method described herein. This delivery method is combined with another delivery method, for example, another delivery method in which an organ where stellate cells are present is the target.

Nucleic acid molecules are adapted for use to prevent or treat fibroses (e.g., liver, kidney, peritoneal, and pulmonary) diseases, traits, conditions and/or disorders, and/or any other trait, disease, disorder or condition that is related to or will respond to the levels of hsp47 in a cell or tissue, alone or in combination with other therapies. A nucleic acid molecule includes a delivery vehicle, including liposomes, for administration to a subject, carriers and diluents and their salts, and/or can be present in pharmaceutically acceptable formulations.

The nucleic acid molecules of the description herein include sequences shown in the sequence listing.

The nucleic acid molecules are administered via pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the nucleic acid compositions of the description can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight.

Aerosols of liquid particles preferably include a nucleic acid molecules disclosed herein and can be produced by any suitable means, such as with a nebulizer. Nebulizers are commercially available devices which transform solutions or suspensions of an active ingredient into a therapeutic aerosol mist either by means of acceleration of a compressed gas, typically air or oxygen, through a narrow venturi orifice or by means of ultrasonic agitation. Suitable formulations for use in nebulizers include the active ingredient in a liquid carrier in an amount of up to 40% w/w, preferably less than 20% w/w of the formulation. The carrier is typically water or a dilute aqueous alcoholic solution, preferably made isotonic with body fluids by the addition of, e.g., sodium chloride or other suitable salts. Optional additives include preservatives if the formulation is not prepared sterile, e.g., methyl hydroxybenzoate, anti-oxidants, flavorings, volatile oils, buffering agents and emulsifiers and other formulation surfactants. The aerosols of solid particles including the active composition and surfactant can likewise be produced with any solid particulate aerosol generator. Aerosol generators for administering solid particulate therapeutics to a subject produce particles which are respirable, as explained above, and generate a volume of aerosol containing a predetermined metered dose of a therapeutic composition at a rate suitable for human administration. One illustrative type of solid particulate aerosol generator is an insufflator. Suitable formulations for administration by insufflation include finely comminuted powders which can be delivered by means of an insufflator. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically includes from 0.1 to 100 w/w of the formulation. A second type of illustrative aerosol generator includes a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume to produce a fine particle spray containing the active ingredient. Suitable propellants include certain chlorofluorocarbon compounds, e.g., dichlorodifluoromethane, trichlorofluoromethane, dichlorotetrafluoroethane or mixtures thereof. The formulation can additionally contain one or more co-solvents, for example, ethanol, emulsifiers or other formulation surfactants, such as oleic acid or sorbitan trioleate, anti-oxidants or suitable flavoring agents.

Nucleic acid molecules are administered to the central nervous system (CNS) or peripheral nervous system (PNS). Experiments have demonstrated the efficient in vivo uptake of nucleic acids by neurons. Nucleic acid molecules are therefore amenable to delivery to and uptake by cells in the CNS and/or PNS.

Delivery of nucleic acid molecules to the CNS is provided by a variety of different strategies. Traditional approaches to CNS delivery that can be used include, but are not limited to, intrathecal and intracerebroventricular administration, implantation of catheters and pumps, direct injection or perfusion at the site of injury or lesion, injection into the brain arterial system, or by chemical or osmotic opening of the blood-brain barrier. Other approaches can include the use of various transport and carrier systems, for example though the use of conjugates and biodegradable polymers.

Nucleic acid molecules are formulated or complexed with polyethyleneimine (e.g., linear or branched PEI) and/or polyethyleneimine derivatives, including for example grafted PEIs such as galactose PEI, cholesterol PEI, antibody derivatized PEI, and polyethylene glycol PEI (PEG-PEI) derivatives thereof.

Nucleic acid molecules include a bioconjugate.

Compositions, methods and kits disclosed herein preferably include an expression vector that includes a nucleic acid sequence encoding at least one nucleic acid molecule of the description in a manner that allows expression of the nucleic acid molecule. Methods of introducing nucleic acid molecules or one or more vectors capable of expressing the strands of dsRNA into the environment of the cell will depend on the type of cell and the make-up of its environment. The nucleic acid molecule or the vector construct are directly introduced into the cell (i.e., intracellularly); or introduced extracellularly into a cavity, interstitial space, into the circulation of an organism, introduced orally, or are introduced by bathing an organism or a cell in a solution containing dsRNA. The cell is preferably a mammalian cell, more preferably a human cell. The nucleic acid molecule of the expression vector can include a sense region and an antisense region. The antisense region can include a sequence complementary to a RNA or DNA sequence encoding hsp47 and the sense region can include a sequence complementary to the antisense region. The nucleic acid molecule can include two distinct strands having complementary sense and antisense regions. The nucleic acid molecule can include a single strand having complementary sense and antisense regions.

Nucleic acid molecules that interact with target RNA molecules and down-regulate gene encoding target RNA molecules (e.g., target RNA molecules referred to by Genbank Accession numbers herein) are expressed from transcription units inserted into DNA or RNA vectors. Recombinant vectors can be DNA plasmids or viral vectors. Nucleic acid molecule expressing viral vectors can be constructed based on, but not limited to, adeno-associated virus, retrovirus, adenovirus, or alphavirus. The recombinant vectors capable of expressing the nucleic acid molecules can be delivered as described herein, and persist in target cells. Alternatively, viral vectors can be used that provide for transient expression of nucleic acid molecules. Such vectors can be repeatedly administered as necessary. Once expressed, the nucleic acid molecules bind and down-regulate gene function or expression via RNA interference (RNAi). Delivery of nucleic acid molecule expressing vectors can be systemic, such as by intravenous or intramuscular administration, by administration to target cells explanted from a subject followed by reintroduction into the subject, or by any other means that would allow for introduction into the desired target cell.

In another aspect, the present disclosure relates to a pharmaceutical formulation comprising one or more physiologically acceptable surface active agents, pharmaceutical carriers, diluents, excipients, and suspension agents, or a combination thereof; and a formulation (e.g., the formulation that can include a compound, a retinoid, a second lipid, a stabilizing agent, and/or a therapeutic agent) disclosed herein. Acceptable additional pharmaceutical carriers or diluents for therapeutic use are well known in the pharmaceutical art, and are described, for example, in REMINGTON'S PHARMACEUTICAL SCIENCES, which is incorporated herein by reference in its entirety. Preservatives, stabilizers, dyes, and the like are provided in the pharmaceutical formulation. For example, sodium benzoate, ascorbic acid and esters of p-hydroxybenzoic acid are added as preservatives. In addition, antioxidants and suspending agents are used. In various embodiments, alcohols, esters, sulfated aliphatic alcohols, and the like are used as surface active agents; sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like are used as excipients; coconut oil, olive oil, sesame oil, peanut oil, soya are used as suspension agents or lubricants; cellulose acetate phthalate as a derivative of a carbohydrate such as cellulose or sugar, or methylacetate-methacrylate copolymer as a derivative of polyvinyl are used as suspension agents; and plasticizers such as ester phthalates and the like are used as suspension agents.

The pharmaceutical formulations described herein are administered to a human patient per se, or in pharmaceutical formulations where they are mixed with other active ingredients, as in combination therapy, or suitable pharmaceutical carriers or excipient(s). Techniques for formulation and administration of the compounds of the instant application are found in REMINGTON'S PHARMACEUTICAL SCIENCES.

Suitable routes of administration include, for example, parenteral delivery, including intramuscular, subcutaneous, intravenous, intramedullary injections, as well as intrathecal, direct intraventricular, intraperitoneal, intranasal, or intraocular injections. The formulation (e.g., the formulation that can include a compound, a retinoid, a second lipid, a stabilizing agent, and/or a therapeutic agent) can also be administered in sustained or controlled release dosage forms, including depot injections, osmotic pumps, and the like, for prolonged and/or timed, pulsed administration at a predetermined rate. Additionally, the route of administration are local or systemic.

The pharmaceutical formulations are manufactured in a manner that is itself known, e.g., by means of conventional mixing, dissolving, granulating, dragée-making, levigating, emulsifying, encapsulating, entrapping or tableting processes.

Pharmaceutical formulations are formulated in any conventional manner using one or more physiologically acceptable pharmaceutical carriers comprising excipients and auxiliaries which facilitate processing of the active compounds into preparations which can be used pharmaceutically. Proper formulation is dependent upon the route of administration chosen. Any of the well-known techniques, pharmaceutical carriers, and excipients are used as suitable and as understood in the art; e.g., in REMINGTON'S PHARMACEUTICAL SCIENCES.

Injectables are prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical formulations contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations are utilized.

Pharmaceutical formulations for parenteral administration, e.g., by bolus injection or continuous infusion, include aqueous solutions of the active formulation (e.g., the formulation that can include a compound, a retinoid, a second lipid, a stabilizing agent, and/or a therapeutic agent) in water-soluble form. Additionally, suspensions of the active compounds are prepared as appropriate oily injection suspensions. Aqueous injection suspensions preferably contain substances which increase the viscosity of the suspension, such as sodium carboxymethyl cellulose, sorbitol, or dextran. Optionally, the suspension also preferably contain suitable stabilizers or agents that increase the solubility of the compounds to allow for the preparation of highly concentrated solutions. Formulations for injection preferably are presented in unit dosage form, e.g., in ampoules or in multi-dose containers, with an added preservative. The formulations preferably take such forms as suspensions, solutions or emulsions in oily or aqueous vehicles, and preferably contain formulatory agents such as suspending, stabilizing and/or dispersing agents. Alternatively, the active ingredient preferably is a powder for constitution with a suitable vehicle, e.g., sterile pyrogen-free water, before use.

In addition to the preparations described previously, the formulations preferably are also formulated as a depot preparation. Such long acting formulations are preferably administered by intramuscular injection. Thus, for example, the formulations (e.g., the formulation preferably includes a compound, a retinoid, a second lipid, a stabilizing agent, and/or a therapeutic agent) is formulated with suitable polymeric or hydrophobic materials (for example as an emulsion in an acceptable oil) or ion exchange resins, or as sparingly soluble derivatives, for example, as a sparingly soluble salt.

The compositions and formulations of the description herein also are preferably formulated for topical delivery and is applied to the subject's skin using any suitable process for application of topical delivery vehicle. For example, the formulation preferably is applied manually, using an applicator, or by a process that involves both. Following application, the formulation is worked into the subject's skin, e.g., by rubbing. Application is preferably performed multiple times daily or on a once-daily basis. For example, the formulation are applied to a subject's skin once a day, twice a day, or multiple times a day, or once every two days, once every three days, or about once every week, once every two weeks, or once every several weeks.

Some embodiments herein are directed to a method of delivering a therapeutic agent to a cell. For example, some embodiments are directed to a method of delivering a therapeutic agent such as siRNA into a cell. Suitable cells for use according to the methods described herein include prokaryotes, yeast, or higher eukaryotic cells, including plant and animal cells (e.g., mammalian cells). In some embodiments, the cells can be human fibrosarcoma cells (e.g., HT1080 cell line). In other embodiments, the cells can be hepatic stellate cells (LX2 cell line). In other embodiments, the cells can be cancer cells. In yet other embodiments, the cells can be stem cells (pHSC cell line). Cell lines which are model systems for cancer is used, including but not limited to breast cancer (MCF-7, MDA-MB-438 cell lines), U87 glioblastoma cell line, B16F0 cells (melanoma), HeLa cells (cervical cancer), A549 cells (lung cancer), and rat tumor cell lines GH3 and 9 L. In these embodiments, the formulations described herein are used to transfect a cell. These embodiments include contacting the cell with a formulation described herein that includes a therapeutic agent, to thereby deliver a therapeutic agent to the cell.

Described herein are methods for treating a condition characterized by abnormal fibrosis, which include administering a therapeutically effective amount of a formulation described herein. Conditions characterized by abnormal fibrosis include cancer and/or a fibrotic disease. Types of cancer that are treated or ameliorated by a formulation described herein include, but are not limited to, lung cancer, pancreatic cancer, breast cancer, liver cancer, stomach cancer, and colon cancer. In an embodiment, the cancer that is treated or ameliorated is pancreatic cancer. In another embodiment, the cancer that is treated or ameliorated is lung cancer. Types of fibrotic disease that are treated or ameliorated by a formulation described herein include, but are not limited to, hepatic fibrosis, hepatic cirrhosis, pancreatitis, pancreatic fibrosis, cystic fibrosis, vocal cord scarring, vocal cord mucosal fibrosis, laryngeal fibrosis, pulmonary fibrosis, idiopathic pulmonary fibrosis, cystic fibrosis, myelofibrosis, retroperitoneal fibrosis, and nephrogenic systemic fibrosis. In an embodiment, the condition that is treated or ameliorated is hepatic fibrosis.

The formulations or pharmaceutical compositions described herein is administered to the subject by any suitable means. Non-limiting examples of methods of administration include, among others, (a) administration via injection, subcutaneously, intraperitoneally, intravenously, intramuscularly, intradermally, intraorbitally, intracapsularly, intraspinally, intrasternally, or the like, including infusion pump delivery; (b) administration locally such as by injection directly in the renal or cardiac area, e.g., by depot implantation; as well as deemed appropriate by those of skill in the art for bringing the active compound into contact with living tissue.

Pharmaceutical compositions suitable for administration include formulations (e.g., the formulation that can include a compound, a retinoid, a second lipid, a stabilizing agent, and/or a therapeutic agent) where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage ranges broadly, depending upon the desired effects and the therapeutic indication. Typically, dosages are about 10 microgram/kg to about 100 mg/kg body weight, preferably about 100 microgram/kg to about 10 mg/kg body weight. Alternatively dosages are based and calculated upon the surface area of the patient, as understood by those of skill in the art.

The exact formulation, route of administration and dosage for the pharmaceutical compositions are chosen by the individual physician in view of the patient's condition. (See, e.g., Fingl, et al., THE PHARMACOLOGICAL BASIS OF THERAPEUTICS, hereby incorporated herein in its entirety. Typically, the dose range of the composition administered to the patient can be from about 0.5 to about 1000 mg/kg of the patient's body weight. The dosage is a single one or a series of two or more given in the course of one or more days, as is needed by the patient. In instances where human dosages for compounds have been established for at least some condition, the dosages are about the same, or dosages that are about 0.1% to about 500%, more preferably about 25% to about 250% of the established human dosage. Where no human dosage is established, as will be the case for newly-discovered pharmaceutical compositions, a suitable human dosage is inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition, for example, is evaluated in part by standard prognostic evaluation methods. Further, the dose and perhaps dose frequency, also vary according to the age, body weight, and response of the individual patient. A program comparable to that discussed above is used in veterinary medicine.

Although the exact dosage will be determined on a drug-by-drug basis, in most cases, some generalizations regarding the dosage can be made. The daily dosage regimen for an adult human patient is, for example, a dose of about 0.1 mg to 2000 mg of each active ingredient, preferably about 1 mg to about 500 mg, e.g., 5 to 200 mg. In other embodiments, an intravenous, subcutaneous, or intramuscular dose of each active ingredient of about 0.01 mg to about 100 mg, preferably about 0.1 mg to about 60 mg, e.g., about 1 to about 40 mg is used. In cases of administration of a pharmaceutically acceptable salt, dosages are calculated as the free base. In some embodiments, the formulation is administered 1 to 4 times per day. Alternatively the formulations is administered by continuous intravenous infusion, preferably at a dose of each active ingredient up to about 1000 mg per day. As will be understood by those of skill in the art, in certain situations it is necessary to administer the formulations disclosed herein in amounts that exceed, or even far exceed, the above-stated, preferred dosage range in order to effectively and aggressively treat particularly aggressive diseases or infections. In some embodiments, the formulations is administered for continuous therapy, for example for a week or more, or for months or years.

Dosage amount and interval are adjusted individually to provide plasma levels of the active moiety which are sufficient to maintain the modulating effects, or minimal effective concentration (MEC). The MEC vary for each compound but are estimated from in vitro data. Dosages necessary to achieve the MEC will depend on individual characteristics and route of administration. However, HPLC assays or bioassays are used to determine plasma concentrations.

Dosage intervals are also determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug is unrelated to plasma concentration.

The amount of formulation administered are dependent on the subject being treated, on the subject's weight, the severity of the affliction, the manner of administration and the judgment of the prescribing physician.

Formulations disclosed herein (e.g., the formulation that includes a compound, a retinoid, a second lipid, a stabilizing agent, and/or a therapeutic agent) are evaluated for efficacy and toxicity using known methods. For example, the toxicology of a particular compound, or of a subset of the compounds, sharing certain chemical moieties, are established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, are determined using known methods. The efficacy of a particular compound are established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models are used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The formulations are, if desired, presented in a pack or dispenser device which contain one or more unit dosage forms containing the active ingredient. The pack for example comprises metal or plastic foil, such as a blister pack. The pack or dispenser device is accompanied by instructions for administration. The pack or dispenser is alternatively be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. Compositions comprising a compound formulated in a compatible pharmaceutical carrier are be prepared, placed in an appropriate container, and labeled for treatment of an indicated condition.

It is understood that, in any compound described herein having one or more stereocenters, if an absolute stereochemistry is not expressly indicated, then each center is independently be of R-configuration or S-configuration or a mixture thereof. Thus, the compounds provided herein are enantiomerically pure or stereoisomeric mixtures. In addition it is understood that, in any compound having one or more double bond(s) generating geometrical isomers that are defined as E or Z each double bond independently is E or Z a mixture thereof. Likewise, all tautomeric forms are also intended to be included.

The description herein can be further exemplified by reference to the following examples. These examples are illustrative, only, and are not intended to limit the invention description recited in the claims.

EXAMPLES

Example 1: Preparation of 2-(bis(2-(tetradecanoyloxy)ethyl)amino)-N-(2-hydroxyethyl)-N,N-dimethyl-2-oxoethan-aminium bromide (HEDC)

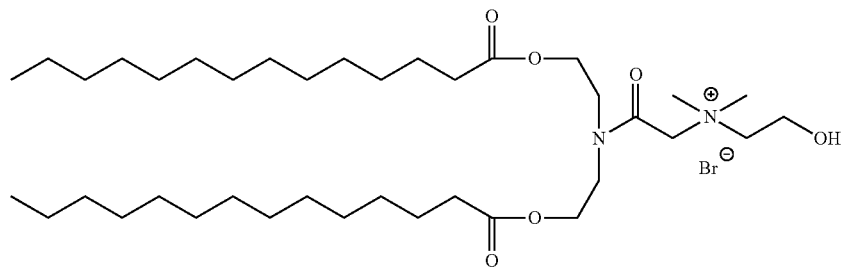 [SMILES: CCCCCCCCCCCCCC(=O)OCCN(CCOC(=O)CCCCCCCCCCCCC)C(=O)C[N+](C)(C)CCO ; [Br-]]

Preparation of 2,2'-(tert-butoxycarbonylazanediyl)bis(ethane-2,1-diyl) ditetradecanoate (HEDC-BOC-IN)

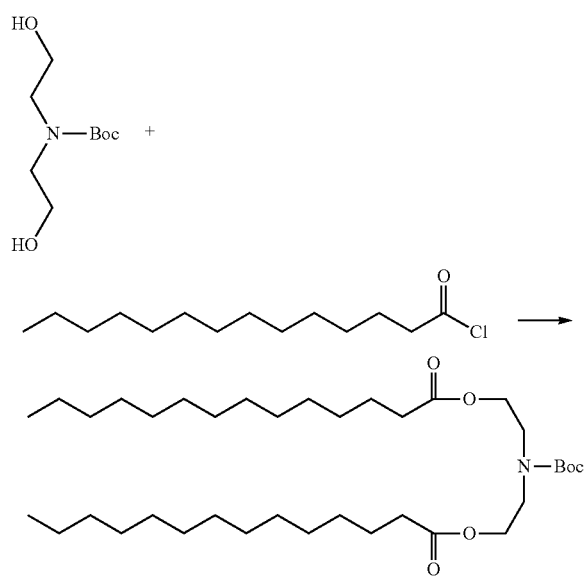

A solution of N—BOC-diethanolamine (194 g, 0.946 mol), triethylamine (201 g, 2.03 mol) and diaminopyridine (23.1 g, 0.19 mol) in dichloromethane (DCM) (1750 mL) was cooled to 0° C. A solution of myristoyl chloride (491 g, 1.99 mol) in DCM (440 mL) was added for 50 minutes at 0-10° C., and the mixture was warmed to ambient temperature. Full conversion was indicated by thin-layer chromatography (TLC) after 1.5 hours at 20-24° C. Water (1750 mL) was added and pH 8.3 was measured by a pH meter. The organic phase was separated, washed with (1) 6% sodium bicarbonate (NaHCO₃) (500 mL), (2) 0.3 M hydrochloric acid (HCl) (1700 mL), (3) 12.5% sodium chloride (1700 mL), and dried with anhydrous magnesium sulphate (120 g). Evaporation of the filtrate at 50° C. and 50 mBar gave 622 g of 2,2'-(tert-butoxycarbonylazanediyl)bis(ethane-2,1-diyl) ditetradecanoate, (HEDC-BOC-IN). This residue was used in the next step.

Preparation of 2,2'-(tert-butoxycarbonylazanediyl)bis(ethane-2,1-diyl) ditetradecanoate (HEDC-amine-IN) TFA Salt

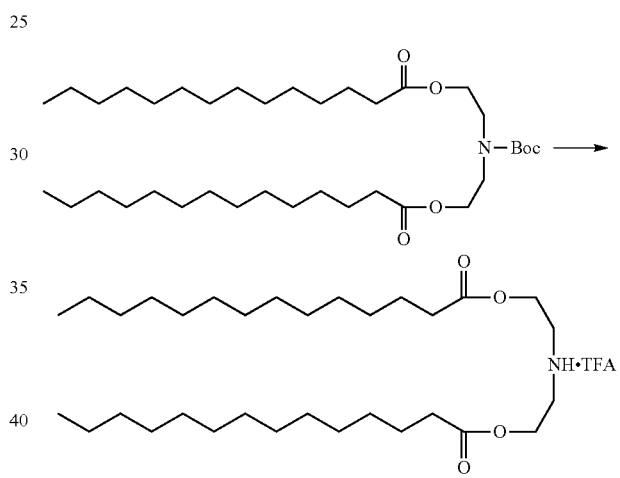

HEDC-BOC-IN (620 g, 0.990 mol) was transformed into a liquid by brief heating into a 50° C.-bath and then cooled below 25° C. Trifluoroacetic acid (TFA) (940 mL, 1.39 kg, 1.18 mol) was added to the liquid for 30 minutes, using moderate cooling in order to maintain a temperature not higher than 25° C. Having added two thirds of the amount of TFA, significant gas evolution was observed. The reaction mixture was stirred overnight at ambient temperature. TLC indicated traces of HEDC-BOC-IN. The reaction mixture was heated for distillation of TFA under reduced pressure (125-60 mBar) from a water bath of 50-55° C., and distillation was continued. TFA fumes were absorbed in a scrubber with 10% sodium hydroxide. Heptane (2000 mL) was added, stirred, and distilled off under reduced pressure. Heptane (2000 mL) was added to the partly solidified residue, and the mixture was heated to 45° C., at which temperature a slightly turbid solution was formed. The solution was cooled, seeded at 40° C., and precipitate was formed by stirring for 25 minutes at 40-36° C. After cooling and stirring for 40 minutes at ambient temperature, the precipitate of heavy crystals was isolated by filtration, and the filter cake was washed with heptane (1000 mL). The wet filter cake (914 g) was dried overnight at ambient temperature under reduced pressure (<1 mBar) to give 635 g (100%) of 2,2'-(tert-butoxycarbonylazanediyl)bis(ethane-2,1-diyl) ditetradecanoate (HEDC-amine-IN) TFA salt as white crystals.

Preparation of 2,2'-(2-(dimethylamino)acety-lazanediyl)bis(ethane-2,1-diyl) ditetradeca-noate (HEDC-DiMeGly-IN)

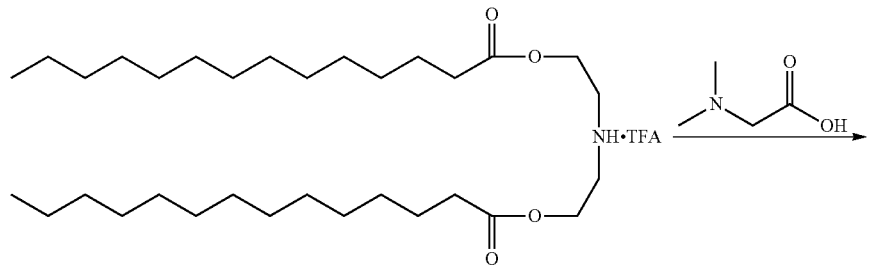

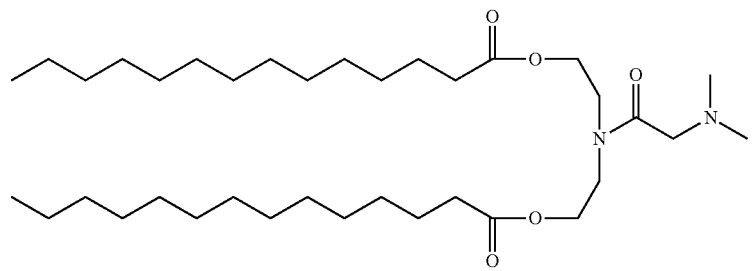

N,N-dimethylglycine (56.6 g, 548 mmol), 1-hydroxybenzotriazole (HOBt) hydrate (83.9 g, 548 mmol) and N-(3-dimethylaminopropyl)-N'-ethylcarbodiimide hydrochloride (EDC) (105 g, 548 mmol) were added to dimethylformamide (DMF) (3.5 L), and the mixture was stirred at ambient temperature for one hour. A clear solution was formed. HEDC-amine-IN TFA salt (270 g, 442 mmol) was mixed with DCM (1.15 L) and 6% NaHCO₃ (1.15 L). The separated organic phase with the free amine was added to the coupling mixture in DMF, and a precipitation as well as a temperature increase of about 9° C. was observed. Triethylamine (47.0 g, 464 mmol) was added, and the reaction mixture was stirred at 25-30° C. for five hours. TLC indicated incomplete conversion, and more EDC (29.5 g, 154 mmol) was added. Having stirred overnight at ambient temperature, a clear solution was observed, and TLC now indicated full conversion. The reaction mixture was mixed with DCM (2.3 L) and 2% NaHCO₃ (7 L). The organic phase was washed twice with 1.25% sodium chloride (5 L each) and dried with anhydrous magnesium sulphate (186 g). The filtrate was evaporated at 50° C. and 30 mBar to give 253 g of crude oil. The crude material was loaded to a column packed with 2.6 kg of Silica Gel 60 (40-63p). The product was eluted with toluene:ethyl acetate (8:2) (4 L), and followed with ethyl acetate:methanol (1:1) (5 L). The product containing fractions (3.5-8 L) was evaporated (50° C./250-20 mBar) to give 208 g (66%) of 2,2'-(2-(dimethylamino) acetylazanediyl)bis(ethane-2,1-diyl) ditetradecanoate (HEDC-DiMeGly-IN) as an oil.

Preparation of HEDC: 2-(bis(2-(tetradecanoyloxy) ethyl)amino)-N-(2-hydroxyethyl)-N,N-dimethyl-2-oxethanaminium bromide

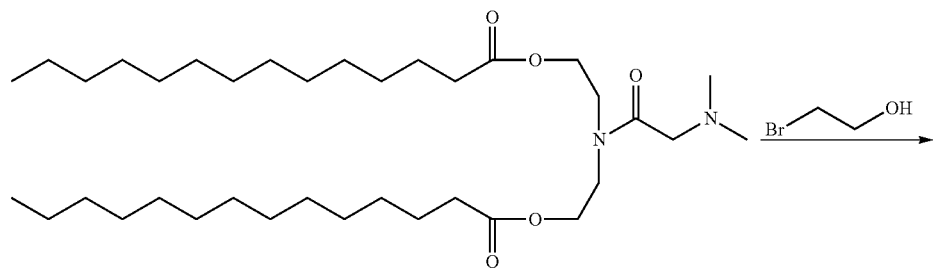

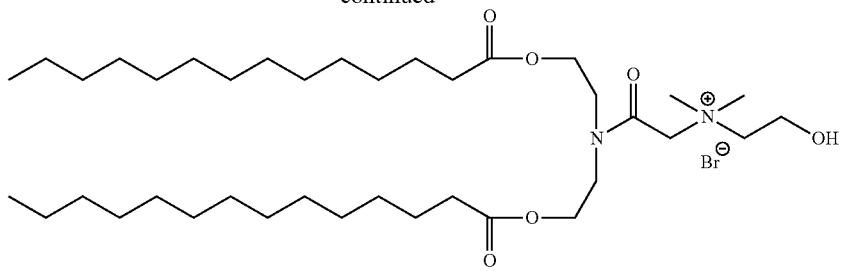

A mixture of HEDC-DiMeGly-IN (206 g, 337 mmol) and 2-bromoethanol (274 g, 2.19 mol) was stirred at 80° C. for two hours. HPLC indicated 8.1% of unreacted dimethylglycin-intermediate. After another 40 minutes at 80° C., HPLC indicated 7.8% of unreacted dimethylglycin intermediate. Ethyl acetate (2 L) at 65° C. was added. A blank filtration of the hot solution was washed with hot ethyl acetate (0.5 L). The combined filtrates were cooled to 0° C., and crystallization was initiated by seeding. The product suspension was cooled slowly and stirred at −16 to −18° C. for 40 minutes. The precipitate was isolated by filtration, and the filter cake was washed with cold ethyl acetate (200 mL). Drying overnight (20° C./<1 mBar) gave 211 g of crude material. The material was recrystallized from a mixture of ethyl acetate (2.1 L) and ethanol (105 mL) by heating to 35° C. and seeding at 25° C. The precipitate was isolated at 10° C., washed with cold ethyl acetate (300 mL) and dried (20° C./<1 mBar) overnight to give 161 g (66%) of 2-(bis(2-(tetradecanoyloxy)ethyl)amino)-N-(2-hydroxyethyl)-N,N-dimethyl-2-oxoethanaminium bromide (HEDC). HPLC indicated 99.5% purity. QTOF MS ESI+: m/z 655.6 (M+H).

Example 2: Preparation of 2-(bis(3-(tetradecanoyloxy)propyl)amino)-N-(2-hydroxyethyl)-N,N-dimethyl-2-oxo-ethanaminium bromide (Pr-HEDC)

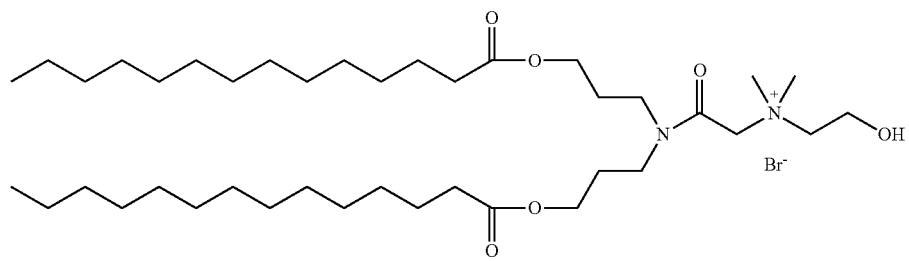

Preparation of 3,3'-azanediylbis(propan-1-ol)

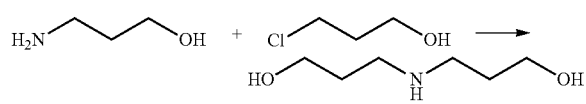

A mixture of 3-amino-1-propanol (14.5 mL, 19.0 mmol), 1-chloro-3-hydroxy propane (8 mL, 95.6 mmol) and water (H₂O) (~50 mL) was refluxed over 24 hours. Potassium hydroxide (5.40 g) was then added. After dissolution, the whole of the water was evaporated to leave viscous oil and large quantities of potassium chloride. These were filtered and washed with dry acetone and dichloromethane. The organic phase was dried over sodium sulfate (Na₂SO₄), filtered, and concentrated. Product was then purified via silica gel chromatography with a DCM/methanol (MeOH) gradient to yield 12.5 g 3,3'-azanediylbis(propan-1-ol).

Preparation of tert-butyl bis(3-hydroxypropyl)carbamate

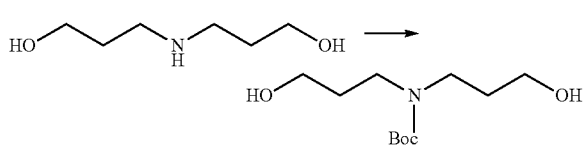

3,3'-Azanediylbis(propan-1-ol) (12.5 g, 95.4 mmol) was diluted in DCM (25 mL). A solution of di-tert-butyl dicarbonate (26 g, 119.25 mmol) in DCM (25 mL) was slowly added while stirring under a blanket of argon (Ar) gas. The reaction was stirred overnight. The reaction mixture was concentrated. Purification by silica gel chromatography with a DCM/MeOH gradient yielded tert-butyl bis(3-hydroxypropyl)carbamate.

Preparation of ((tert-butoxycarbonyl)azanediyl)bis(propane-3,1-diyl) ditetradecanoate

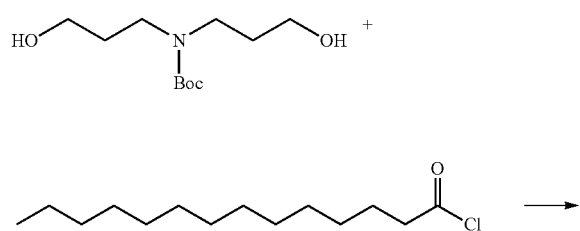

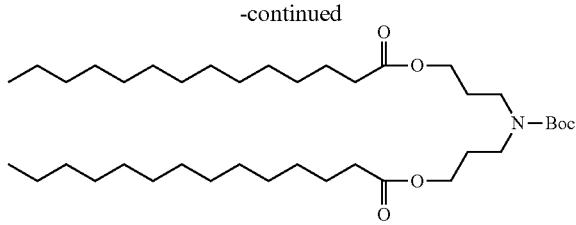

tert-Butyl bis(3-hydroxypropyl)carbamate (4.00 g, 17.3 mmol), triethylamine (4.80 ml, 34.6 mmol) and 4-dimethylaminopyridine (529 mg, 4.33 mmol) were dissolved in chloroform (50 mL). While being stirred in an ice-bath, a solution of myristoyl chloride was added in ~15 min. The addition was carried out in such a way that the temperature of the reaction did not exceed 30° C. The reaction was stirred at room temperature overnight. MeOH (50 mL) and 0.9% saline solution (50 mL) was added to quench the reaction. The organic layer was separated and washed with 1M NaHCO$_3$. Solvent was dried with Na$_2$SO$_4$, filtered, and concentrated in vacuo to yield ((tert-butoxycarbonyl)azanediyl)bis(propane-3,1-diyl) ditetradecanoate as an oil.

Preparation of azanediylbis(propane-3,1-diyl) ditetradecanoate TFA Salt

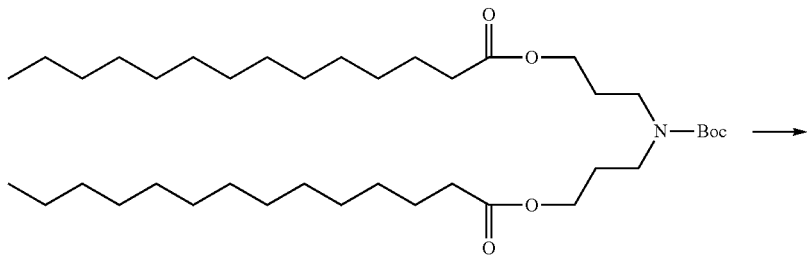

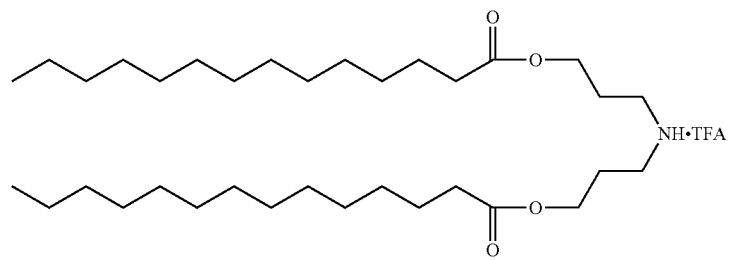

((tert-butoxycarbonyl)azanediyl)bis(propane-3,1-diyl) ditetradecanoate (11.3 g, 17.3 mmol) was dissolved in TFA/chloroform CHCl$_3$ (1:1, 20 mL) and the mixture was stirred at room temperature for 15 minutes. The mixture was then concentrated in vacuo. The residue was then dissolved in DCM and washed with water, dried with Na$_2$SO$_4$, and concentrated in vacuo. Purification by silica gel chromatography with a DCM/MeOH gradient yielded azanediylbis(propane-3,1-diyl) ditetradecanoate TFA salt (750 mg).

Preparation of ((2-(dimethylamino)acetyl)azanediyl)bis(propane-3,1-diyl) ditetradecanoate

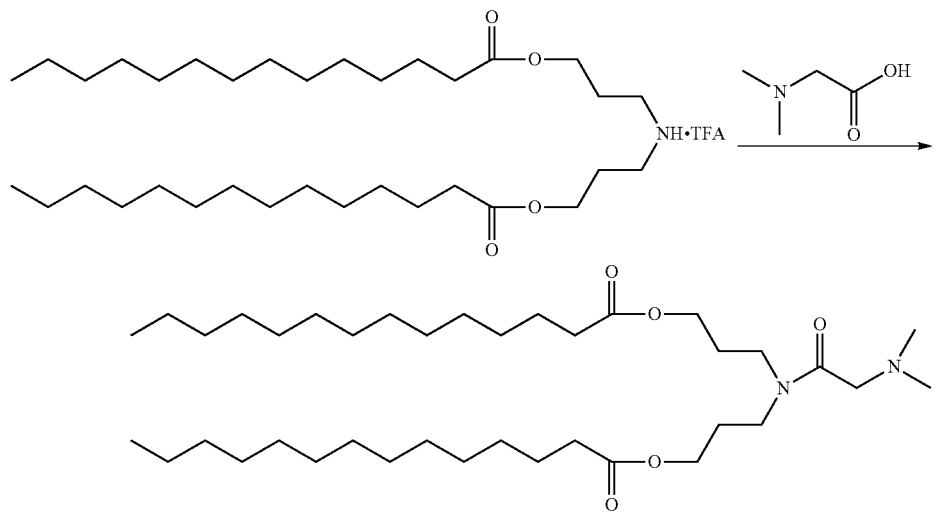

Azanediylbis(propane-3,1-diyl) ditetradecanoate TFA salt (750 mg, 1.35 mmol) was diluted with DCM (5 mL) and added to a pre-activated mixture of N,N-dimethylglycine (154 mg, 1.49 mmol), 1-[bis(dimethylamino)methylene]-1H-1,2,3-triazolo[4,5-b]pyridinium 3-oxide hexaflourophosphat (HATU) (616 mg, 1.62 mmol) and N,N-diisopropylethylamine (DIEA) (495 µL, 2.84 mmol) in DCM (5 mL). Product was flushed with argon and stirred at room temperature overnight, and then concentrated. Purification by silica gel chromatography with a DCM/MeOH gradient yielded 465 mg ((2-(dimethylamino)acetyl)azanediyl)bis(propane-3,1-diyl)ditetradecanoate.

Preparation of Pr-HEDC: 2-(bis(3-(tetradecanoyloxy)propyl)amino)-N-(2-hydroxyethyl)-N,N-dimethyl-2-oxoethanaminium bromide

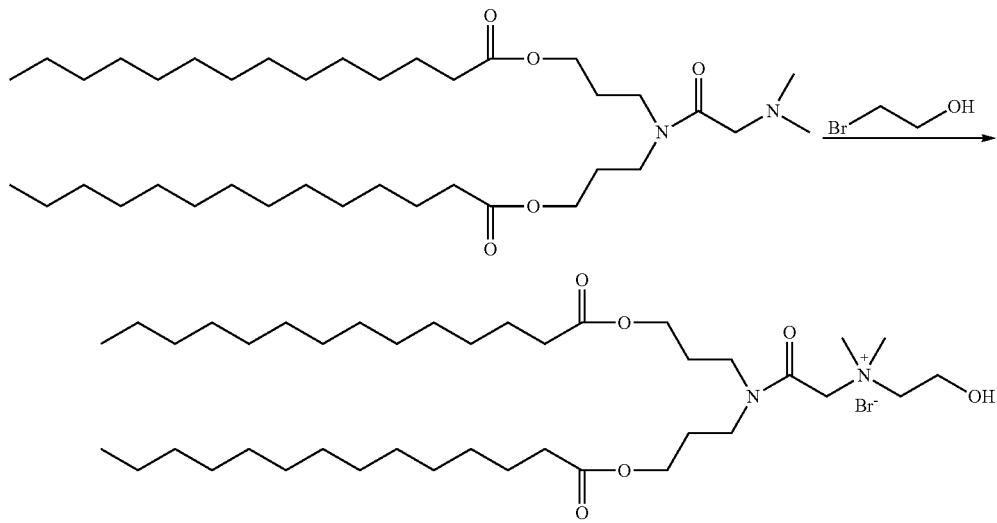

In a sealed system, ((2-(dimethylamino)acetyl)azanediyl)bis(propane-3,1-diyl) ditetradecanoate (246 mg, 0.385 mmol) was dissolved in acetonitrile (ACN) (10 mL), and 2-bromoethanol (500 µL) was added. The reaction vessel was flushed with inert gas and then sealed. The mixture was heated to 80° C., stirred overnight, and then cooled and concentrated in vacuo. Purification by silica gel chromatography with a DCM/MeOH gradient yielded 99 mg 2-(bis(3-(tetradecanoyloxy)propyl)amino)-N-(2-hydroxyethyl)-N,N-dimethyl-2-oxoethanaminium bromide. QTOF MS ESI+: m/z 683.6 (M+H).

Example 3: Preparation of 2-(bis(3-(oleoyloxy)propyl)amino)-N-(2-hydroxyethyl)-N,N-dimethyl-2-oxoethanaminium bromide (Pr-HE-DODC)

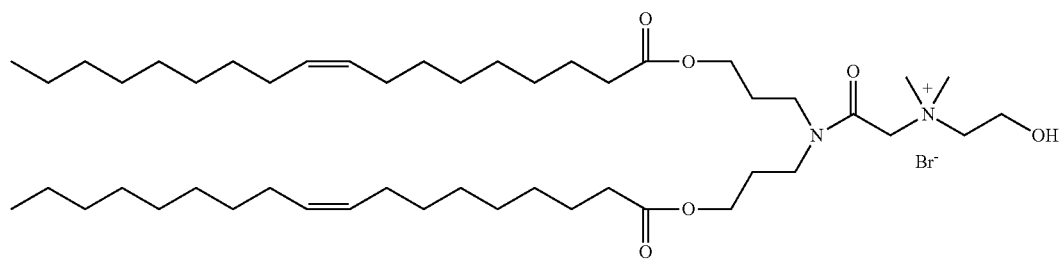

Preparation of (Z)-((tert-butoxycarbonyl)azanediyl)bis(propane-3,1-diyl) dioleate

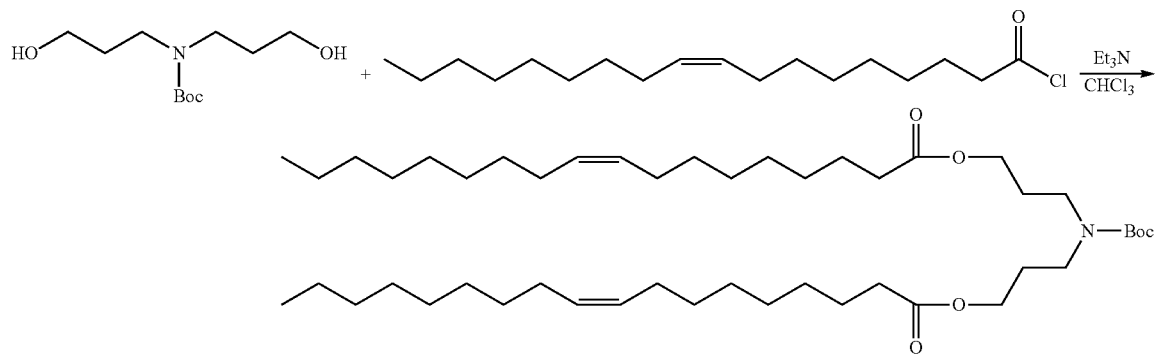

tert-Butyl bis(3-hydroxypropyl)carbamate (synthesized as described above), triethylamine and N,N-4-dimethylaminopyridine (DMAP) were dissolved in chloroform. While stirring in an ice-bath, a solution of oleoyl chloride was added in 15 minutes. The temperature of the reaction during addition did not exceed 30° C. The reaction was stirred at room temperature overnight. MeOH (50 mL) and 0.9% saline solution (50 mL) were added to quench the reaction. The organic layer was separated and washed with 1 M NaHCO$_3$. Solvent was dried with Na$_2$SO$_4$, filtered and concentrated to yield an oil. The product (Z)-((tert-butoxycarbonyl)azanediyl)bis(propane-3,1-diyl) dioleate was used without further purification.

Preparation of (Z)-azanediylbis(propane-3,1-diyl) dioleate TFA Salt

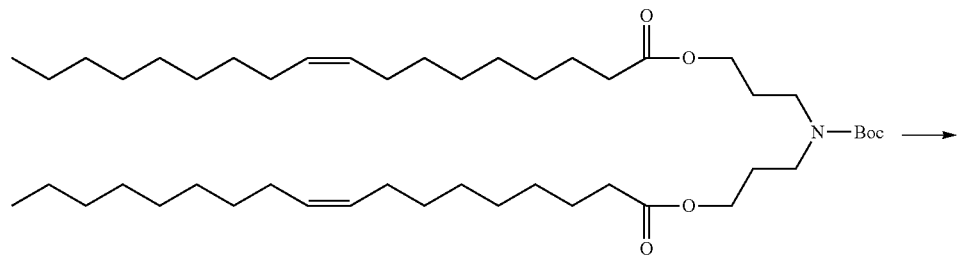

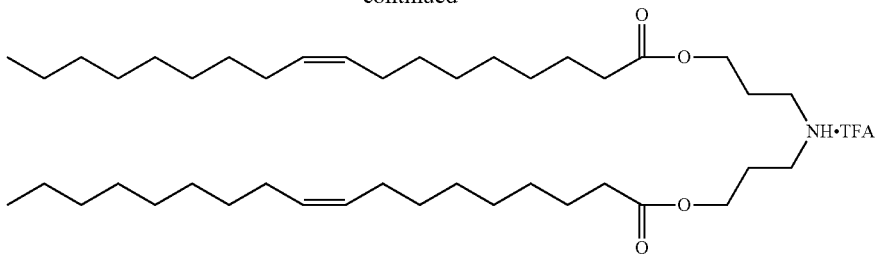

(Z)-((tert-Butoxycarbonyl)azanediyl)bis(propane-3,1-diyl) dioleate (13.2 g, 17.3 mmol) was dissolved in TFA/CHCl₃ (1:1, 20 mL) and the mixture was stirred at room temperature for 15 minutes. The mixture was then concentrated in vacuo. The residue was dissolved in DCM and washed with water, dried with Na₂SO₄ and concentrated. Purification by silica gel chromatography with a DCM/MeOH gradient yielded (Z)-azanediylbis(propane-3,1-diyl) dioleate TFA salt (750 mg).

Preparation of (Z)-((2-(dimethylamino)acetyl) azanediyl)bis(propane-3,1-diyl) dioleate

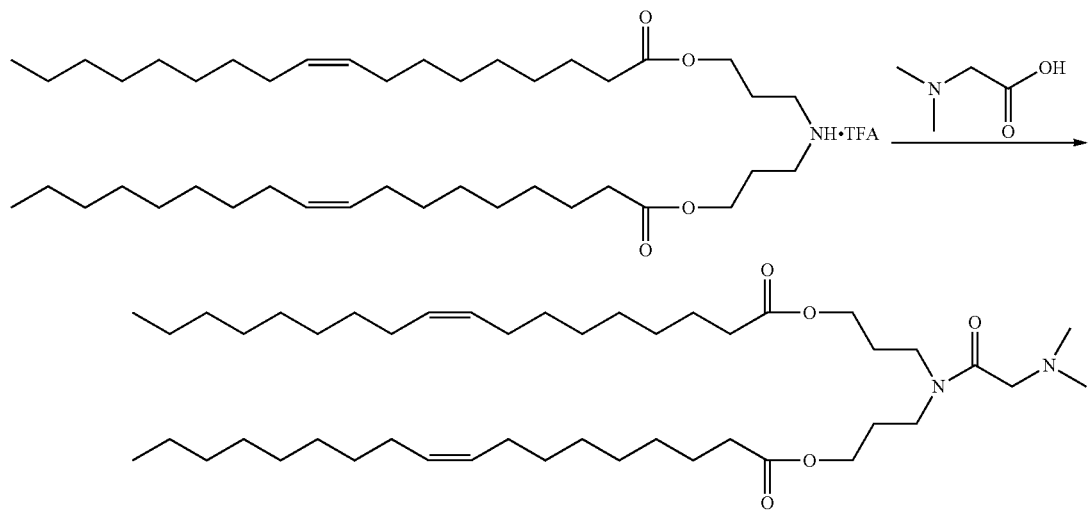

(Z)-azanediylbis(propane-3,1-diyl) dioleate TFA salt (750 mg, 1.13 mmol) was diluted with DCM (5 mL) and added to a pre-activated mixture of N,N-dimethylglycine (128 mg, 1.24 mmol), 1-[bis(dimethylamino)methylene]-1H-1,2,3-triazolo[4,5-b]pyridinium 3-oxide hexafluorophosphate, (HATU) (517 mg, 1.36 mmol) and N,N-diisopropylethylamine (DIEA) (413 µL, 2.37 mmol) in DCM (5 mL). The mixture was flushed with argon and stirred at room temperature overnight. The reaction mixture was concentrated, and subjected to silica gel chromatography with a DCM/MeOH gradient to yield (Z)-((2-(dimethylamino)acetyl) azanediyl)bis(propane-3,1-diyl) dioleate.

Preparation of Pr-HE-DODC: 2-(bis(3-(oleoyloxy) propyl)amino)-N-(2-hydroxyethyl)-N,N-dimethyl-2-oxoethanaminium bromide

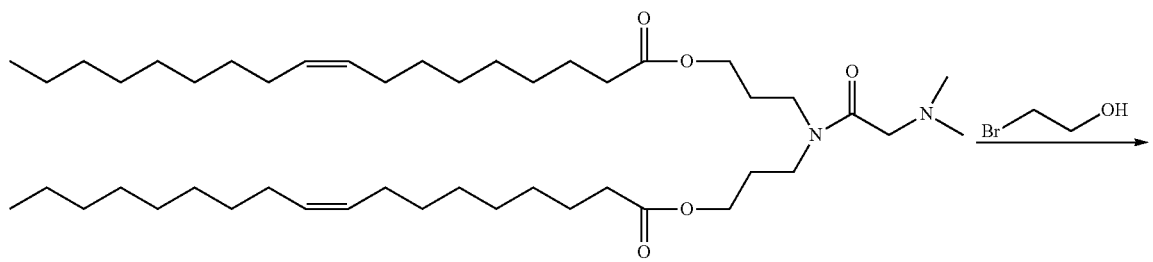

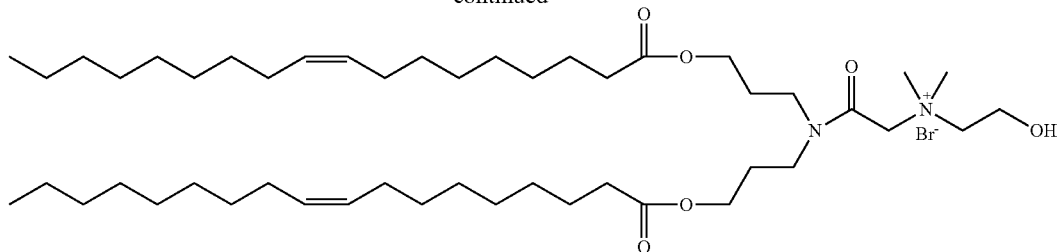

In a sealed system, (Z)-((2-(dimethylamino)acetyl)azanediyl)bis(propane-3,1-diyl) dioleate (269 mg, 0.360 mmol) was dissolved in ACN (10 mL) and 2-bromoethanol (200 µL) was added. The reaction vessel was flushed with inert gas and then sealed. Reaction was heated to 80° C. and stirred overnight. The reaction mixture was cooled and concentrated. Purification by silica gel chromatography with a DCM/MeOH gradient yielded 2-(bis(3-(oleoyloxy)propyl)amino)-N-(2-hydroxyethyl)-N,N-dimethyl-2-oxoethanaminium bromide (129 mg). QTOF MS ESI+: m/z 791.7 (M+H).

Example 4: Preparation of 3-(bis(2-(tetradecanoyloxy)ethyl)amino)-N-(2-hydroxyethyl)-N,N-dimethyl-3-oxopro-pan-1-aminium bromide (HE-Et-DC)

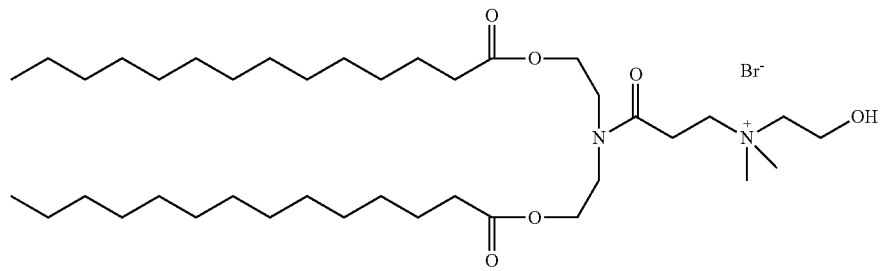

Preparation of ((3-(dimethylamino)propanoyl)azanediyl)bis(ethane-2,1-diyl) ditetradeca-noate

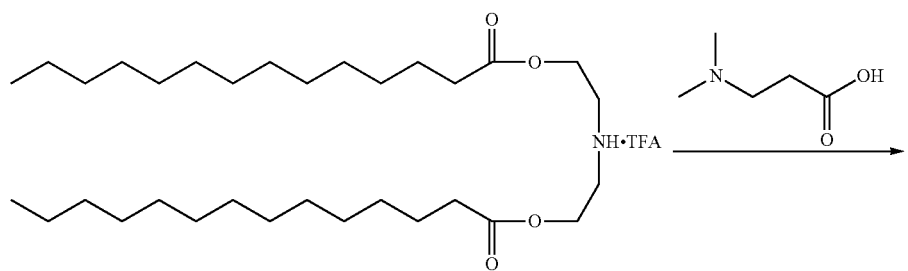

-continued

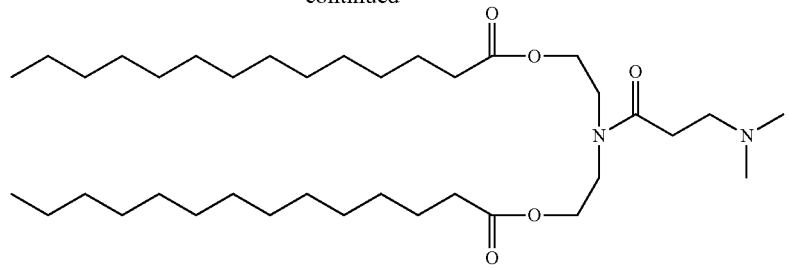

Synthesis of azanediylbis(ethane-2,1-diyl) ditetradecanoate TFA salt previously described. Azanediylbis(ethane-2,1-diyl) ditetradecanoate TFA salt (1.5 g, 2.85 mmol) was diluted with DCM (10 mL) and added to a pre-activated mixture of 3-(dimethylamino)propionic acid HCl salt (482 mg, 3.14 mmol), HATU (1.30 g, 3.42 mmol) and DIEA (1.04 mL, 5.98 mmol) in DCM (10 mL). The round-bottomed flask was flushed with argon and the reaction mixture was stirred at room temperature overnight. The reaction mixture was concentrated. Purification by silica gel chromatography with a DCM/MeOH gradient yielded ((3-(dimethylamino)propanoyl)azanediyl)bis(ethane-2,1-diyl) ditetradecanoate.

Preparation of HE-Et-DC: 3-(bis(2-(tetradecanoyloxy)ethyl)amino)-N-(2-hydroxyethyl)-N,N-dimethyl-3-oxopropan-1-aminium bromide

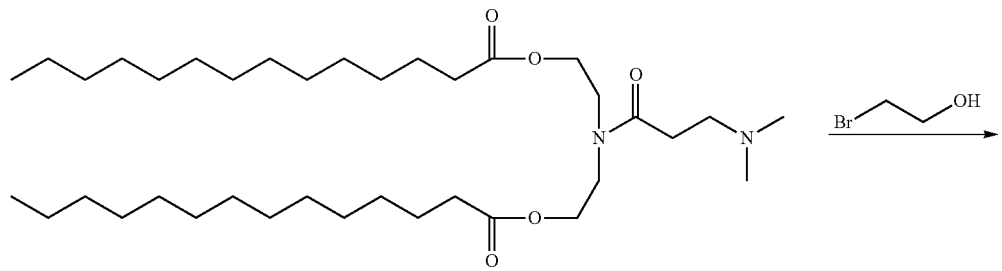

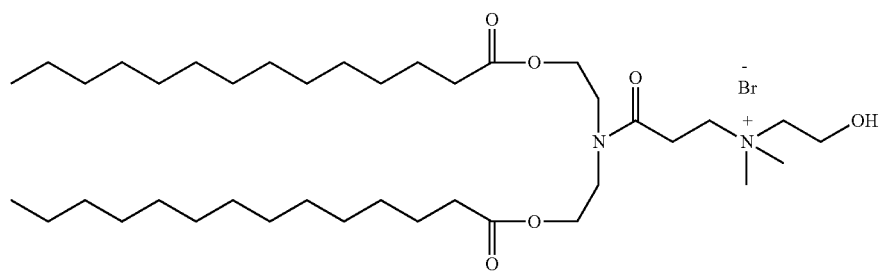

In a sealed system, ((3-(dimethylamino)propanoyl)azanediyl)bis(ethane-2,1-diyl) ditetradecanoate (606 mg, 0.970 mmol) was dissolved in ACN (10 mL) and 2-bromoethanol (500 μL) was added. The reaction vessel was flushed with inert gas and then sealed. Reaction was heated to 80° C. and stirred overnight, then cooled and concentrated. Purification by silica gel chromatography with a DCM/MeOH gradient yielded 3-(bis(2-(tetradecanoyloxy)ethyl)amino)-N-(2-hydroxyethyl)-N,N-dimethyl-3-oxopropan-1-aminium bromide (80 mg). QTOF MS ESI+: m/z 669.6 (M+H).

Example 5: Preparation of 3-(bis(2-(oleoyloxy)ethyl)amino)-N-(2-hydroxyethyl)-N,N-dimethyl-3-oxopropan-1-aminium bromide (HE-Et-DODC)

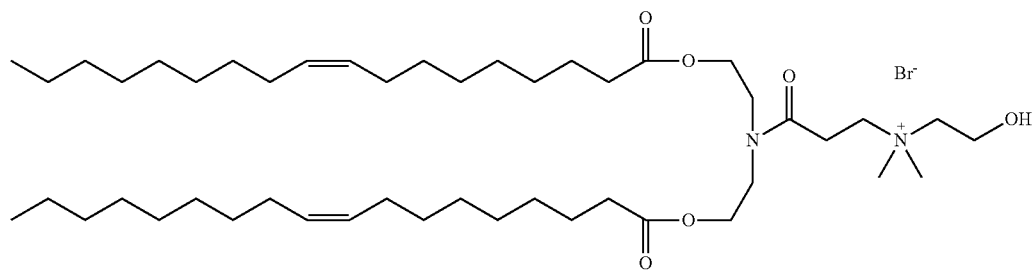

Preparation of (Z)-((tert-butoxycarbonyl)azanediyl)bis(ethane-2,1-diyl) dioleate

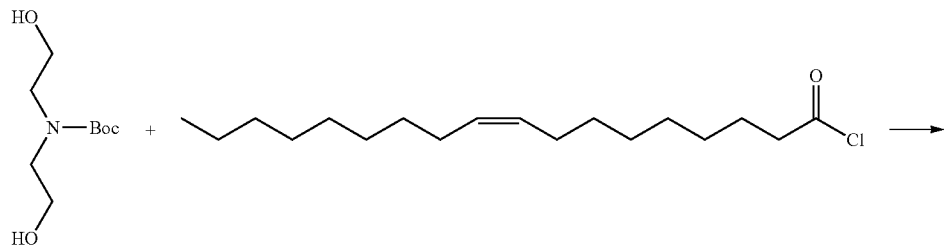

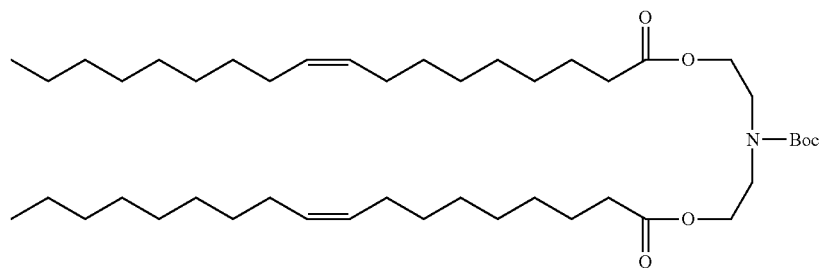

N-tert-butoxycarbonyl (N-Boc) diethanolamine) (17.81 g, 0.087 mole), triethylamine (24.4 ml, 0.176 mole) and 4-(dimethylamino)pyridine (2.76 ml, 1.3 g, 0.023 mole) were dissolved in 350 ml of chloroform. While being stirred, a solution of oleoyl chloride (61.6 g, 0.174 mole) in 100 ml of chloroform was added in 10 minutes. (Alternatively, the chloroform solution of N-Boc diethanolamine was immersed in an ice/water bath while oleoyl chloride was added.) The temperature of the reaction mixture did not exceed 50° C. during the addition. The reaction mixture was stirred at room temperature for 2 hours. A mixture of 200 ml of methanol and 200 ml of 0.9% saline was added to quench the reaction. The organic layer was separated and was washed with 2×100 ml of dilute aqueous $NaHCO_3$. The solvent was removed to afford 59.5 g of crude product as pale yellow oil (59.5 g, 0.081 mole, 100% yield). This material was used for the next step without further purification. 1H NMR (400 MHz, CDCl3) 0.87 (t, 6H, CH3), 1.20-1.40 (m, 40H, CH2), 1.45 (s, 9H, tBu CH3), 1.59 (m, 4H, CH2CH2C(=O)), 2.00 (m, 8H, CH2CH=CH), 2.33 (t, 4H, CH2C(=O)), 3.48 (m, 4H, NCH2CH2O), 4.18 (m, 4H, NCH2CH2O), 5.33 (m, 4H, CH=CH).

Preparation of (Z)-azanediylbis(ethane-2,1-diyl) dioleate TFA Salt

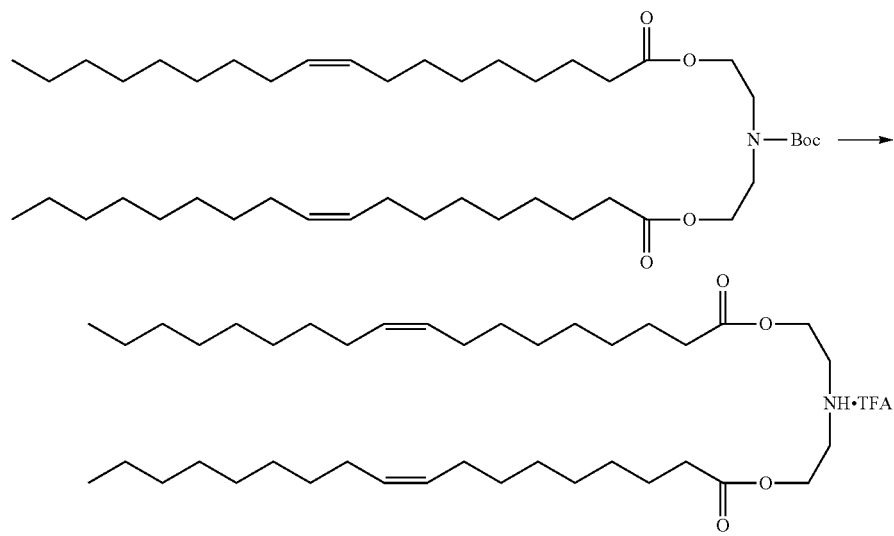

The (Z)-((tert-butoxycarbonyl)azanediyl)bis(ethane-2,1-diyl) dioleate (59.5 g, 0.081 mole) was treated twice with 100 ml trifluoroacetic acid (100 ml, 1.35 mole) and 100 ml of chloroform. Each consisted of stirring at room temperature for ten minutes, and the solvent was removed by rotary evaporation at the end of each treatment. After the second treatment, the reaction mixture was concentrated by rotary evaporation. The residue was dissolved in 200 ml of methylene chloride and the mixture had been washed with 100 ml of water twice. The residue was purified by silica gel chromatography using a mixture of methanol and methylene chloride as eluent to yield 44 g of (Z)-azanediylbis(ethane-2,1-diyl) dioleate TFA salt (44.0 g). 1H NMR (400 MHz, CDCl3) 0.87 (t, 6H, CH3), 1.20-1.40 (m, 40H, CH2), 1.59 (m, 4H, CH2CH2C(=O)), 2.00 (m, 8H, CH2CH=CH), 2.33 (t, 4H, CH2C(=O)), 3.31 (m, 4H, NCH2CH2O), 4.38 (m, 4H, NCH2CH2O), 5.33 (m, 4H, CH=CH).

Preparation of (((Z)-((3-(dimethylamino)propanoyl) azanediyl)bis(ethane-2,1-diyl) dioleate

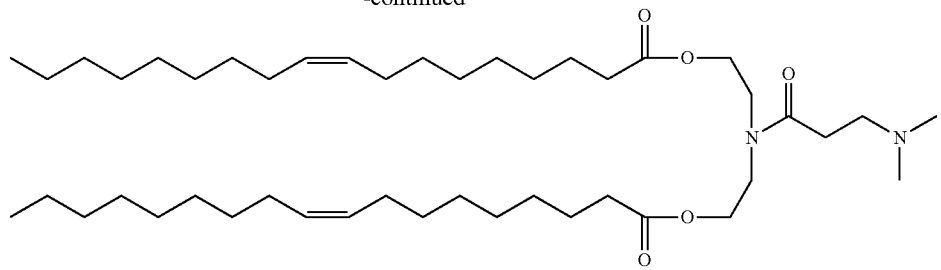

(Z)-azanediylbis(ethane-2,1-diyl) dioleate TFA salt (1.50 g, 2.37 mmol) was diluted with DCM (10 mL) and added to a pre-activated mixture of 3-(dimethylamino)propionic acid HCl salt (383 mg, 2.49 mmol), HATU (1034 mg, 2.72 mmol) and DIEA (831 µL, 4.77 mmol) in DCM (10 mL). The reaction mixture was flushed with argon and stirred at room temperature overnight. The reaction mixture was concentrated. Purification by silica gel chromatography with a DCM/MeOH gradient yielded (Z)-((3-(dimethylamino)propanoyl)azanediyl)bis(ethane-2,1-diyl) dioleate.

Preparation of HE-Et-DODC: 3-(bis(2-(oleoyloxy)ethyl)amino)-N-(2-hydroxyethyl)-N,N-dimethyl-3-oxo-propan-1-aminium bromide

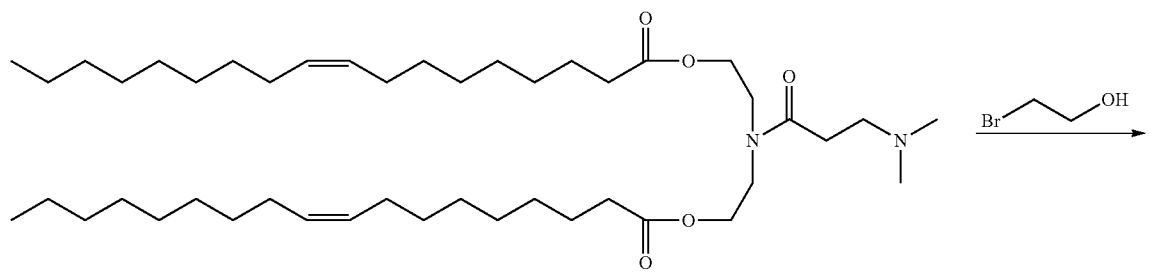

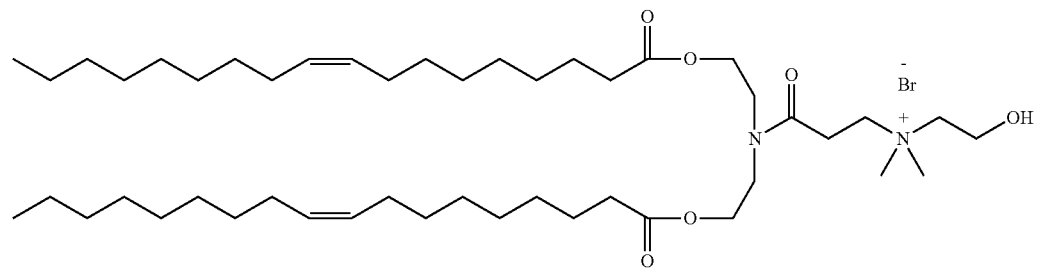

In a sealed system, (((Z)-((3-(dimethylamino)propanoyl)azanediyl)bis(ethane-2,1-diyl) dioleate (588 mg, 0.802 mmol) was dissolved in ACN (10 mL) and 2-bromoethanol (200 μL) was added. The reaction vessel was flushed with inert gas and then sealed. Reaction was heated to 80° C. and stirred overnight, then cooled and concentrated in vacuo. Purification by silica gel chromatography with a DCM/MeOH gradient yielded 3-(bis(2-(oleoyloxy)ethyl)amino)-N-(2-hydroxyethyl)-N,N-dimethyl-3-oxopropan-1-aminium bromide (160 mg). QTOF MS ESI+: m/z 764.3 (M+H).

Example 6: Preparation of 4-(bis(2-(tetradecanoyloxy)ethyl)amino)-N-(2-hydroxyethyl)-N,N-dimethyl-4-oxobutan-1-aminium bromide (HE-Pr-DC)

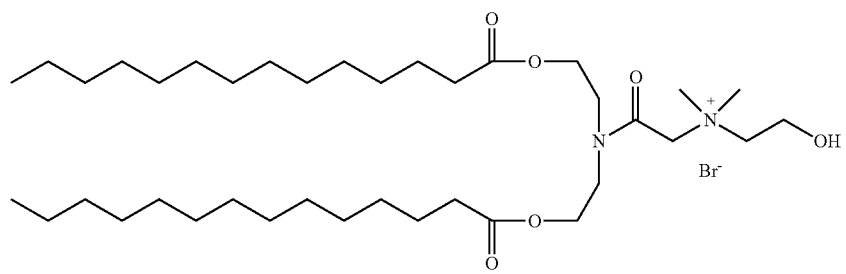

Preparation of ((4-(dimethylamino)butanoyl)azanediyl)bis(ethane-2,1-diyl) ditetra-decanoate

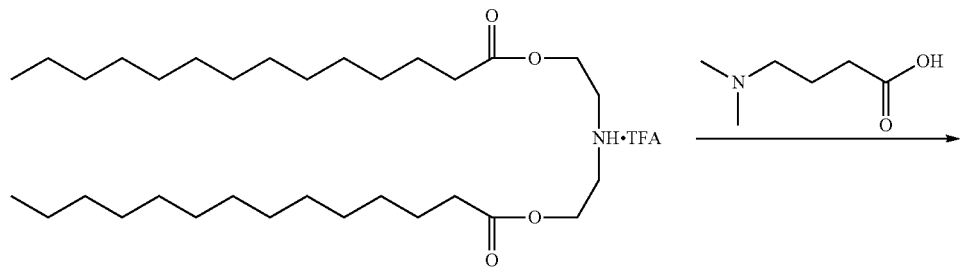

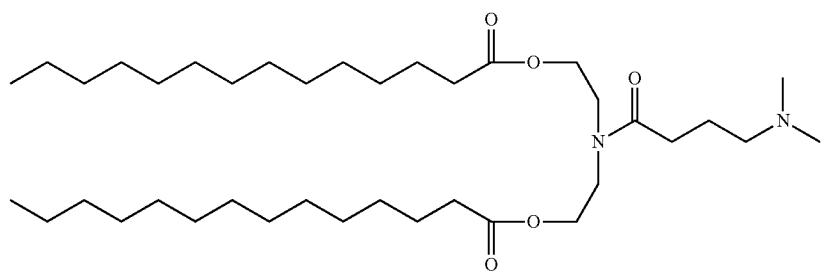

Synthesis of azanediylbis(ethane-2,1-diyl) ditetradecanoate TFA salt previously described. Azanediylbis(ethane-2,1-diyl) ditetradecanoate TFA salt (1.00 g, 1.90 mmol) was diluted with DCM (5 mL) and added to a pre-activated mixture of 4-(dimethylamino) butyric acid HCl salt (382 mg, 2.28 mmol), HATU (867 mg, 2.28 mmol) and DIEA (728 μL, 4.18 mmol) in DCM (5 mL). The flask was flushed with argon and the reaction mixture was stirred at room temperature overnight, then concentrated. Purification by silica gel chromatography with a DCM/MeOH gradient yielded ((4-(dimethylamino)butanoyl)azanediyl)bis(ethane-2,1-diyl) ditetradecanoate.

Preparation of HE-Pr-DC: 4-(bis(2-(tetradecanoyloxy)ethyl)amino)-N-(2-hydroxyethyl)-N,N-dimethyl-4-oxobutan-1-aminium bromide In a sealed system, ((4-(dimethylamino)butanoyl)azanediyl)bis(ethane-2,1-diyl) ditetradecanoate (300 mg, 0.469 mmol) was dissolved in ACN (5 mL) and 2-bromoethanol (500 μL) was added. The reaction vessel was flushed with inert gas and then sealed. Reaction was heated to 80° C. and stirred overnight, then concentrated. Purification by silica gel chromatography with a DCM/MeOH gradient yielded 4-(bis(2-(tetradecanoyloxy)ethyl)amino)-N-(2-hydroxyethyl)-N,N-dimethyl-4-oxobutan-1-aminium bromide (140 mg). LCMS ESI+: m/z 684.4 (M+H).

Example 7: Preparation of 4-(bis(2-(oleoyloxy)ethyl)amino)-N-(2-hydroxyethyl)-N,N-dimethyl-4-oxobutan-1-aminium bromide (HE-Pr-DODC)

Preparation of (Z)-((4-(dimethylamino)butanoyl)azanediyl)bis(ethane-2,1-diyl) dioleate

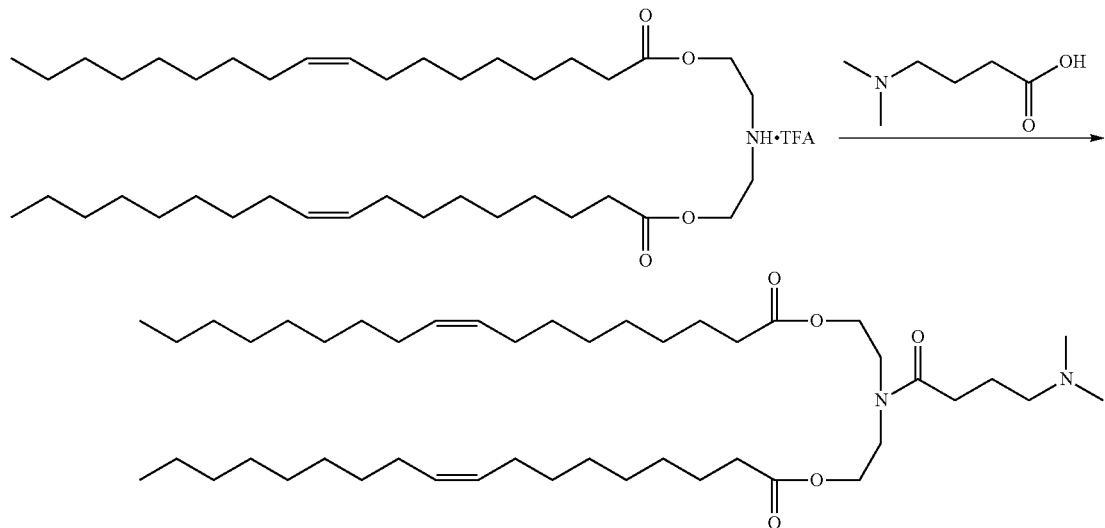

Synthesis of (Z)-azanediylbis(ethane-2,1-diyl) dioleate TFA salt described above (1.00 g, 1.58 mmol) was diluted with DCM (5 mL) and added to a pre-activated mixture of 4-(dimethylamino) butyric acid HCl salt (317 mg, 1.89 mmol), HATU (719 mg, 1.89 mmol) and DIEA (606 μL, 3.48 mmol) in DCM (5 mL). The flask was flushed with argon and the reaction mixture stirred at room temperature overnight, then concentrated. Purification by silica gel chromatography with a DCM/MeOH gradient yielded (Z)-((4-(dimethylamino)butanoyl)azanediyl)bis(ethane-2,1-diyl) dioleate.

Preparation of HE-Pr-DODC: 4-(bis(2-(oleoyloxy)ethyl)amino)-N-(2-hydroxyethyl)-N,N-dimethyl-4-oxobutan-1-aminium bromide

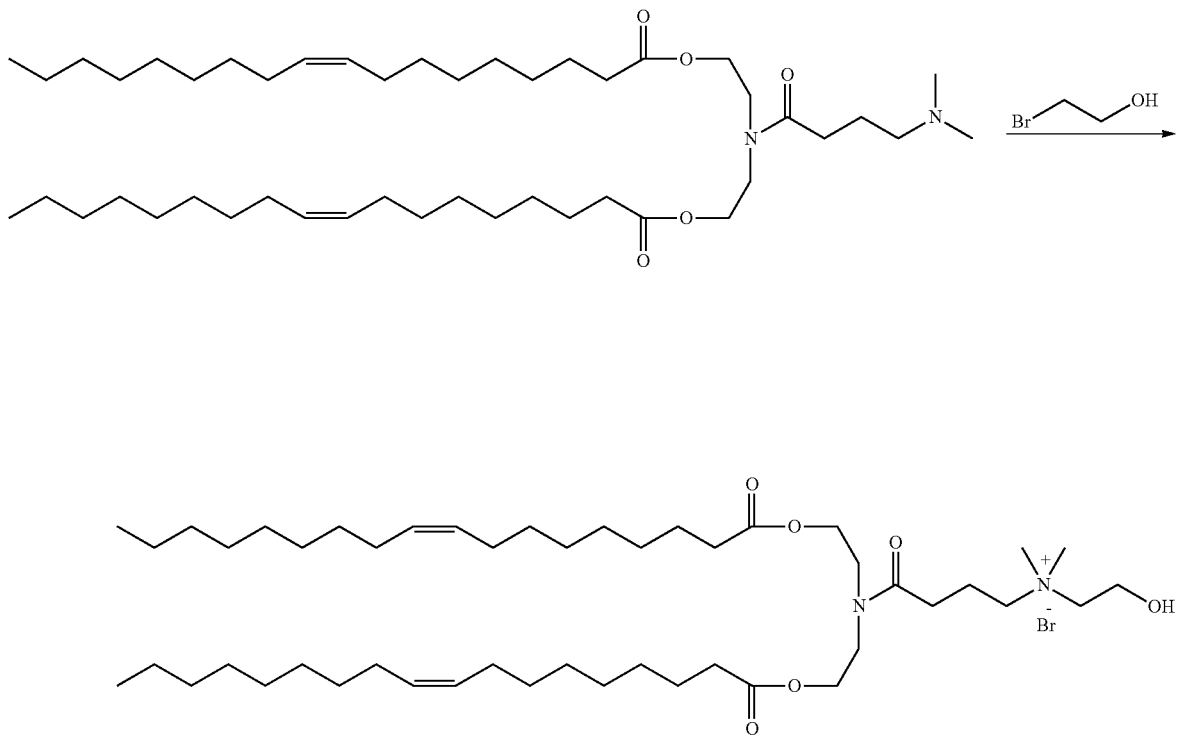

In a sealed system, ((4-(dimethylamino)butanoyl)azanediyl)bis(ethane-2,1-diyl) ditetradecanoate (400 mg, 0.535 mmol) was dissolved in ACN (5 mL) and 2-bromoethanol (500 µL) was added. The reaction vessel was flushed with inert gas and then sealed. Reaction was heated to 80° C. and stirred overnight, then concentrated. Purification by silica gel chromatography with DCM/MeOH gradient yielded 4-(bis(2-(oleoyloxy)ethyl)amino)-N-(2-hydroxyethyl)-N,N-dimethyl-4-oxobutan-1-aminium bromide (255 mg). LCMS ESI+: m/z 792.5 (M+H).

Example 8: Preparation of 2-(bis(2-(oleoyloxy)ethyl)amino)-N,N-bis(2-hydroxyethyl)-N-methyl-2-oxoethanaminium bromide (HE2DODC)

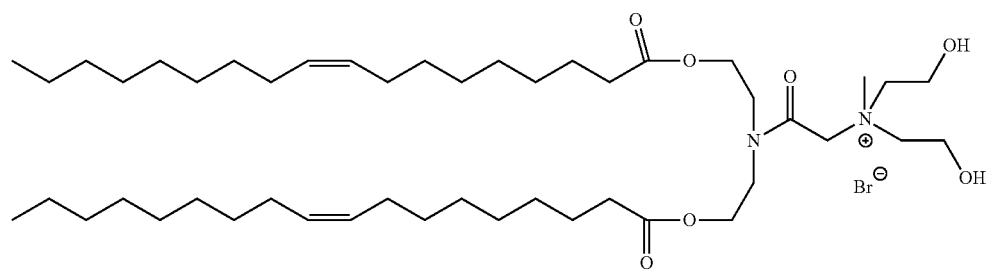

Preparation of (Z)-((2-bromoacetyl)azanediyl)bis(ethane-2,1-diyl) dioleate

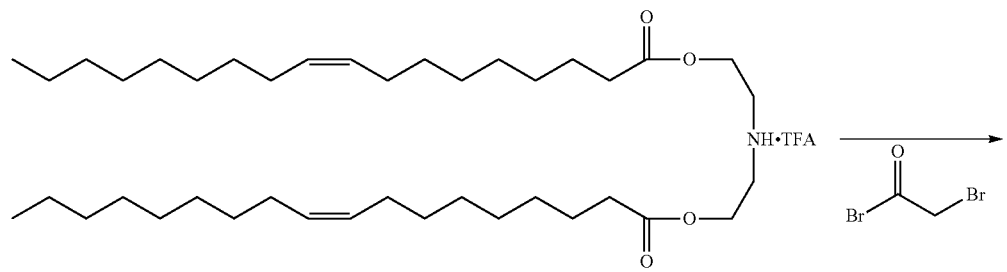

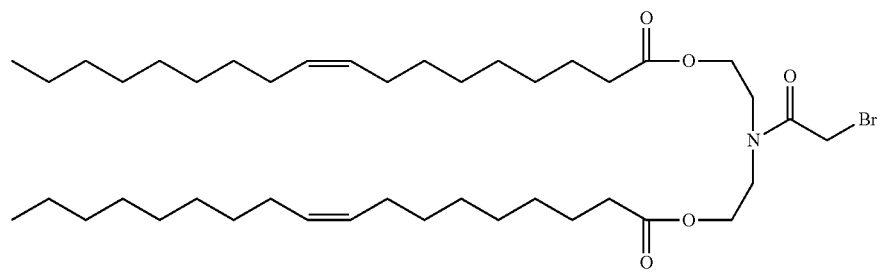

Synthesis of (Z)-azanediylbis(ethane-2,1-diyl) dioleate TFA salt previously described. (Z)-azanediylbis(ethane-2,1-diyl) dioleate TFA salt (1.50 g, 2.34 mmol) was dissolved in DCM (20 mL) and placed in an ice-bath. Bromoacetyl bromide (214 µL, 2.46 mmol) was added followed by triethylamine (685 µL, 4.91 mmol). The ice-bath was removed and the reaction was stirred overnight at room temperature under inert gas, then diluted with DCM to 100 mL, and washed with a 1M HCl (75 mL), H₂O (75 mL), saturated NaHCO₃ solution (75 mL) and saturated brine solution (75 mL). All aqueous washes were back extracted with DCM (25 mL). Dried organics with magnesium sulfate (MgSO₄), filtered and concentrated in vacuo. Purification by silica gel chromatography with ethyl acetate yielded (Z)-((2-bromoacetyl)azanediyl)bis(ethane-2,1-diyl) dioleate (1.22 g).

Preparation of HE2DODC: 2-(bis(2-(oleoyloxy) ethyl)amino)-N,N-bis(2-hydroxyethyl)-N-methyl-2-oxoethanaminium bromide

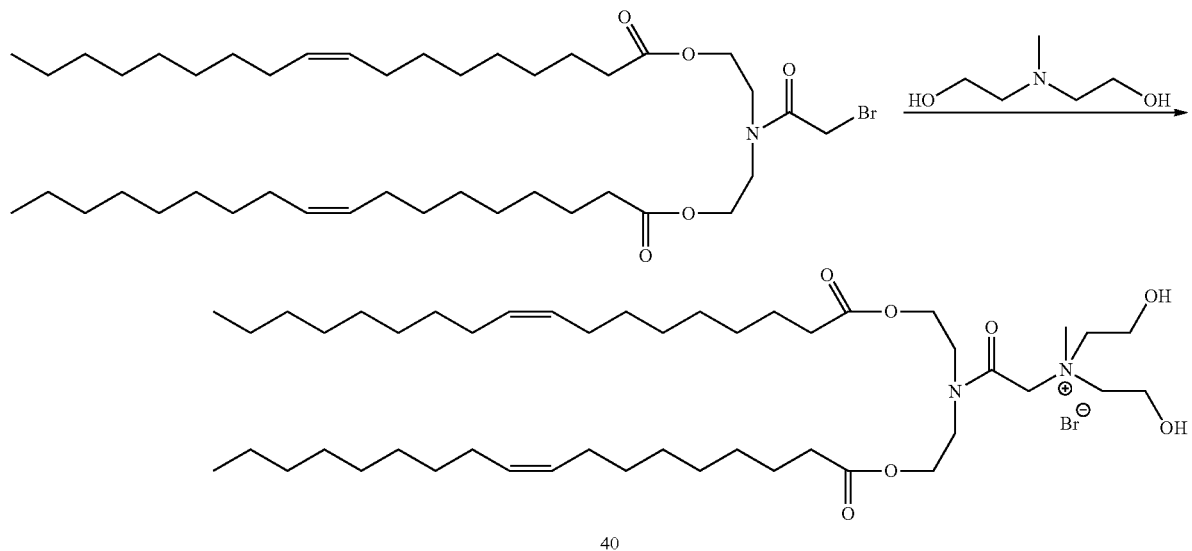

In a sealed system, (Z)-((2-bromoacetyl)azanediyl)bis(ethane-2,1-diyl) dioleate (2.08 g, 2.75 mmol) was combined with N-methyldiethylamine (1.58 mL, 13.8 mmol) was added. The reaction vessel was flushed with inert gas and then sealed. Reaction was heated to 50° C. and stirred overnight, and then concentrated. Purification by silica gel chromatography with DCM/MeOH gradient yielded 2-(bis(2-(oleoyloxy)ethyl)amino)-N,N-bis(2-hydroxyethyl)-N-methyl-2-oxoethanaminium bromide (479 mg). LCMS ESI+: m/z 793.7 (M+H).

Example 9: Preparation of 2-(bis(2-((9Z,12Z)-octadeca-9,12-dienoyloxy)ethyl)amino)-N-(2-hydroxyethyl)-N,N-dimethyl-2-oxoethanaminium bromide (HEDC-DLin)

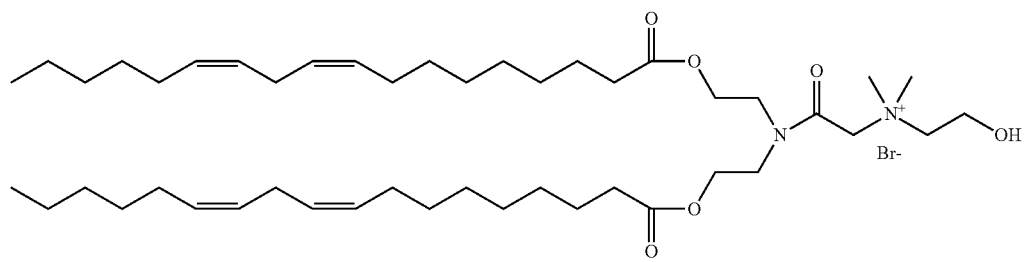 [SMILES: CCCCC/C=C\C/C=C\CCCCCCCC(=O)OCCN(CCOC(=O)CCCCCCC/C=C\C/C=C\CCCCC)C(=O)C[N+](C)(C)CCO ; [Br-]]

2-(bis(2-((9Z,12Z)-octadeca-9,12-dienoyloxy)ethyl)amino)-N-(2-hydroxyethyl)-N,N-dimethyl-2-oxoethanaminium bromide was prepared as described above for HEDC with the substitution of (9Z,12Z)-octadeca-9,12-dienoyl chloride for myristoyl chloride.

Example 10: Preparation of 2-(bis(2-(dodecanoyloxy)ethyl)amino)-N-(2-hydroxyethyl)-N,N-dimethyl-2-oxoethanaminium bromide (HEDC-12)

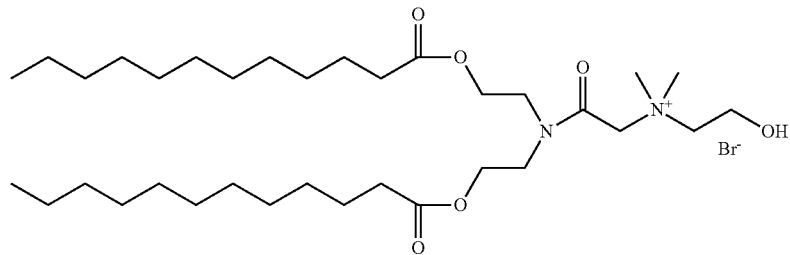 [SMILES: CCCCCCCCCCCC(=O)OCCN(CCOC(=O)CCCCCCCCCCC)C(=O)C[N+](C)(C)CCO ; [Br-]]

2-(bis(2-(Dodecanoyloxy)ethyl)amino)-N-(2-hydroxyethyl)-N,N-dimethyl-2-oxoethanaminium bromide was prepared as described above for HEDC with the substitution of dodecanoyl chloride for myristoyl chloride.

Example 11: Preparation of 2-((2-(bis(2-(tetradecanoyloxy)ethyl)amino)-2-oxoethyl)thio)-N-(2-hydroxyethyl)-N,N-dimethylethanaminium bromide (HES104)

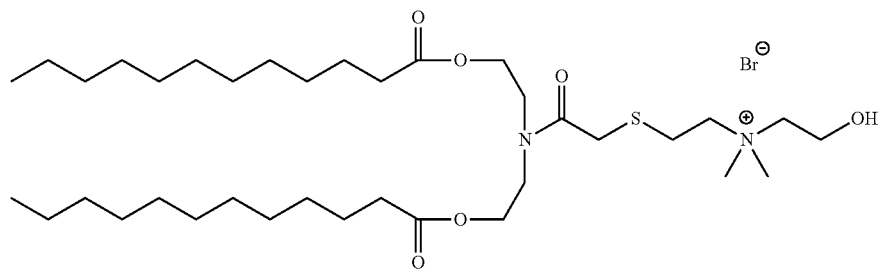 [SMILES: CCCCCCCCCCCC(=O)OCCN(CCOC(=O)CCCCCCCCCCC)C(=O)CSCC[N+](C)(C)CCO ; [Br-]]

Preparation of ((2-((2-(dimethylamino)ethyl)thio)acetyl)azanediyl)bis(ethane-2,1-diyl) ditetradecanoate (S104)

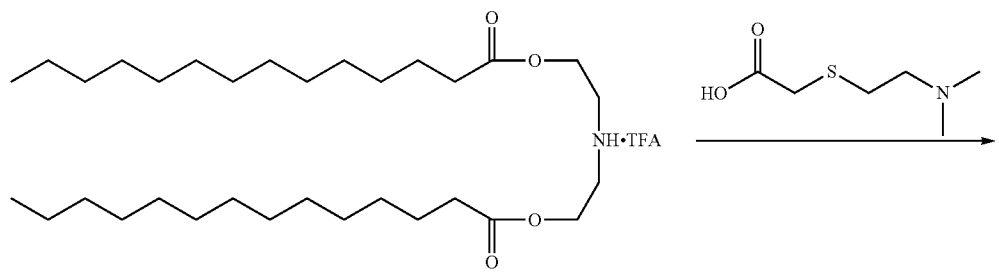

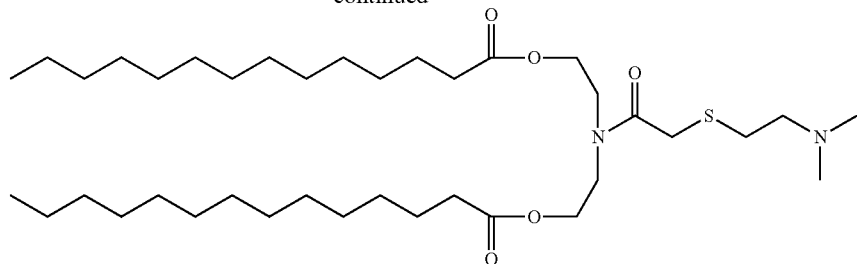

Synthesis of azanediylbis(ethane-2,1-diyl) ditetradecanoate TFA salt as described above (152 g, 238 mmol) was stirred with DCM (2.3 L) and 10% potassium bicarbonate (KHCO₃)(1.15 L) at 0-5° C. The organic phase was separated and the aqueous phase is further extracted with DCM (1.15 L). The combined organic phases were stirred with magnesium sulphate hydrate (236 g) for 30 minutes at 0-5° C., filtrated and washed with DCM (1.15 L). To the combined filtrates were added 2-((2-(dimethylamino)ethyl)thio) acetic acid hydrochloride (57.0 g, 285 mmol), EDC (68.4 g, 357 mmol) and DMAP (2.91 g, 23.8 mmol), and the suspension was stirred overnight at ambient temperature, after which period of time a clear solution was formed. Water (2.3 L) and methanol (460 mL) were added and after having stirred for 10 minutes the clear organic phase was separated. The turbid aqueous phase (pH 3.0) was extracted with DCM (575 mL). The combined organic extracts were concentrated yielding 143 g of crude material as the hydrochloride salt. The crude material (142.6 g) was transferred to a distillation flask with DCM (500 mL), and ethyl acetate (1 L) was added. The solution was heated to distillation at atmospheric pressure, and distillation was continued for 70 minutes to obtain a temperature of the residue of 76° C. A total volume of 1.4 L was obtained by addition of ethyl acetate (800 mL), and ethanol (70 mL) was added. The clear solution at 50° C. was cooled to 37° C. and seed crystals were added. Having observed initiation of significant crystallization for 10 minutes at 37-35° C., the suspension was cooled and stirred at 0° C. overnight and the precipitate was isolated by filtration, and washed with cold ethyl acetate (210 mL). Drying to a constant weight at ambient temperature in oil pump vacuum for 4.5 hours gave 134 g of recrystallized material as the hydrochloride salt, white crystalline solid. Tripotassium phosphate (85 g, 0.40 mol) and dipotassium hydrogen phosphate (226 g, 1.30 mol) was added to purified water (1.7 L), and the solution formed with pH 10.9 was cooled to 18-20° C. DCM (1.3 L) and recrystallized S104 hydrochloride (133 g, 0.188 mol) were added, and the mixture was stirred for 10 minutes. A clear organic phase was separated at moderate rate (over 35 minutes), and the turbid aqueous phase was further extracted with DCM (650 mL). The combined organic phases were stirred with anhydrous magnesium sulfate (65 g) for 40 minutes, and the mixture was filtered, washing with DCM (200 mL). The combined filtrates were evaporated from a 50° C. water bath under reduced pressure (down to 20 mBar, at which pressure evaporation was continued for one hour). Additional evaporation from a 15-20° C. water bath at oil pump vacuum, resulted in 126 g partially solidified oil. Cooling in −20° C. cooling bath gave complete solidification, and after drying at −20° C. under an oil pump vacuum, we have obtained 126 g of ((2-((2-(dimethylamino)ethyl)thio)acetyl)azanediyl)bis (ethane-2,1-diyl) ditetradecanoate (S104). HPLC indicated 98.1% purity.

Preparation of HES104: 2-((2-(bis(2-(tetradecanoyloxy)ethyl)amino)-2-oxoethyl)thio)-N-(2-hydroxyethyl)-N,N-dimethylethanaminium bromide

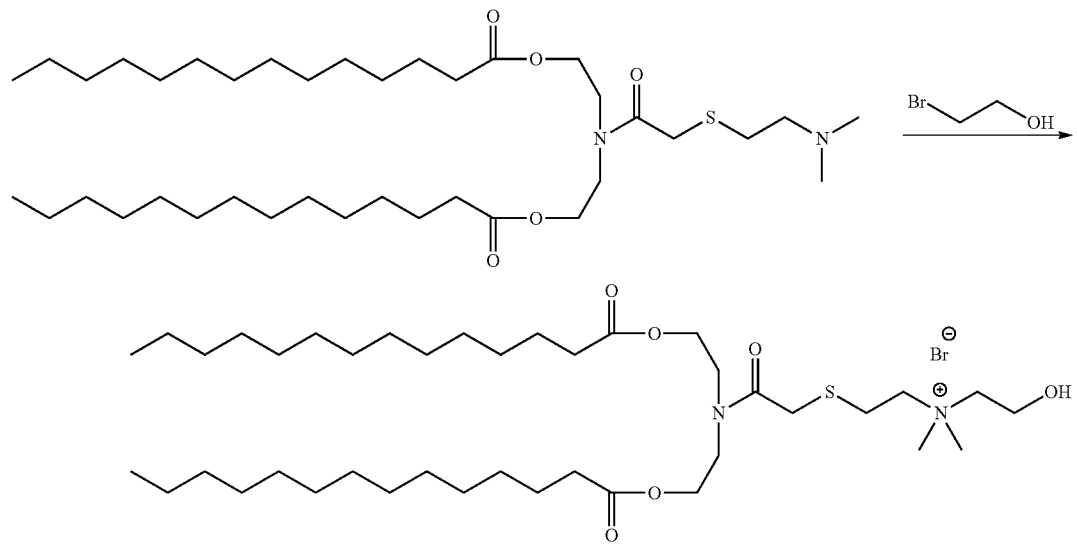

In a sealed system, ((2-((2-(dimethylamino)ethyl)thio)acetyl)azanediyl)bis(ethane-2,1-diyl) ditetradecanoate (1.00 g, 1.49 mmol) was combined with 2-bromoethanol (687 µL, 9.69 mmol) was added. The reaction vessel was flushed with inert gas and then sealed. Reaction was heated to 75° C. and stirred overnight, then cooled, and concentrated in vacuo. Purification by silica gel chromatography with DCM/MeOH gradient yielded 2-((2-(bis(2-(tetradecanoyloxy)ethyl)amino)-2-oxoethyl)thio)-N-(2-hydroxyethyl)-N,N-dimethylethanaminium bromide (HES104) (790 mg). LCMS ESI+: m/z 715.7 (M+H).

Example 12: Preparation of 2-((2-(bis(2-(oleoyloxy)ethyl)amino)-2-oxoethyl)thio)-N-(2-hydroxyethyl)-N,N-dimethylethanaminium bromide (HES104-DO)

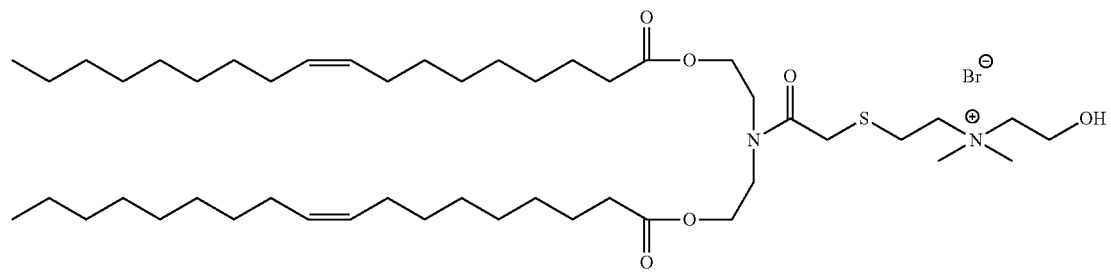 [SMILES: CCCCCCCC/C=C\CCCCCCCC(=O)OCCN(CCOC(=O)CCCCCCC/C=C\CCCCCCCC)C(=O)CSCC[N+](C)(C)CCO ; [Br-]]

Preparation of (Z)-((2-((2-(dimethylamino)ethyl)thio)acetyl)azanediyl)bis(ethane-2,1-diyl) dioleate

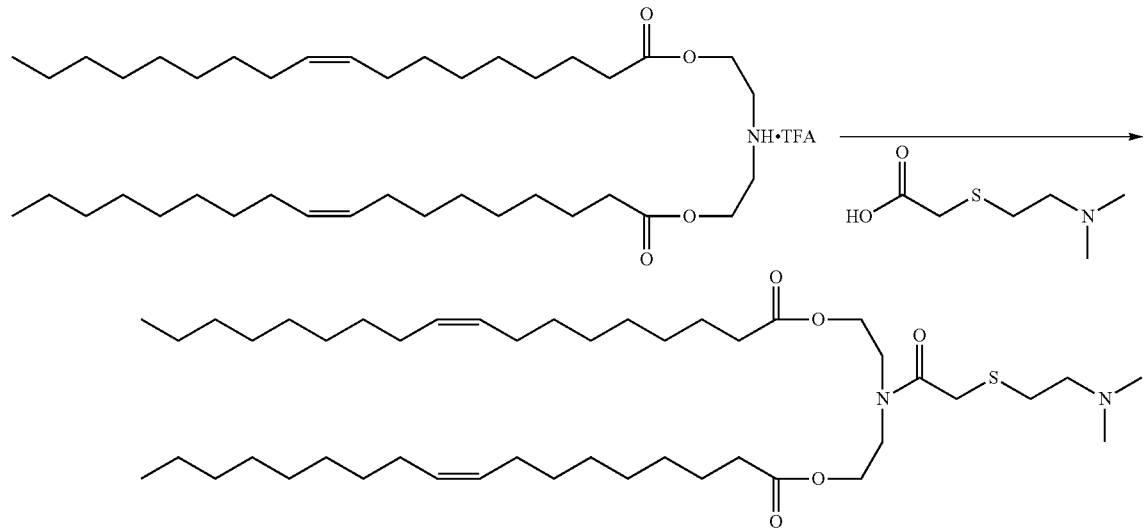

Synthesis of (Z)-azanediylbis(ethane-2,1-diyl) dioleate TFA salt previously described. (Z)-azanediylbis(ethane-2,1-diyl) dioleate TFA salt (4.06 g, 6.41 mmol) was stirred in DCM (60 mL) with 10% K₂CO₃ (30 mL) at 0-5° C. After 30 min, the organic phase was separated and the aqueous phase was further extracted with DCM (30 mL). The combined organic phases were stirred with anhydrous MgSO₄ for 30 minutes at 0-5° C., filtered, and washed with DCM (30 mL). To the combined filtrates were added to 2-((2-(dimethylamino)ethyl)thio)acetic acid (1.26 g, 7.70 mmol), EDC HCl salt (1.84 g, 9.62 mmol), DMAP (78.3 mg, 0.64 mmol). The thin suspension was stirred overnight at room temperature; after which the solution became clear. Next day, deionized water (60 mL) and methanol (30 mL) were added. After stirring for 10 minutes, the clear organic layer was isolated. The turbid aqueous phase is extracted with DCM. The combined organic extracts were concentrated. Crude material was filtered through silica and taken up in DCM (40 mL) and phosphate buffered saline (PBS) (pH=11, 50 mL) was added. The mixture was stirred at room temperature for 10 min. The organic phase was separated and the aqueous phase is extracted again with DCM (15 mL). The combined organic phases were stirred with anhydrous MgSO₄ for 30 minutes. The mixture was then filtered, and washed with DCM. The combined filtrates were concentrated in vacuo to yield (Z)-((2-((2-(dimethylamino)ethyl)thio)acetyl)azanediyl)bis(ethane-2,1-diyl) dioleate (3.44 g).

Preparation of HES104-DO

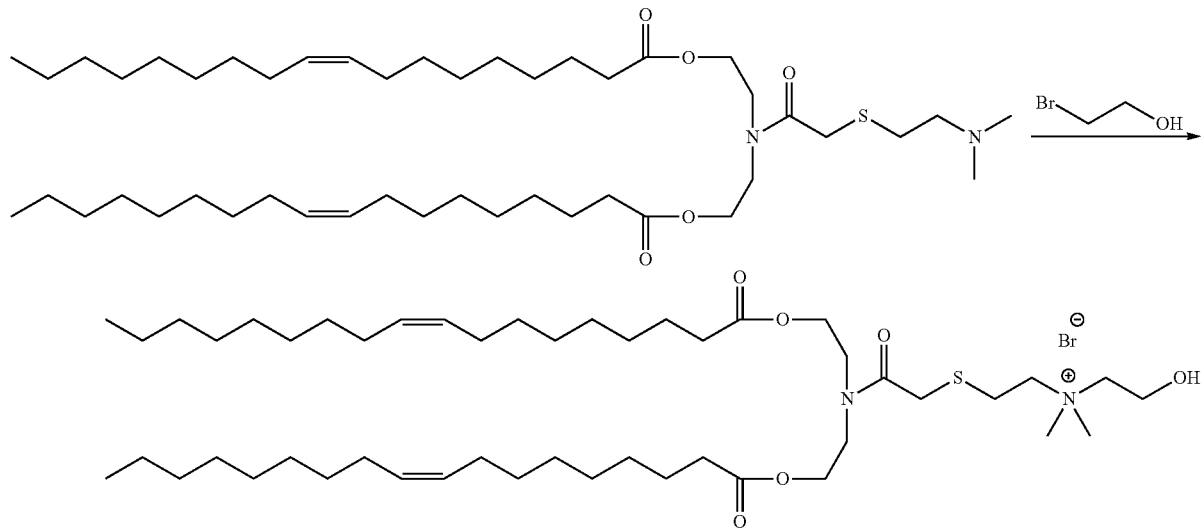

In a sealed system, (Z)-((2-((2-(dimethylamino)ethyl)thio)acetyl)azanediyl)bis(ethane-2,1-diyl) dioleate (540 mg, 0.693 mmol) was combined with 2-bromoethanol (319 μL) was added. The reaction vessel was flushed with inert gas and then sealed. Reaction was heated to 75° C. and stirred overnight. Next day, cooled and concentrated in vacuo. Purification by silica gel chromatography with DCM/MeOH gradient yielded 2-((2-(bis(2-(oleoyloxy)ethyl)amino)-2-oxoethyl)thio)-N-(2-hydroxyethyl)-N,N-dimethyl-ethanaminium bromide (324 mg). LCMS ESI+: m/z 823.8 (M+H).

Example 13: Preparation of 2-((bis(2-(oleoyloxy)ethyl)carbamoyl)thio)-N-(2-hydroxyethyl)-N,N-dimethylethane-aminium bromide (HETU104-DO)

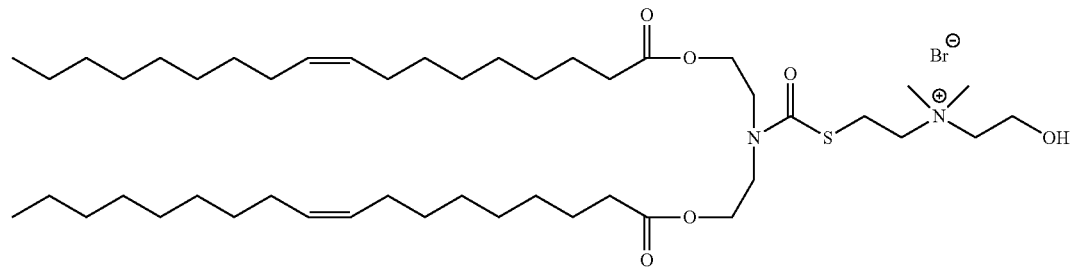 [SMILES: CCCCCCCC/C=C\CCCCCCCC(=O)OCCN(CCOC(=O)CCCCCCC/C=C\CCCCCCCC)C(=O)SCC[N+](C)(C)CCO ; [Br-]]

Preparation of (Z)-((((2-(dimethylamino)ethyl)thio)carbonyl)azanediyl)bis(ethane-2,1-diyl) dioleate

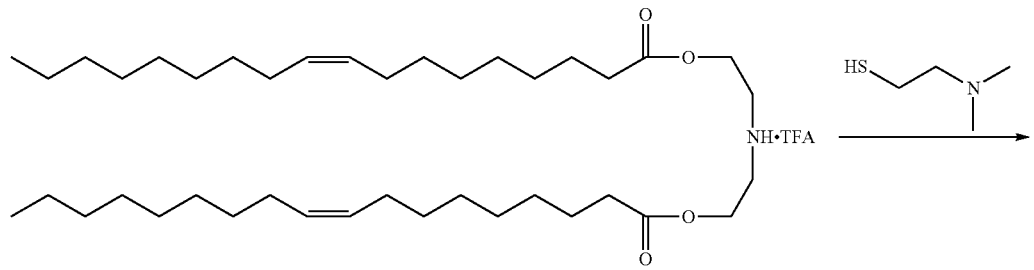

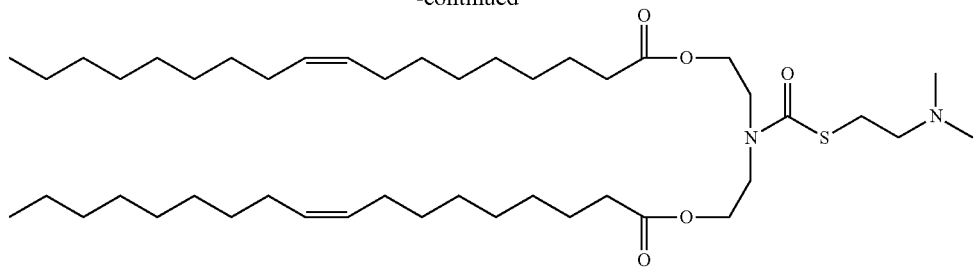

Synthesis of (Z)-((tert-butoxycarbonyl)azanediyl)bis(ethane-2,1-diyl) dioleate previously described. (Z)-((tert-butoxycarbonyl)azanediyl)bis(ethane-2,1-diyl) dioleate (4.2 g, 5.72 mmol) was dissolved in DCM (20 mL) and cooled in an ice bath. TFA (20 mL) was added and the mixture was stirred under a blanket of inert gas for 20 minutes. Afterwards, the mixture was concentrated in vacuo. The residue was partitioned between 10% $K_2CO_3$ (20 mL) and DCM (20 mL). The mixture was stirred in an ice bath for 20 minutes. The organic portion was collected, and the turbid aqueous layer was extracted with DCM (2×10 mL). The combined organic extracts were added with anhydrous $MgSO_4$ and stirred at 0 for 20 minutes. The suspension was filtered and washed DCM (10 mL). Diphosgene (1.38 mL, 11.4 mmol) was added to (Z)-azanediylbis(ethane-2,1-diyl) dioleate material in DCM and stirred under a blanket of inert gas at room temperature. Next day, DCM and excess diphosgene was removed in vacuo. 2-(dimethylamino)ethane thiol HCl salt (4.05 g, 28.6 mmol) was taken up in DCM (50 mL) and triethylamine (5.2 mL, 37.2 mmol) and added to (Z)-((chlorocarbonyl)azanediyl)bis(ethane-2,1-diyl) dioleate residue. Reaction mixture was stirred overnight at room temperature. The mixture was diluted with DCM and washed with 0.3M HCl (75 mL), water (75 mL) and 10% $K_2CO_3$ (75 mL). The aqueous washes were back-extracted with DCM (25 mL). The organics was dried over anhydrous $MgSO_4$, filtered, and concentrated in vacuo. Purification by silica gel chromatography with DCM/MeOH gradient yielded (Z)-((((2-(dimethylamino)ethyl)thio)carbonyl)azanediyl)bis(ethane-2,1-diyl) dioleate (1.90 g).

Preparation of HETU104DO

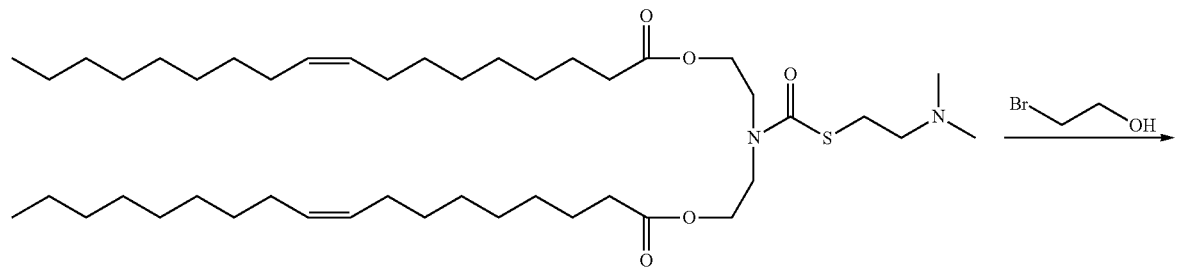

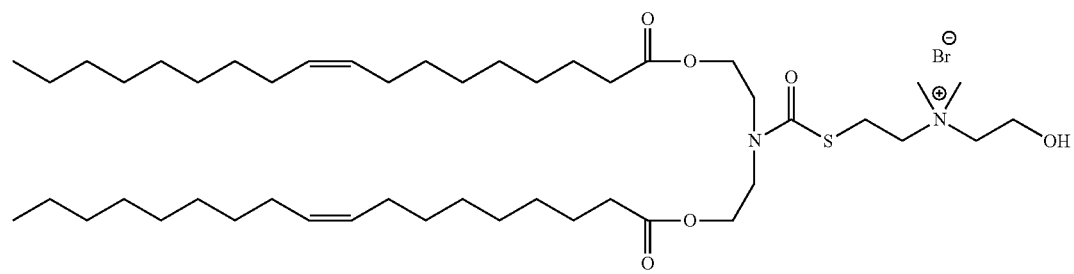

In a sealed system, (Z)-((((2-(dimethylamino)ethyl)thio) carbonyl)azanediyl)bis(ethane-2,1-diyl) dioleate (615 mg, 0.804 mmol) was combined with 2-bromoethanol (370 µL, 5.22 mmol) was added. The reaction vessel was flushed with inert gas and then sealed. Reaction was heated to 75° C. and stirred overnight, then cooled and concentrated in vacuo. Purified by silica gel chromatography with a DCM/MeOH gradient yielded 2-((bis(2-(oleoyloxy)ethyl)carbamoyl) thio)-N-(2-hydroxyethyl)-N,N-dimethylethanaminium bromide (473 mg). LCMS ESI+: m/z 809.8 (M+H).

Example 14: Formation of Nucleic Acid-Lipid Particles

The siRNA referred to in the formulation protocols are double stranded siRNA sequence with 21-mer targeting HSP47/gp46 wherein HSP47 (mouse) and gp46 (rat) are homologs—the same gene in different species as follows: rat HSP47-C double stranded siRNA used for in vitro assay (rat pHSCs)

```
                                          (SEQ. ID NO. 2)
Sense (5'->3')    GGACAGGCCUCUACAACUAUU (SEQ. ID NO. 3)
Antisense (3'->5') TTCCUGUCCGGAGAUGUUGAU
``` mouse HSP47-C double stranded siRNA used in formulations for in vivo assay (mouse CC14 model)

```
                                          (SEQ. ID NO. 4)
Sense (5'->3')    GGACAGGCCUGUACAACUAUU (SEQ. ID NO. 5)
Antisense (3'->5') TTCCUGUCCGGACAUGUUGAU
```

Cationic Lipid Stock Preparation.

Stock solutions of cationic lipids were prepared by combining the cationic lipid with DOPE, cholesterol, and diVA-PEG-diVA in ethanol at concentrations of 6.0, 5.1 and 2.7 and 2.4 mg/mL, respectively. If needed, solutions were warmed up to about 50° C. to facilitate the dissolution of the cationic lipids into solution.

Empty Liposome Preparation.

A cationic lipid stock solution was injected into a rapidly stirring aqueous mixture at 35-40° C. through injection needle(s) at 1.5 mL/minutes per injection port. The cationic lipid stock solution to the aqueous solution ratio (v/v) is fixed at 35:65. Upon mixing, empty vesicles formed spontaneously. The resulting vesicles were then equilibrated at 35-40° C. for 10 minutes before the ethanol content was reduced to ~12%. The empty liposomes were then diafiltered against 10× volumes of aqueous buffer to remove ethanol.

Lipoplex Preparation.

The empty vesicle prepared according to the above method was diluted to the final volume of 1 mM concentration of cationic lipid by 9% sucrose. To the stirring solution, 100 µL of 5% glucose in RNase free water was added for every mL of the diluted empty vesicle ("EV") and mixed thoroughly. 150 µL of 10 mg/mL siRNA solution in RNase free water was then added at once and mixed thoroughly. The mixture was then diluted with 5% glucose solution with 1.750 mL for every mL of the EV used. The mixture was stirred at about 200 rpm at room temperature for 10 minutes. Using a semi-permeable membrane with ~100,000 MW cut-off in a cross-flow ultrafiltration system using appropriately chosen peristaltic pump (e.g., Midgee Hoop, UFP-100-H24LA), the mixture was concentrated to about ⅓ of the original volume (or desired volume) and then diafiltered against 5 times of the sample volume using an aqueous solution containing 3% sucrose and 2.9% glucose. The product was then filtered through a combined filter of 0.8/0.2 micron pore size under aseptic conditions before use.

Formation of Non-diVA siRNA Containing Liposomes.

Cationic lipid, DOPE, cholesterol, and a PEG-conjugated lipid were solubilized in absolute ethanol at a molar ratio of 50:10:38:2. The siRNA was solubilized in 50 mM citrate buffer and the temperature was adjusted to 35-40° C. The ethanol/lipid mixture was then added to the siRNA-containing buffer while stirring to spontaneously form siRNA loaded liposomes. Lipids were combined with siRNA to reach a final total lipid to siRNA ratio of 5:1 to 15:1 (wt:wt). The siRNA loaded liposomes were diafiltered against 10× volumes of PBS (pH 7.2) to remove ethanol and exchange the buffer. Final product was passed through 0.22 µm, sterilizing grade, PES filter for bioburden reduction. This process yielded liposomes with a mean particle diameter of 50-100 nm, PDI<0.2, and >85% entrapment efficiency.

Formation of siRNA Containing Liposomes Co-Solubilized with diVA.

siRNA-diVA-Liposome formulations were prepared using the method described above. DiVA-PEG-diVA was co-solubilized in absolute ethanol with the other lipids (cationic lipid, DOPE, cholesterol, and PEG-conjugated lipids at a ratio of 50:10:38:2) prior to addition to the siRNA containing buffer. Molar content of diVA-PEG-diVA ranged from 0.1 to 5 molar ratio (i.e., 50:10:38:2:0.1 to 50:10:38:2:5). This process yielded liposomes with a mean particle diameter of 50-100 nm, PDI<0.2, and >85% entrapment efficiency.

Formation of siRNA Containing Liposomes with Cationic Lipids.

siRNA-diVA-Liposome formulations and siRNA-Liposome formulations were prepared using the method described above. Cationic lipid can be, for example, HEDC, HEDODC, DC-6-14, or any combination of these cationic lipids.

Formation of siRNA Containing Liposomes Decorated with diVA.

siRNA-Liposome formulations were prepared using the method described above and diluted to a siRNA concentration of 0.5 mg/mL in PBS. Cationic lipid can be HEDC, HEDODC, DC-6-14, or any combination of these cationic lipids. diVA-PEG-diVA was dissolved in absolute ethanol (200 proof) to a final concentration ranging from 10 to 50 mg/mL. An appropriate amount of ethanol solution was added to the siRNA-Liposome solution to yield a final molar percentage between 2 to 10 mol %. Solution was plunged up and down repeatedly with a pipette to mix. diVA-PEG-diVA concentration and ethanol addition volume were adjusted to keep the addition volume >1.0 µL and the final ethanol concentration <3% (vol/vol). Decorated liposomes were then incubated at ambient temperature for 1 hour on an orbital shaker prior to in vitro or in vivo evaluation.

The following tables set forth preferred embodiments of the description herein expressed in terms of molar ratios, as well as the equivalent mol % and weight percentages.

| Formulation | Molar Ratio | | | | |
|---|---|---|---|---|---|
| | Cationic Lipid | DOPE | Cholesterol | PEG-lipid | diVA |
| HEDODC Liposome | 50 | 10 | 38 | 2 | — |
| HEDODC Liposome + diVA | 50 | 10 | 38 | 2 | 5 |
| DC-6-14 Lipoplex | 40 | 30 | 30 | — | — |
| DC-6-14 Lipoplex + diVA | 40 | 30 | 30 | — | 5 |

| Formulation | Mol. % | | | | |
|---|---|---|---|---|---|
| | Cationic Lipid | DOPE | Cholesterol | PEG-lipid | diVA |
| HE-DODC Liposome | 50 | 10 | 38 | 2 | — |
| HE-DODC Liposome + diVA | 47.6 | 9.5 | 36.2 | 1.9 | 4.8 |
| DC-6-14 Lipoplex | 40 | 30 | 30 | — | — |
| DC-6-14 Lipoplex + diVA | 38.1 | 28.6 | 28.6 | — | 4.8 |

| Formulation | Weight Percent | | | | |
|---|---|---|---|---|---|
| | Cationic Lipid | DOPE | Cholesterol | PEG-lipid | diVA |
| HE-DODC Liposome | 61.1 | 10.8 | 21.3 | 6.9 | — |
| HE-DODC Liposome + diVA | 52.9 | 9.3 | 18.4 | 5.9 | 13.4 |
| DC-6-14 Lipoplex | 43.8 | 37 | 19.2 | — | — |
| DC-6-14 Lipoplex + diVA | 37.2 | 31.4 | 16.3 | — | 15.0 |

Example 15: Transfection with Liposomal Formulations

The transfection method is the same for LX-2 and pHSC. The liposome formulations or lipoplex formulations of the description herein were mixed with growth medium at desired concentrations. 100 μl of the mixture was added to the cells in 96-well plate and cells were incubated for 30 minutes at 37° C. in the incubator with 5% $CO_2$. After 30 min, medium was replaced with fresh growth medium. After 48 h of transfection, cells were processed using CELL-TO-CT® lysis reagents (Applied Biosystems) according to the manufacturer's instructions.

Quantitative RT-PCR for Measuring HSP47 mRNA Expression (qRT-PCR)

HSP47 and GAPDH TAQMAN® assays and One-Step RT-PCR master mix were purchased from Applied Biosystems. Each PCR reaction contained the following composition: One-step RT-PCR mix 5 μl, TAQMAN® RT enzyme mix 0.25 μl, TAQMAN® gene expression assay probe (HSP47) 0.25 μl, TAQMAN® gene expression assay probe (GAPDH) 0.5 μl, RNase free water 3.25 μl, Cell lysate 0.75 μl, Total volume of 10 μl. GAPDH was used as endogenous control for the relative quantification of HSP47 mRNA levels. Quantitative RT-PCR was performed in VIIA 7® real-time PCR system (Applied Biosciences) using an in-built Relative Quantification method. All values were normalized to the average HSP47 expression of the mock transfected cells and expressed as percentage of HSP47 expression compared to mock.

In Vivo Experiments:

Female C57B1/6 retired breeder mice (Charles River) with a weight range of 24-30 grams were used for this study. Animals were randomly distributed by weight into 10 groups of 10 animals each. All animal procedures were approved by Bio-Quant's IACUC and/or attending veterinarian as necessary and all animal welfare concerns were addressed and documented. Mice were anesthetized with Isoflurane and exsanguinated via the inferior vena cava.

Up-regulation of heat shock protein 47 (HSP47) was induced via intraperitoneal injecting $CCl_4$ ($CCl_4$ in olive oil, 1:7 (vol/vol), 1 μL per gram body weight) given every other day for 7 days (day 0, 2, 4, 6). On day three mice were treated for 4 consecutive days (day 3, 4, 5, 6) with liposome or lipoplex formulations of the description herein or PBS by IV injection into the tail vein. One group of ten mice (naïve) received neither $CCl_4$ treatment nor IV injection and served as the control group for normal HSP47 gene expression.

| Experimental Timeline | | | | | | | | |
|---|---|---|---|---|---|---|---|---|
| Day | 0 | 1 | 2 | 3 | 4 | 5 | 6 | 7 |
| $CCl_4$ IP Injection | X | X | X | X | X | X | X | |
| Test Article IV Injection | | | | X | X | X | X | |
| Sample Collection (n = 10) | | | | | | | | X |

On day 7 and approximately 24 hours after final IV injection, all remaining mice were sacrificed and the livers were perfused with PBS prior to collecting liver samples for PCR analysis. An approximate 150 mg sample from each mouse liver was collected and placed in 1.5 mL RNA later stabilization reagent (Qiagen) and stored at 2-8° C. until analysis. Liver samples were not collected from areas of clear and marked liver damage and/or necrosis.

Total RNA from mouse livers was extracted using RNEASY® columns (Qiagen) according to the manufacturer's protocol. 20 ng of total RNA was used for quantitative RT-PCR for measuring HSP47 expression. HSP47 and GAPDH TAQMAN® assays and One-Step RT-PCR master mix were purchased from Applied Biosystems. Each PCR reaction contained the following composition: One-step RT-PCR mix 5 μl, TAQMAN® RT enzyme mix 0.25 μl, TAQMAN® gene expression assay probe (HSP47) 0.25 μl, TAQMAN® gene expression assay probe (GAPDH) 0.5 μl, RNase free water 3.25 μl, RNA 0.75 μl, Total volume of 10 μl. GAPDH was used as endogenous control for the relative quantification of HSP47 mRNA levels. Quantitative RT-PCR was performed in VIIA 7® realtime PCR system using an in-built Relative Quantification method. All values were normalized to the average HSP47 expression of the naïve animal group and expressed as percentage of HSP47 expression compared to naïve group.

The formulations described in FIG. 1 are as follows:

| Formulation | Molar Ratio | | | | |
|---|---|---|---|---|---|
| | Cationic Lipid | DOPE | Cholesterol | PEG-lipid | VA or VA-conjugate |
| DC-6-14 Lipoplex | 40 | 30 | 30 | — | — |
| DC-6-14 Lipoplex + VA* | 40 | 30 | 30 | — | 40 |
| HEDC Liposome | 50 | 10 | 38 | 2 | — |
| HEDC Liposome + VA-PEG-VA* | 50 | 10 | 38 | 2 | 5 |

-continued

|  | Molar Ratio | | | | |
| --- | --- | --- | --- | --- | --- |
| Formulation | Cationic Lipid | DOPE | Cholesterol | PEG-lipid | VA or VA-conjugate |
| HEDC Liposome + diVA-PEG-diVA* | 50 | 10 | 38 | 2 | 5 |

Figure 2:
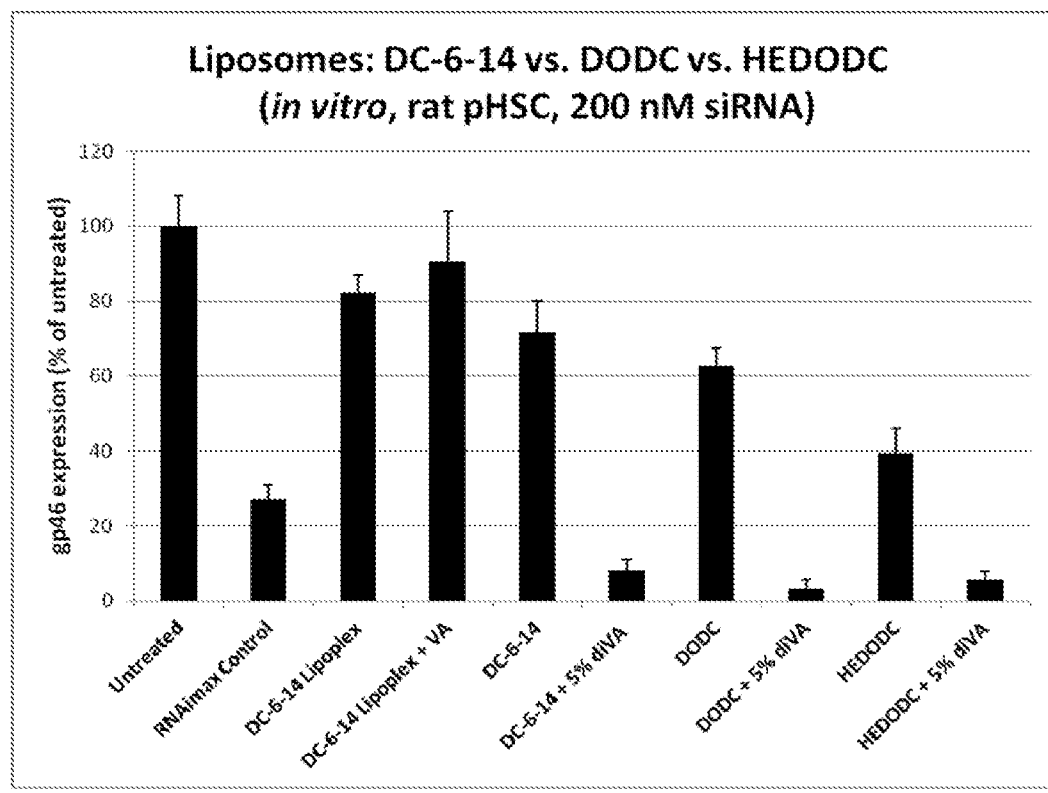
FIG. 2 depicts an in vitro comparison of gene knockdown using cationic lipids.

*VA-PEG-VA and diVA-PEG-diVA were added via co-solubilization. VA was added via decoration post-process The formulations described in FIG. 2 are as follows

|  | Molar Ratio | | | | |
| --- | --- | --- | --- | --- | --- |
| Formulation | Cationic Lipid | DOPE | Cholesterol | PEG-lipid | VA or VA-conjugate |
| DC-6-14 Lipoplex | 40 | 30 | 30 | — | — |
| DC-6-14 Lipoplex + VA* | 40 | 30 | 30 | — | 40 |
| DC-6-14 Liposome | 50 | 10 | 38 | 2 | — |
| DC-6-14 Liposome + diVA-PEG-diVA* | 50 | 10 | 38 | 2 | 5 |
| HEDODC Liposome | 50 | 10 | 38 | 2 | — |
| HEDODC Liposome + diva-PEG-diVA* | 50 | 10 | 38 | 2 | 5 |

*diVA-PEG-diVA was added via co-solubilization. VA was added via decoration post-process.

Figure 3:
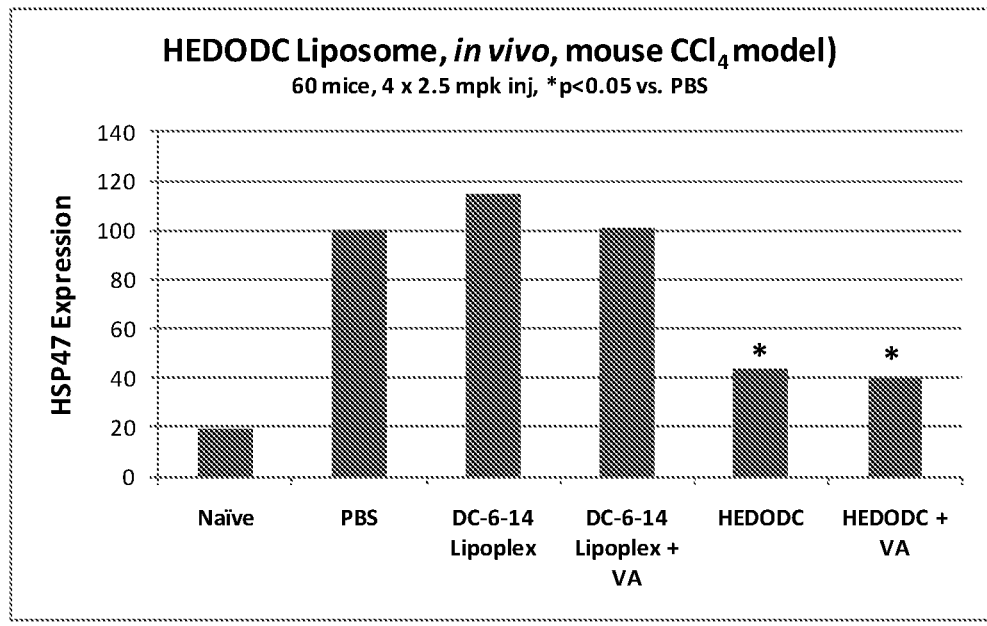
FIG. 3 depicts an evaluation of gene expression in vivo with exemplary HEDODC liposome formulations of the description herein (* indicates p<0.05).

The formulations described in FIG. 3 are as follows.

|  | Molar Ratio | | | | |
| --- | --- | --- | --- | --- | --- |
| Formulation | Cationic Lipid | DOPE | Cholesterol | PEG-lipid | VA or VA-conjugate |
| DC-6-14 Lipoplex | 40 | 30 | 30 | — | — |
| DC-6-14 Lipoplex + VA* | 40 | 30 | 30 | — | 40 |
| HEDODC Liposome | 50 | 10 | 38 | 2 | — |
| HEDODC Liposome + diVA-PEG-diVA* | 50 | 10 | 38 | 2 | 5 |

*diVA-PEG-diVA was added via co-solubilization. VA was added via decoration post-process

Figure 4:
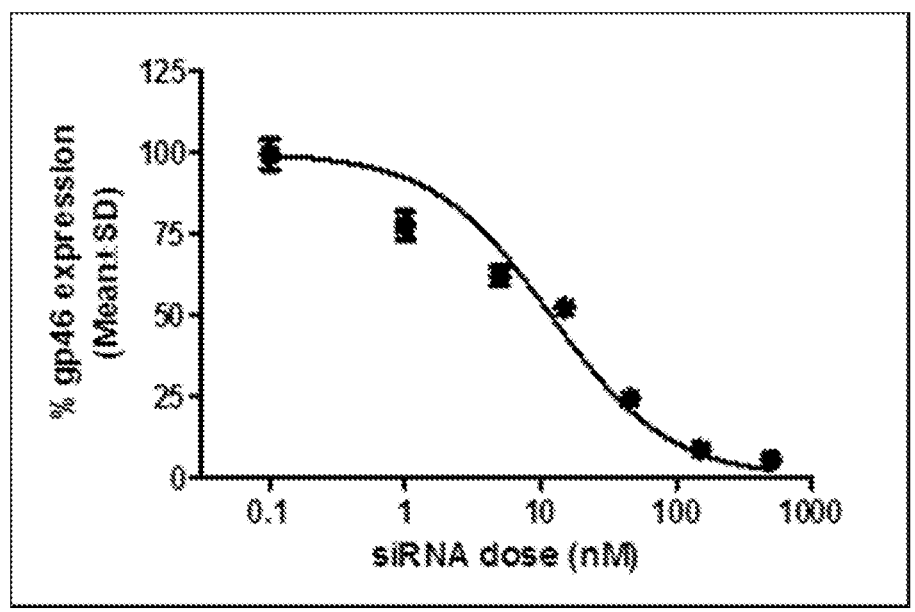
FIG. 4 depicts an evaluation of gene expression in vitro with exemplary HEDC liposome formulations of the Example 15. Error bars indicate standard deviations (n=3). A sigmoidal dose-response curve is shown based on best fit. An $EC_{50}$ value was calculated from the curve. This is indicated to be 11.8 nM.

Example 16: In Vitro Efficacy (pHSC), Dose Response pHSC In Vitro Assay Description:

Primary hepatic stellate cells (pHSC) in a 96-well plate were incubated with formulations (HEDC:S104:DOPE:Chol:Peg-DMPE:DiVA, 20:20:30:25:5:2) of increasing siRNA concentration. After 30 minutes, cells were washed and treated with fresh growth medium and incubated at 37° C. for 48 hours. At that time, cells were lysed and gp46 and GAPDH mRNA levels were measured by quantitative RT-PCR (TAQMAN®) assay. mRNA levels of gp46 were normalized to GAPDH levels. Normalized gp46 levels are expressed as the percent of untreated control cells. FIG. 4 shows the results. Error bars indicate standard deviations (n=3). Fitting data to a sigmoidal dose-response curve using Graphpad yielded an $EC_{50}$ of 11.8 nM.

Example 17: Toxicity

HepG2 Cytotoxicity Assay Description

HepG2 cells, an adherent cell line derived from human hepatocellular carcinoma, was cultured in MEM/EBSS (Hyclone, Logan, Utah, Cat #SH30024.01) supplemented with 10% FBS (Hyclone, Logan, Utah Cat #SH30910). HepG2 cells were seeded in 96-well Optilux black plates (BD Falcon, Cat #BD353220) at the density of 5000 cells/well overnight. Formulations were added to each well to final indicated siRNA concentration (n=3). At 48 h post formulation addition, cell viability was determined using CellTiter-Glo Luminescent Cell Viability Assay Kit (Promega, Cat #G7572) following manufacture's instruction. Chemiluminescent signal were measured on Clarity Luminescence Microplate Reader (502-Biotek, Winooski, Vt.). Viability was calculated based on percentage of chemiluminescent signal in formulation treated well normalized against mock treated wells.

Combinations of quatemary amine cationic lipids of formula I with their respective ionizable synthetic precursors were evaluated (as shown in the examples below, i-DC and HEDC, INT4 and DODC, S104 and HES104).

The following table provides exemplary results from different formulations. Combinations of quaternary amine cationic lipids with ionizable cationic lipids surprisingly and unexpectedly were less toxic than liposomes containing a single cationic lipid (see examples HEDC vs. HEDC+ iDC; and DODC vs. DODC+INT4 in the table below). The HEDC+S104 combination was identified as another preferred formulation.

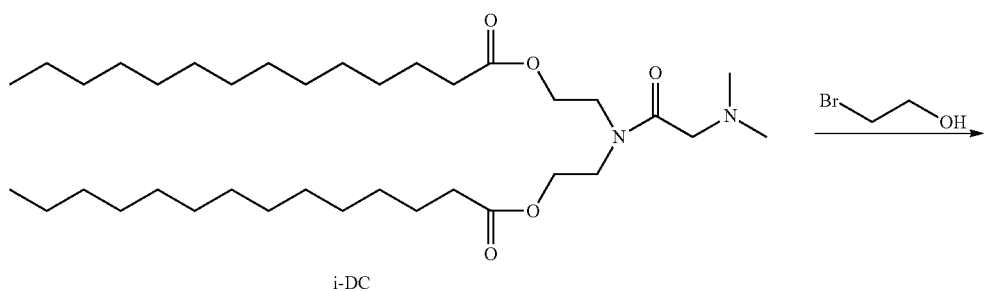

i-DC

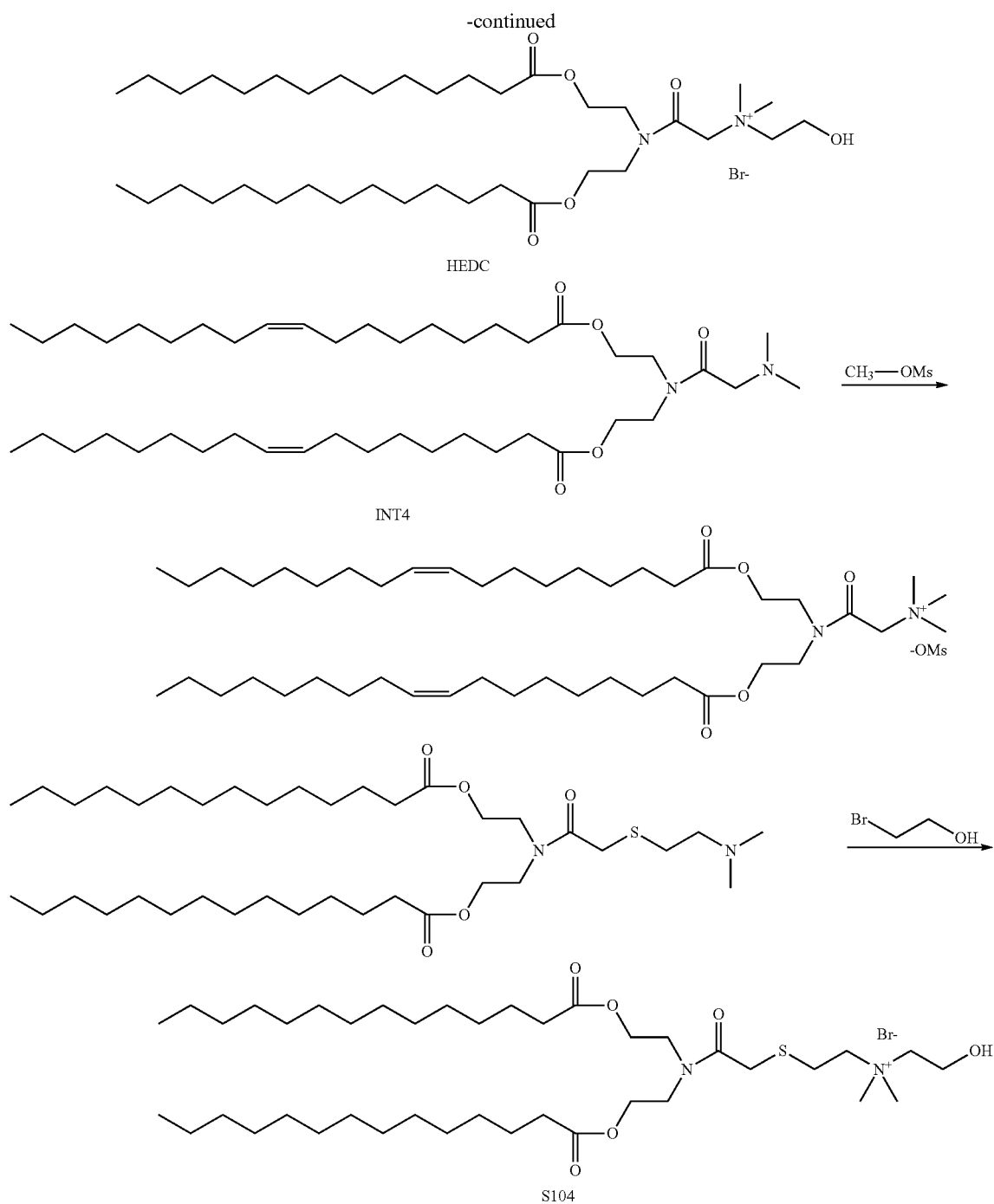
| Variant Description | Formulation Variants | in vitro KD* (%) | in vitro tox (% cell viability, HepG2 @ 200 nM) |
|---|---|---|---|
| Cationic Lipid Content (2 mol % PEG-Lipid) | 40 mol % HEDC, no ionizable lipid | 90% @ 200 nM | 27% |
| | 50 mol % DODC, no ionizable lipid | 90% @ 200 nM | 55% |
| | 25 mol % DODC:25 mol % INT4 | 90% @ 200 nM | 90% |
| | 20 mol % HEDC:20 mol % i-DC | 89% @ 200 nM | 57% |
| | 20 mol % HEDC:20 mol % S104 | 90% @ 200 nM | 52% |
| | 10 mol % HEDC:30 mol % S104 | 90% @ 200 nM | 71% |
| | 5 mol % HEDC:35 mol % S104 | 90% @ 200 nM | 80% |

-continued

| Variant Description | Formulation Variants | in vitro KD* (%) | in vitro tox (% cell viability, HepG2 @ 200 nM) |
|---|---|---|---|
| PEG Lipid Content | 2 mol % | 70% | |
| (DMPE-PEG) | 5 mol % | 60% | |
| | 7 mol % | 55% | |
| | 10 mol % | 45% | |
| DiVA Content | 0.25 mol % | 35% | |
| (w/5 mol % DMPE-PEG) | 0.5 mol % | 40% | |
| | 1.0 mol % | 60% | |
| | 2.0 mol % | 70% | |
| DOPE:Cholesterol Ratio | DOPE-0%:Cholesterol 55% | 89% | |
| (w/5 mol % DMPE-PEG) | DOPE-5%:Cholesterol 50% | 82% | |
| | DOPE-10%:Cholesterol 45% | 77% | |
| | DOPE-15%:Cholesterol 40% | 74% | |
| | DOPE-20%:Cholesterol 35% | 80% | |
| | DOPE-25%:Cholesterol 30% | 79% | |
| | DOPE-30%:Cholesterol 25% | 82% | |
| | DOPE-35%:Cholesterol 20% | 80% | |
| | DOPE-40%:Cholesterol 15% | 84% | |
| | DOPE-45%:Cholesterol 10% | 80% | |
| | DOPE-50%:Cholesterol 5% | 78% | |
| | DOPE-55%:Cholesterol 0% | 72% | |
| siRNA:Total Lipid Ratio | 0.07 | 80% | |
| (w/5 mol % DMPE-PEG) | 0.09 | 75% | |
| | 0.11 | 82% | |

*All data with 20 mol % HEDC, 20 mol % S104, and 2 mol % DiVA @ 50 nM siRNa dose unless otherwise noted In Vivo Toxicity The HEDC:S104 (20:20) formulation is exceptionally well tolerated in preliminary in vivo toxicity studies. No toxicity is observed when the formulation is injected intravenously at doses up to 25 mg/kg (rat) and 12 mg/kg (monkey).

Example 18: In Vivo Efficacy (Rat DMNQ)

In vivo activity of target formulation was evaluated in the short-term liver damage model (referred to as the Quick Model, DMNQ). In this model, the short-term liver damage induced by treatment with a hepatotoxic agent such as dimethylnitrosamine (DMN) is accompanied by the elevation of gp46 mRNA levels. To induce these changes, male Sprague-Dawley rats were injected intraperitoneally with DMN on six consecutive days. At the end of the DMN treatment period, the animals were randomized to groups based upon individual animal body weight. Formulations were administered as a single intravenous dose, one hour after the last injection of DMN. Twenty four hours later, liver lobes were excised and both gp46 and MRPL19 mRNA levels were determined by quantitative RT-PCR (TAQMAN®) assay. Levels of gp46 mRNA were normalized to MRPL19 levels.

Figure 5:
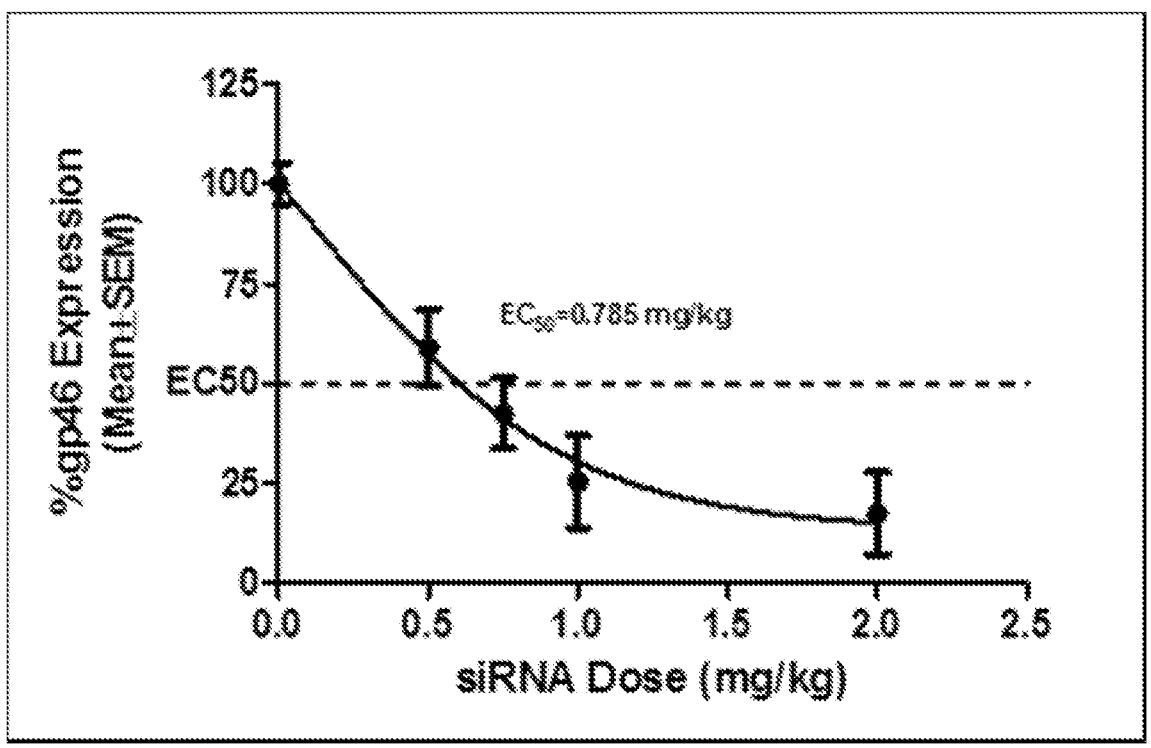
FIG. 5 shows the results of measurements in vivo using a rat DMNQ model. After subtracting background heat-shock glycoprotein 46 (gp46) mRNA levels determined from the naïve group, all test group values were normalized to the average gp46 mRNA of the vehicle group (expressed as a percent of the vehicle group). The mean gp46 mRNA level following treatment showed dose-dependent response and curve fitting to a sigmoidal dose response curve. The calculated effective dose, $ED_{50}$ value is 0.79 mg/kg.

Male Sprague-Dawley rats were treated with DMN at 10 mg/kg on day 1, 2, 3 and 5 mg/kg on day 4, 5, 6 through intraperitoneally dosing to induce liver damage. Animals (n=8/group) were injected intravenously either with formulations at a dose of 0.5, 0.75, 1.0, 2 mg/kg siRNA in a formulation consisting of HEDC:S104:DOPE:Chol:Peg-DMPE:DiVA (20:20:30:25:5:2), or PBS (vehicle), one hour after the last injection of DMN. Twenty four hours later, total siRNA was purified from a section of the right liver lobe from each animal and stored at 4° C. until RNA isolation. Control groups included a PBS vehicle group (DMN-treated) and naïve (untreated; no DMN) group. FIG. 5 shows the results of measurements. After subtracting background gp46 mRNA levels determined from the naïve group, all test group values were normalized to the average gp46 mRNA of the vehicle group (expressed as a percent of the vehicle group). The mean gp46 mRNA level following treatment showed dose-dependent response and curve fitting to sigmoidal dose response curve yielded $EC_{50}$ of 0.79 mg/kg.

Example 19: In Vivo Efficacy (Rat DMNC)

Male Sprague Dawley rats (130-160 g) were treated DMN through intraperitoneally dosing to induce liver fibrosis. The DMN treatment regimen was 3 times each week (Mon, Wed, and Fri) with 10 mg/kg (i.e., 5.0 mg/mL of DMN at a dose of 2.0 mL/kg body weight) for first 3 weeks and half dose of 5 mg/kg (i.e., 5 mg/mL of DMN at a dose of 1.0 mL/kg) from day 22 to 57. The sham group animals were injected with PBS (solvent for DMN) using the same schedule. On day 22, 24 h post the last DMN treatment, blood samples were collected and assayed for liver disease biomarkers to confirm the effectiveness of the DMN treatment. DMN treated animals were assigned to different treatment groups based on body weight to ensure that the mean body weights and the range of body weights of the animals in each group have no significant difference. Animals from pretreatment group were sacrificed on day 25 to evaluate the disease progression stage prior to treatment begins. Treatments with formulations containing gp46 siRNA were started at day 25, with two treatments/week at specified siRNA dose for a total of 10 times. On day 59, 48 hours after last formulation treatment and 72 hours after last DMN treatment, animals were sacrificed by $CO_2$ inhalation. Liver lobes were excised and both gp46 and MRPL19 mRNA levels were determined by quantitative RT-PCR (TAQMAN®) assay. mRNA levels for gp46 were normalized to MRPL19 levels.

Figure 6:
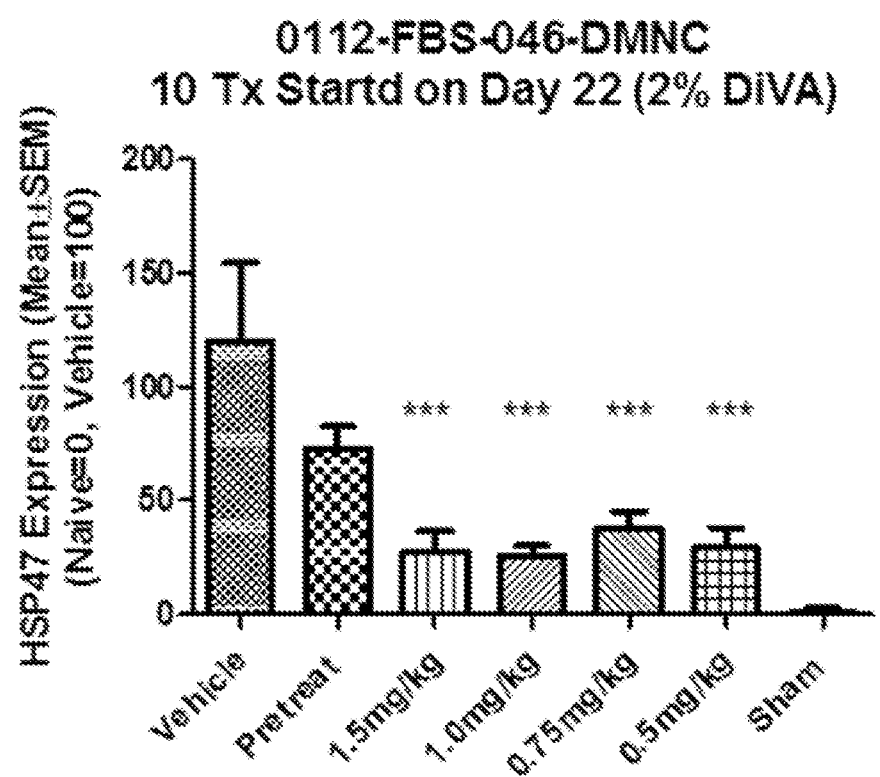
FIG. 6 shows the results of measurements in vivo using a rat DMNC model. After subtracting background gp46 mRNA levels determined from the naïve group, all test group values were normalized to the average gp46 mRNA of the vehicle group (expressed as a percent of the vehicle group). Mitochondrial ribosomal protein L19 (MRPL19) mRNA levels were determined by quantitative reverse transcriptase-polymerase chain reaction (RT-PCR) (TAQMAN®) assay. mRNA levels for gp46 were normalized to MRPL19 levels. (*** indicates p<0.02.)

Male Sprague-Dawley rats were treated with DMN at 10 mg/kg for three weeks (three times/week) and then 5 mg/kg from day 22 to 57 (three times/week) through intraperitoneal dosing to induce liver fibrosis. Animals (n=ten/group) were injected intravenously either with formulations consisting of HEDC:S104:DOPE:Chol:Peg-DMPE:DiVA (20:20:30:25:5:2) at 1.5, 1.0, 0.75, and 0.5 mg/kg siRNA or PBS (vehicle) for 10 times (2 times/week), one hour after the last injection of DMN. At day 59, total siRNA was purified from a section of the right liver lobe from each animal and stored at 4° C. until RNA analysis. Control groups included a PBS vehicle group (DMN-induced, PBS treated, n=7) and sham group (PBS treated in place of DMN and formulation, n=10) group. FIG. 6 shows the results of measurements. After subtracting background gp46 mRNA levels determined from the naïve group, all test group values were normalized to the average gp46 mRNA of the vehicle group (expressed as a percent of the vehicle group). Animal from pretreat group (n=7) were sacrificed on day 25 to evaluate disease progression level prior to treatment began. One-way Anova analysis followed by Dunnett's test showed significant gp46 gene knockdown in all treatment groups as compared to vehicle group (***, P<0.001).

The following table summarizes the compounds described herein, and the results obtained by testing these compounds in vivo and in vitro.

| Cationic Lipid Name | Structure | i. in vitro (pHSC) % KD —— ii. in vivo (rat DMNQ) % KD |
|---|---|---|
| Pr-HEDC | [structure] | i. 75% @ 50 nM |
| Pr-HE-DODC | [structure] | i. 73% @ 50 nM |
| HE-Et-DC | [structure] | i. 70% @ 50 nM |
| HE-Et-DODC | [structure] | i. 71% @ 50 nM |
| HE-Pr-DC | [structure] | i. 47% @ 50 nM |

| Cationic Lipid Name | Structure | i. in vitro (pHSC) % KD — ii. in vivo (rat DMNQ) % KD |
|---|---|---|
| HE-Pr-DODC | 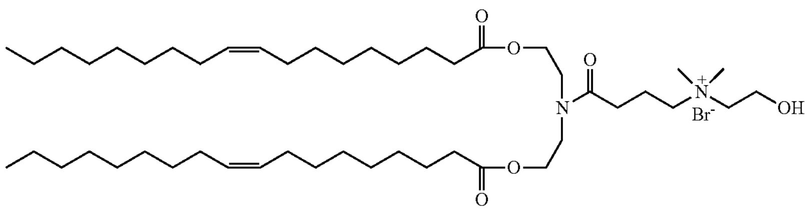 | i. 75% @ 50 nM |
| HE2-DODC | 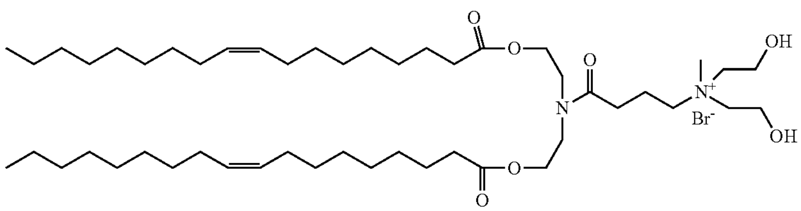 [SMILES: CCCCCCCC/C=C\CCCCCCCC(=O)OCCN(CCOC(=O)CCCCCCC/C=C\CCCCCCCC)C(=O)CCC[N+](C)(CCO)CCO ; [Br-]] | i. 78% @ 50 nM |
| HEDC-DLin | 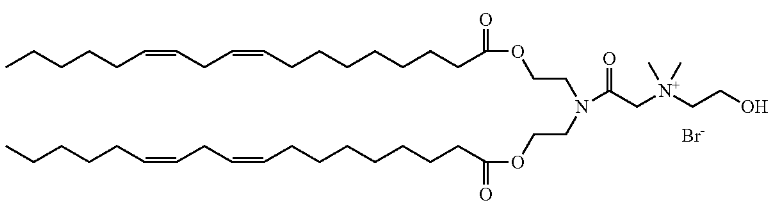 [SMILES: CCCCC/C=C\C/C=C\CCCCCCCC(=O)OCCN(CCOC(=O)CCCCCCC/C=C\C/C=C\CCCCC)C(=O)C[N+](C)(C)CCO ; [Br-]] | i. 50% @ 50 nM |
| HEDC | 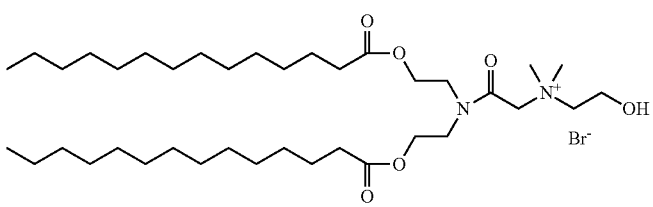 [SMILES: CCCCCCCCCCCCCC(=O)OCCN(CCOC(=O)CCCCCCCCCCCCC)C(=O)C[N+](C)(C)CCO ; [Br-]] | i. 68% @ 50 nM — ii. 52% @ 0.5 mpk |
| HEDC-12 | 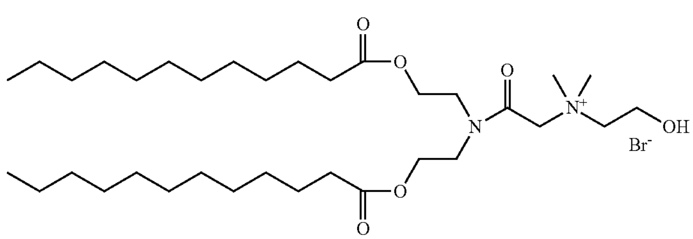 [SMILES: CCCCCCCCCCCC(=O)OCCN(CCOC(=O)CCCCCCCCCCC)C(=O)C[N+](C)(C)CCO ; [Br-]] | i. 0% @ 50 nM |
| HES104 | 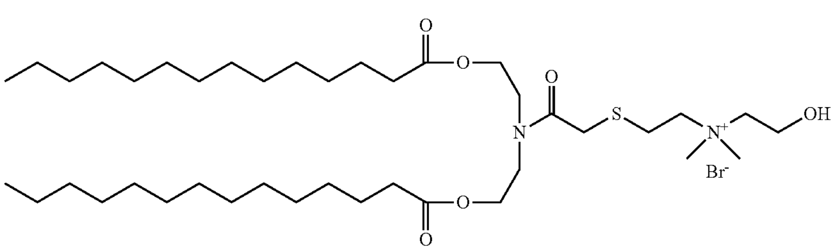 [SMILES: CCCCCCCCCCCCCC(=O)OCCN(CCOC(=O)CCCCCCCCCCCCC)C(=O)CSCC[N+](C)(C)CCO ; [Br-]] | |

| Cationic Lipid Name | Structure | i. in vitro (pHSC) % KD ii. in vivo (rat DMNQ) % KD |
|---|---|---|
| HES-104DO | 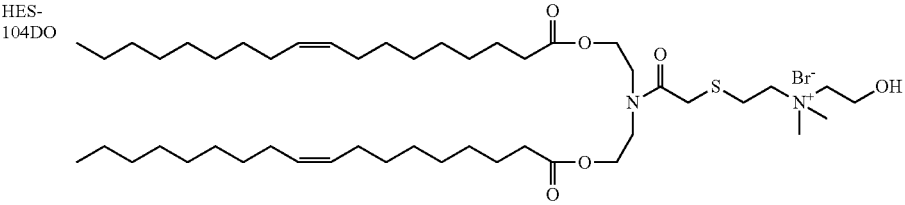 | |
| HETU-104DO | 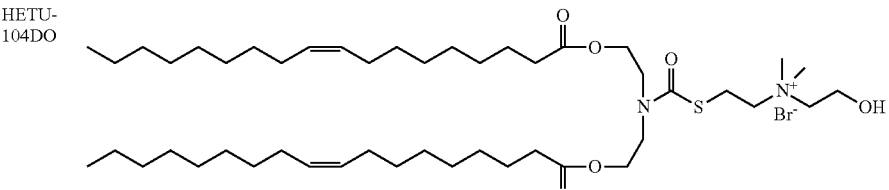 | |

Example 20: In Vivo Anti-Pulmonary-Fibrosis

Figure 7:
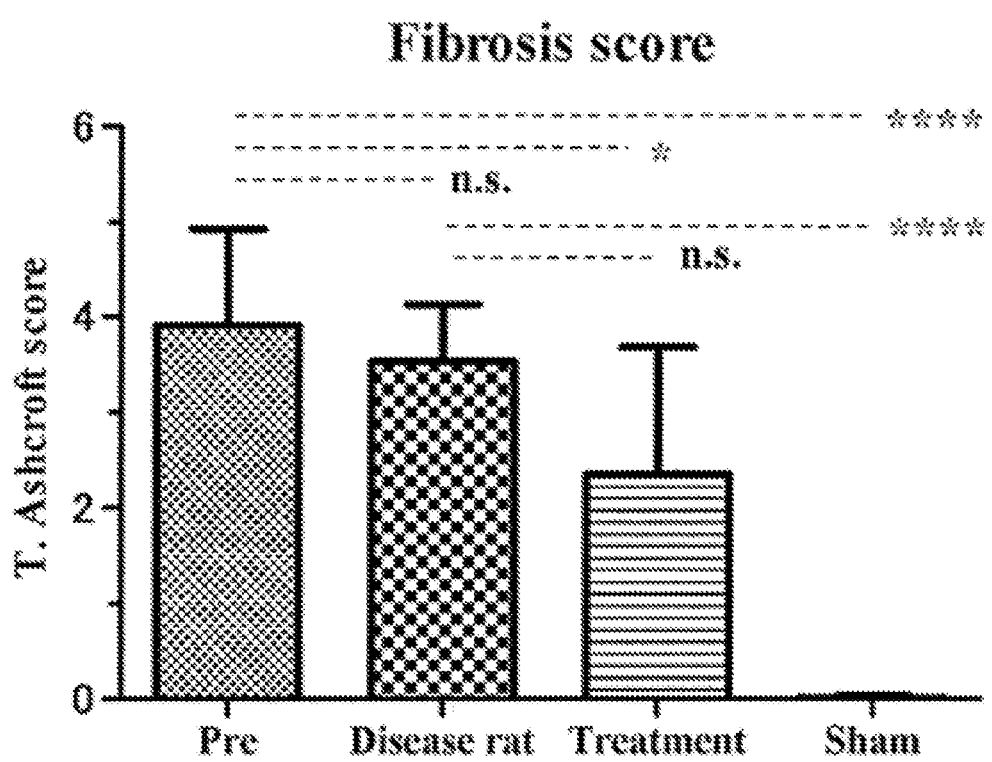
FIG. 7 shows the results of measurements in vivo using a rat pulmonary bleomycin model. The bar graph summarizes the fibrosis (T. Ashcroft) scoring of AZAN-stained lung sections for each group. Statistical analysis was performed using a One-way-ANOVA, Bonferroni multi comparison test with Prism5 software.

Male S-D rats (8 rats/group, 8 weeks old, Charles River Laboratories Japan, Inc.) were administered once with 0.45 mg bleomycin (BLM) dissolved in 0.1 mL of saline into the lung intratracheally cannulating (MicroSprayer, Penn-Century, Inc.) under anesthesia, to produce a bleomycin pulmonary fibrosis model. With this method, a significant fibrosis occurs in the lung generally after approximately 2 weeks. The liposome formulation (1.5 mg/kg as an amount of siRNA, 1 ml/kg in volume, i.e., 200 µl for a rat of 200 g) or PBS (1 ml/kg in volume) was administered to the rats via the tail vein, starting from the 2 weeks after the bleomycin administration, for total of ten times (every other day). The rats were sacrificed at two days post last treatment, histological investigation of the lung tissue was performed (see FIG. 7). One way ANOVA and Bonferroni multi comparison test was used to evaluate a statistically-significant difference.

A part of the removed lung was formalin-fixed in accordance with a routine method, and subjected to azan staining (azocarmine, aniline blue orange G solution).

As shown by the results of histological scoring (T. Ashcroft score) in FIG. 7, in the formulation administration group (Treatment), fibrosis score was significantly decreased.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

It will be readily apparent to one skilled in the art that varying substitutions and modifications can be made to the description disclosed herein without departing from the scope and spirit of the description. Thus, such additional embodiments are within the scope of the description herein and the following claims. The description herein teaches one skilled in the art to test various combinations and/or substitutions of chemical modifications described herein toward generating nucleic acid constructs with improved activity for mediating RNAi activity. Such improved activity can include improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying nucleic acid molecules with improved RNAi activity.

The descriptions illustratively described herein are suitably be practiced in the absence of any element or elements, limitation or limitations, not specifically disclosed herein. Thus, for example, the terms "a" and "an" and "the" and similar referents in the context of describing the description (especially in the context of the following claims) are to be construed to cover both the singular and the plural, unless otherwise indicated herein or clearly contradicted by context. The terms "comprising", "having," "including," "containing", etc. shall be read expansively and without limitation (e.g., meaning "including, but not limited to,"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the description and does not pose a limitation on the scope of the description unless otherwise claimed. No language in the specification should be construed as indicating any non-claimed element as essential to the practice of the description. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the description claimed. Thus, it should be understood that although the description herein has been specifically disclosed by preferred embodiments and optional features, modification and variation of the descriptions embodied therein herein disclosed are resorted to by those skilled in the art, and that such modifications and variations are considered to be within the scope of this description.

The description has been described broadly and generically herein. Each of the narrower species and subgeneric groupings falling within the generic disclosure also form part of the description. This includes the generic description of the description with a proviso or negative limitation removing any subject matter from the genus, regardless of whether or not the excised material is specifically recited herein. Other embodiments are within the following claims. In addition, where features or aspects of the description are described in terms of Markush groups, those skilled in the art will recognize that the description is also thereby described in terms of any individual member or subgroup of members of the Markush group.

What is claimed:

1. A composition comprising a compound of formula I,

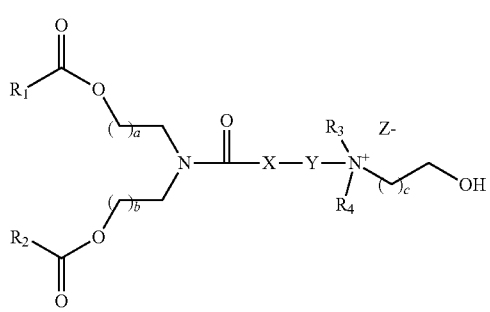

wherein
- $R_1$ and $R_2$ are independently selected from $C_{10}$ to $C_{30}$ alkyl, $C_{12}$ to $C_{30}$ alkenyl, and linoleoyl;
- $R_3$ and $R_4$ are independently selected from $C_1$ to $C_6$ alkyl and $C_2$ to $C_6$ alkanol;
- X is selected from —$CH_2$—, —S—, and —O—, or X is a bond;
- Y is selected from —$(CH_2)_n$—, —$S(CH_2)_n$—, —$O(CH_2)_n$—, -thiophene-, —$SO_2(CH_2)_n$—, and -ester-;
- n is 1, 2, 3 or 4;
- a is 1, 2, 3 or 4; b is 1, 2, 3 or 4; c is 1, 2, 3 or 4; and
- Z— is a counterion;

or an enantiomer, stereoisomer, or diastereoisomer thereof.

2. The composition of claim 1, wherein $R_1$ and $R_2$ are independently selected from $C_{10}$ to $C_{18}$ alkyl, and $C_{12}$ to $C_{18}$ alkenyl.

3. The composition of claim 1, wherein $R_3$ and $R_4$ are each independently $C_1$-$C_3$ alkyl.

4. The composition of claim 1, wherein $R_3$ and $R_4$ are each methyl or at least one of $R_3$ and $R_4$ is —$CH_2CH_2OH$.

5. The composition of claim 1, wherein a, b, and c are 1.

6. The composition of claim 1, wherein the composition further comprises a drug.

7. The composition of claim 6, wherein the drug directly or indirectly inhibits physicochemical actions of stellate cells involved in promotion of fibrosis.

8. The composition of claim 7, wherein the drug inhibits actions of stellate cells selected from the group consisting of transforming growth factor-beta (TGFβ) inhibitors, matrix metalloproteinase (MMP) production promotors, hepatocyte growth factors (HGF), angiotensin, tissue inhibitor of metalloproteinase (TIMP) production inhibitors, platelet-derived growth factor (PDGF), sodium channel inhibitor, apoptosis inhibitors, adiponectin, Rho kinase inhibitor, and heat shock protein 47 (HSP47).

9. The composition of claim 8, wherein the apoptosis inhibitor is herbal compound 861 (Cpd 861) or gliotoxin.

10. The composition of claim 7, wherein the drug controls the metabolism of an extracellular matrix.

11. The composition of claim 10, wherein the drug targets an extracellular matrix constituent molecule.

12. The composition of claim 11, wherein the extracellular matrix constituent molecule is collagen.

13. The composition of claim 7, wherein the drug comprises nucleic acid.

14. The composition of claim 13, wherein the nucleic acid is selected from the group consisting of oligonucleotides, siRNA, and DNA or RNA expression vectors.

15. The composition of claim 13, wherein the nucleic acid is formulated or complexed with polyethyleneimine (PEI) or PEI derivatives.

16. The composition of claim 15, wherein the PEI derivatives are selected from the group consisting of galactose PEI, cholesterol PEI, antibody derivatized PEI, and polyethylene glycol-PEI derivatives.

17. The composition of claim 1, wherein the composition is selected from the group consisting of a polymer micelle, a liposome, an emulsion, a microsphere, and a nano sphere.

18. The composition of claim 17, wherein the composition comprises a liposome comprising one or more lipid bilayers, wherein the lipid bilayers comprise the cationic lipid of formula 1.

19. The composition of claim 18, wherein the cationic lipid of formula I is at a concentration of 5 mol % to 50 mol % of the lipid bilayer.

20. The composition of claim 1, wherein the cationic lipid of formula I is selected from the group consisting of HEDC-12, HEDC, Pr-HEDC, HE-Et-DC, HE-Pr-DC, HES104, HE-DODC-DLin, HE2-DODC, HE-DODC, HE-Et-DODC, HE-Pr-DODC, HES104DO, and HETU104DO

HEDC-12

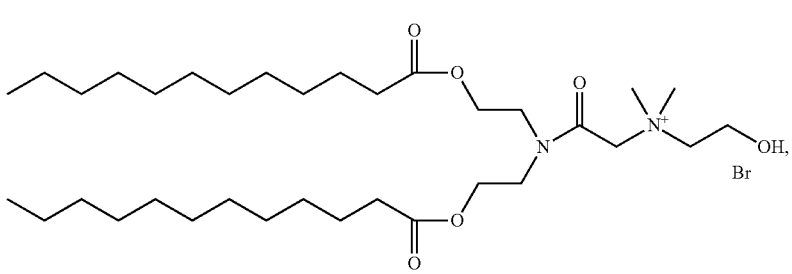

-continued
HEDC
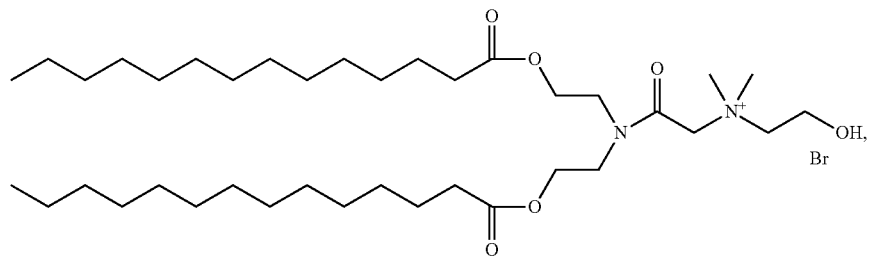
Pr-HEDC
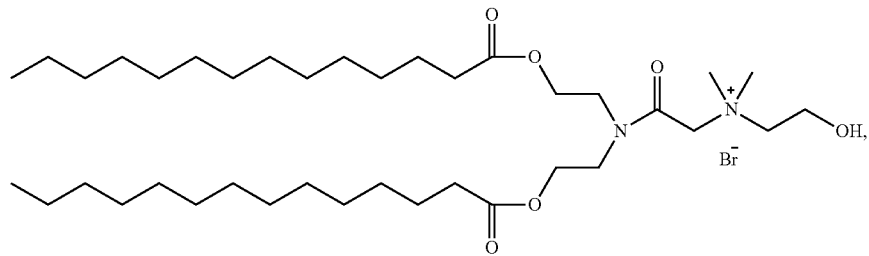
HE-Et-DC
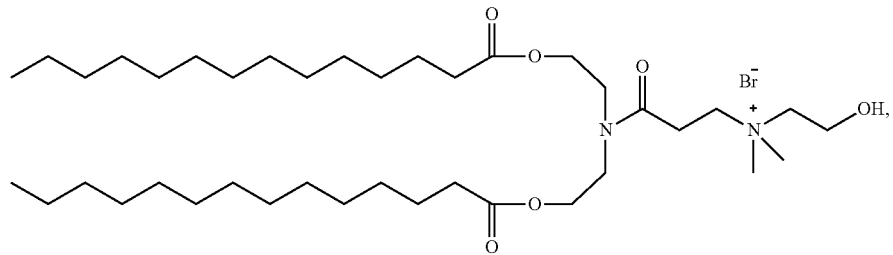
HE-Pr-DC
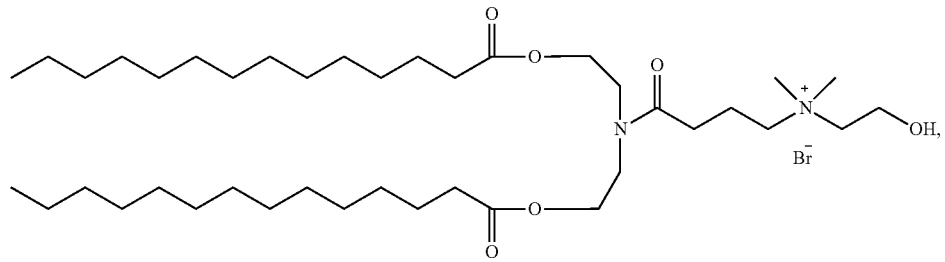
HES104
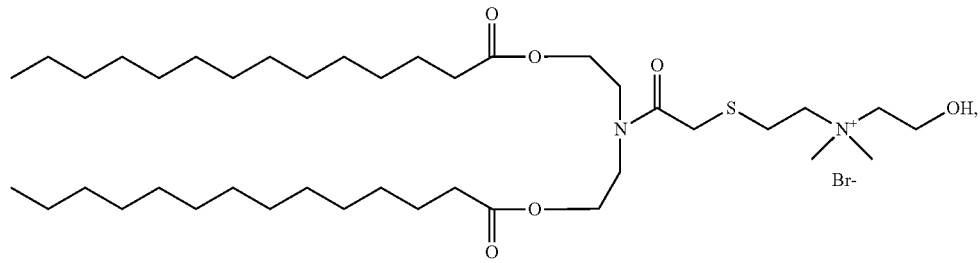
HE-DODC-DLin
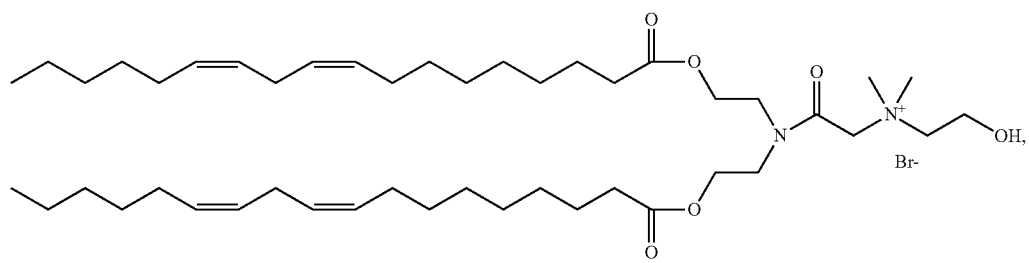

-continued
HE2-DODC
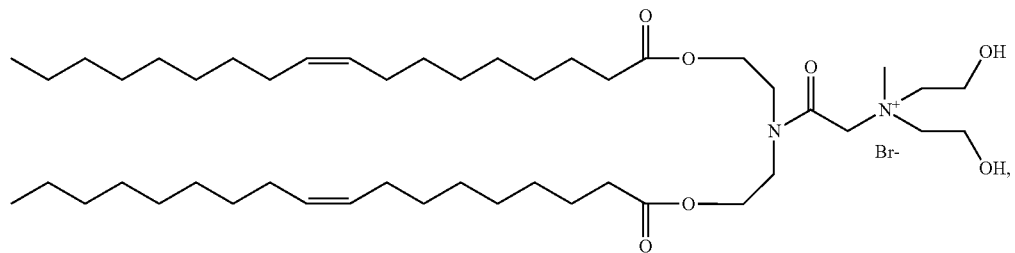
HE-DODC
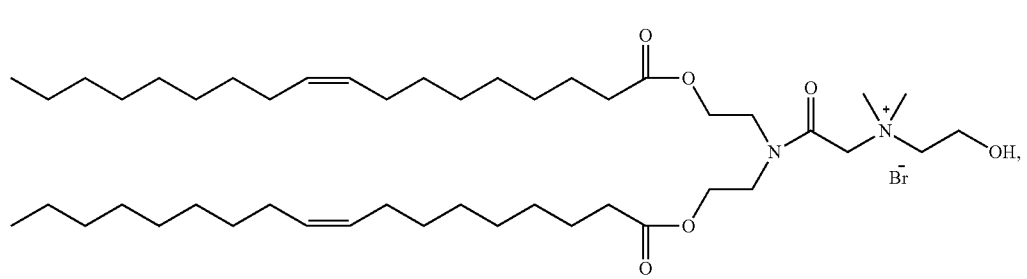
HE-Et-DODC
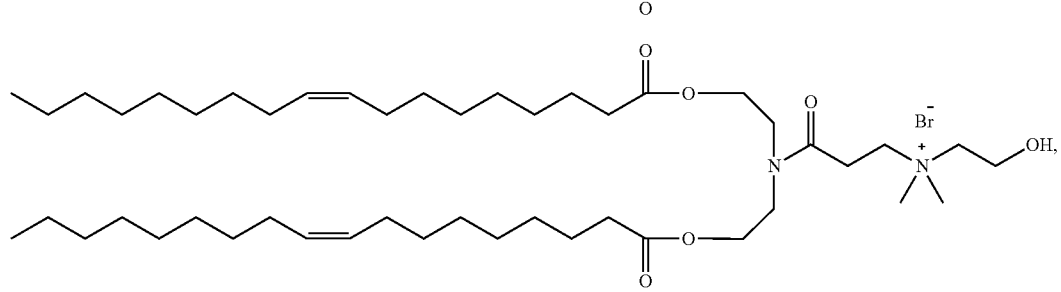
HE-Pr-DODC
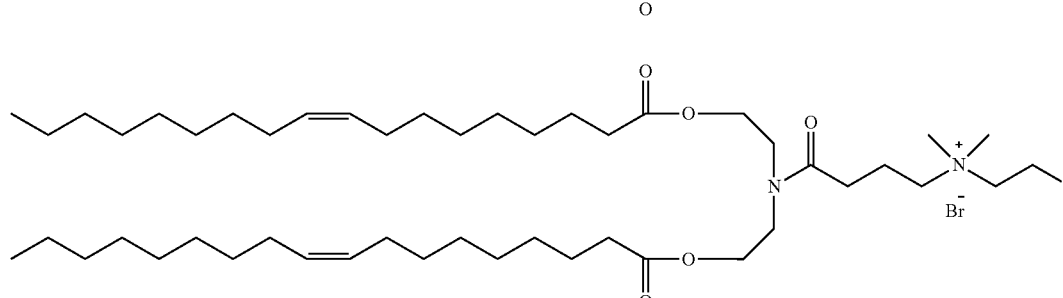
HES104DO
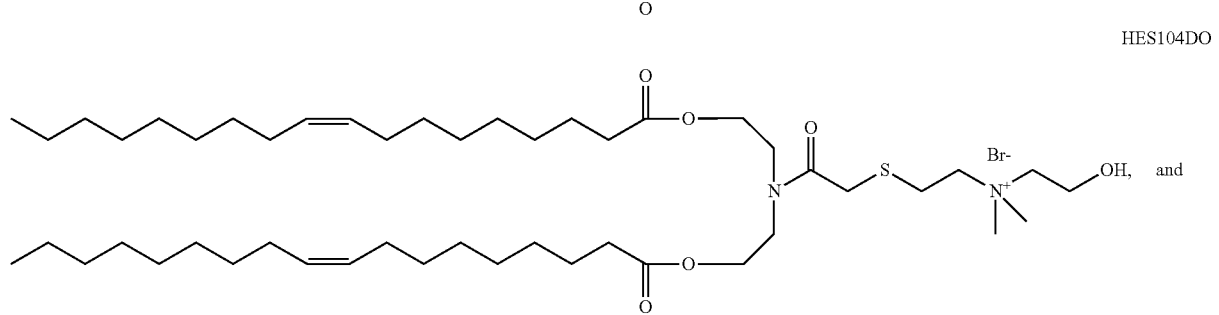
and
HETU104DO
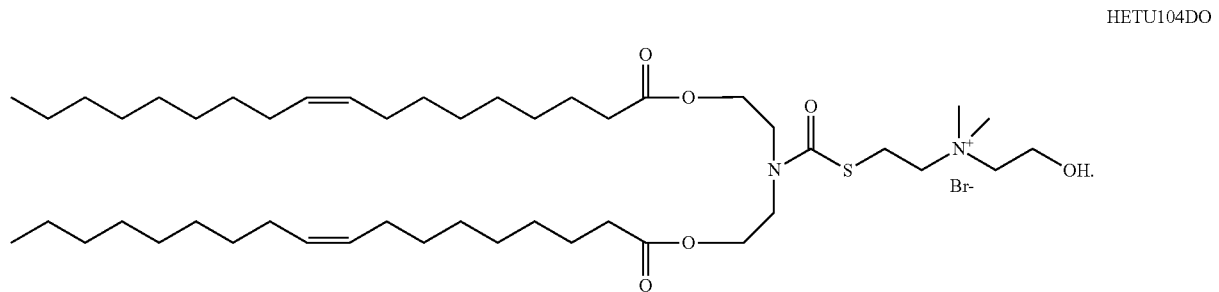

21. The composition of claim 20, wherein the cationic lipid is HEDC

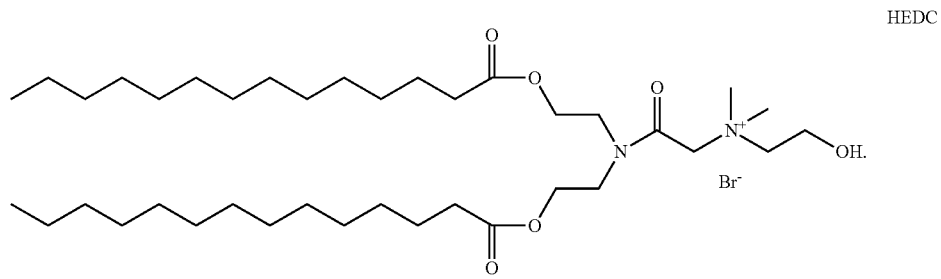 [SMILES: CCCCCCCCCCCCCC(=O)OCCN(CCOC(=O)CCCCCCCCCCCCC)C(=O)C[N+](C)(C)CCO ; [Br-]]

HEDC

22. The composition of claim 1, wherein the composition further comprises an ionizable cationic lipid.

23. The composition of claim 22, wherein the ionizable cationic lipid is S104

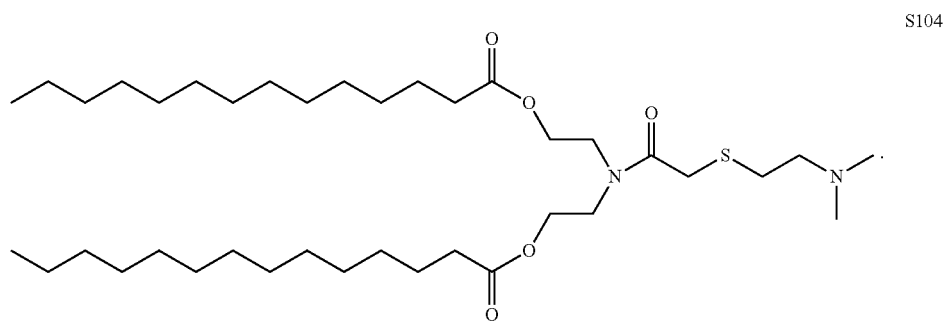 [SMILES: CCCCCCCCCCCCCC(=O)OCCN(CCOC(=O)CCCCCCCCCCCCC)C(=O)CSCCN(C)C]

S104

24. The composition of claim 22, wherein the ionizable cationic lipid is at a concentration of 5 to 45 mol % of the lipid bilayer.

25. The composition of claim 1, wherein composition further comprises a non-cationic lipid.

26. The composition of claim 25, wherein the non-cationic lipid is selected from the group consisting of lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof.

27. The composition of claim 25, wherein the non-cationic lipid is a sterol selected from the group consisting of cholesterol, cholestanol, cholestanone, cholestenone, coprostanol, cholesteryl-2'-hydroxyethyl ether, cholesteryl-4'-hydroxybutyl ether, and mixtures thereof.

28. A pharmaceutical formulation comprising the composition of claim 13 and a pharmaceutically acceptable excipient.

29. The pharmaceutical formulation of claim 28, wherein the pharmaceutically acceptable excipient is a preservative selected from the group consisting of sodium benzoate, ascorbic acid and esters of p-hydroxybenzoic acid.

30. The pharmaceutical formulation of claim 28, wherein the pharmaceutically acceptable excipient is selected from, alcohols, esters, sulfated aliphatic alcohols, sucrose, glucose, lactose, starch, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose; coconut oil, olive oil, sesame oil, peanut oil, soya, cellulose acetate phthalate, methyl acetate-methacrylate copolymer, and ester phthalates.

31. The pharmaceutical formulation of claim 28, wherein the pharmaceutical formulation is an aerosol suitable for human administration.

32. The pharmaceutical formulation of claim 31, further comprising excipients selected from the group consisting of dichlorodifluoromethane, trichlorofluoromethane, dichlorotetrafluoroethane, ethanol, emulsifiers, oleic acid, sorbitan trioleate, anti-oxidants, flavoring agents, and mixtures thereof.

33. The pharmaceutical formulation of claim 28, wherein the pharmaceutical formulation is suitable for parenteral administration.

34. The pharmaceutical formulation of claim 33, further comprising excipients selected from the group consisting of water, saline, sodium carboxymethyl cellulose, sorbitol, dextran, dextrose, mannitol, lactose, lecithin, albumin, sodium glutamate, cysteine hydrochloride, Hanks's solution, Ringer's solution, and physiological saline buffer.

35. The pharmaceutical formulation of claim 28, wherein the pharmaceutical formulation is suitable for administration to the central nervous system (CNS) or peripheral nervous system (PNS).

36. The pharmaceutical formulation of claim 35, suitable for intrathecal and intracerebroventricular administration, implantation of catheters and pumps, direct injection or perfusion at the site of injury or lesion, injection into the brain arterial system, or by chemical or osmotic opening of the blood-brain barrier.

37. The pharmaceutical formulation of claim 28, wherein the pharmaceutical formulation is suitable for intramuscular injection.

38. The pharmaceutical formulation of claim 37, further comprising excipients selected from polymeric or hydrophobic materials, and ion exchange resins.

39. The pharmaceutical formulation of claim 28, wherein the pharmaceutical formulation is suitable for administration via injection, subcutaneously, intraperitoneally, intravenously, intramuscularly, intradermally, intraorbitally, intracapsularly, intraspinally, or intrasternally, or infusion pump delivery.

40. The pharmaceutical formulation of claim 28, wherein the pharmaceutical formulation is suitable for administration locally by injection directly in the renal or cardiac area by depot implantation.

* * * * *

UNITED STATES PATENT AND TRADEMARK OFFICE
CERTIFICATE OF CORRECTION

PATENT NO. : 11,084,779 B2
APPLICATION NO. : 16/700304
DATED : August 10, 2021
INVENTOR(S) : Yoshiro Niitsu et al.

It is certified that error appears in the above-identified patent and that said Letters Patent is hereby corrected as shown below:

On the Title Page

In Column 2, item (57), Abstract, Line 4 (approx.), delete "is" and insert -- are --.

In the Drawings

In sheet 3 of 6, FIG. 3, Line 1, delete "model)" and insert -- (model) --.

In the Specification

Column 2, Line 21 (approx.), delete "--O--" and insert -- --O--, --.

Column 2, Line 60 (approx.), delete "formula I" and insert -- formula 1 --.

Column 7, Line 48, delete "palmitoyloleyol" and insert -- palmitoyloleoyl --.

Column 9, Lines 45-46, delete "background gp46 mRNA" and insert -- background heat-shock glycoprotein 46 (gp46) mRNA --.

Column 9, Line 53, delete "MRPL19" and insert -- Mitochondrial ribosomal protein L19 (MRPL19) --.

Column 10, Line 15 (approx.), delete "is" and insert -- are --.

Column 10, Line 21 (approx.), delete "--O--" and insert -- --O--, --.

Column 19, Line 43, delete "quatemary" and insert -- quaternary --.

Column 19, Line 47, delete "quatemary" and insert -- quaternary --.

Signed and Sealed this
Thirty-first Day of January, 2023

Katherine Kelly Vidal
*Director of the United States Patent and Trademark Office*

CERTIFICATE OF CORRECTION (continued)
U.S. Pat. No. 11,084,779 B2

Column 20, Line 6, delete "PEG-cholesterol." and insert -- PEG-cholesterol, --.

Column 26, Line 48, delete "polyvinylpyrolidone" and insert -- polyvinylpyrrolidone --.

Column 27, Line 11 (approx.), delete "DMPE)" and insert -- DMPE), --.

Column 27, Line 37, delete "palmitoyloleyol" and insert -- palmitoyloleoyl --.

Column 28, Line 48, delete "acitretine" and insert -- acitretin --.

Column 29, Line 10, delete "2.0." and insert -- 2.0, --.

Column 34, Lines 22-23, delete "methylacetate" and insert -- methyl acetate --.

Column 35, Line 61 (approx.), delete "9 L" and insert -- 9L --.

Column 37, Line 8, delete "(See," and insert -- See, --.

Column 39, Line 4, delete "oxoethan-aminium" and insert -- oxoethanaminium --.

Column 39, Line 55 (approx.), delete "in DCM" and insert -- in dichloromethane (DCM) --.

Column 41, Lines 35-41 (approx.), delete "N,N-dimethylglycine (56.6 g, 548 mmol), 1-hydroxybenzotriazole (HOBt) hydrate (83.9 g, 548 mmol) and N-(3-dimethylaminopropyl)-N'-ethylcarbodiimide hydrochloride (EDC) (105 g, 548 mmol) were added to dimethylformamide (DMF) (3.5 L), and the mixture was stirred at ambient temperature for one hour. A clear solution was formed. HEDC-amine-IN TFA salt (270 g, 442 mmol) was mixed with DCM (1.15 L) and 6% NaHCO3 (1.15 L)." and insert -- N,N-Dimethylglycine (56.6 g, 548 mmol), hydroxybenzotriazole (HOBt) hydrate (83.9 g, 548 mmol) and 1-ethyl-3-(3-dimethylaminopropyl)carbodiimide (EDC) hydrochloride (105 g, 548 mmol) were added to dimethyhlformamide (DMF) (3.5 L), and the mixture was stirred at ambient temperature for a period of one hour. A clear solution was formed. HEDC-amine-IN TFA salt (270 g, 442 mmol) was mixed with DCM (1.15 L) and 6% NaHCO3 (1.15 L). --.

Column 42, Line 40, delete "63p" and insert -- 63µ --.

Column 43, Lines 16-17, delete "dimethylglycin-intermediate" and insert -- dimethylglycine-intermediate --.

Column 43, Line 18, delete "dimethylglycin intermediate" and insert -- dimethylglycine-intermediate --.

Column 47, Lines 40-41, delete "hexaflourophosphat" and insert -- hexaflourophosphate --.

Column 53, Line 16, delete "an d" and insert -- and --.

Column 53, Line 27 (approx.), delete "oxopro-pan" and insert -- oxopropan --.

CERTIFICATE OF CORRECTION (continued)
U.S. Pat. No. 11,084,779 B2

Column 59, Line 1, delete "diethanolamine)" and insert -- diethanolamine --.

Column 60, Line 53 (approx.), delete "(((Z)" and insert -- (Z) --.

Column 63, Line 1, delete "(((Z)" and insert -- (Z) --.

Column 71, Line 4, delete "Bromoacetyl" and insert -- A bromoacetyl --.

Column 73, Line 52, delete "(S104)" and insert -- (S104). --.

Column 77, Line 59, delete "with 10% $K_2CO_3$ (30 mL) at 0-5° C." and insert -- with 10% potassium carbonate ($K_2CO_3$) (30 mL) at 0-5° C. --.

Column 78, Line 62, delete "phosphate buffered" and insert -- phosphate-buffered --.

Column 83, Line 66, delete "~100,000 MW cut-off" and insert -- ~100,000 molecular weight cutoff (MWCO) --.

Column 83, Line 67, delete "Midgee" and insert -- Midgee™ --.

Column 84, Line 10, delete "ethanol" and insert -- ethanol (EtOH) --.

Column 84, Line 57 (approx.), delete "%. Solution" and insert -- %. The solution --.

Column 85, Line 62, delete "VIIA 7®" and insert -- VIIA® 7 --.

Column 86, Line 6, delete "IACUC" and insert -- Institutional Animal Care and Use Committee IACUC --.

Column 86, Lines 10-11, delete "Up-regulation of heat shock protein 47 (HSP47) was induced via intraperitoneal injecting $CCl_4$" and insert -- Up-regulation of HSP47 was induced via intraperitoneal injection of carbon tetrachloride ($CCl_4$) --.

Column 86, Line 33, delete "RNA later" and insert -- RNALATER® --.

Column 86, Line 50, delete "VIIA 7® realtime" and insert -- VIIA® 7 real-time --.

Column 87, Line 6 (approx.), delete "con jugate" and insert -- conjugate --.

Column 87, Line 20, delete "con jugate" and insert -- conjugate --.

Column 87, Line 37 (approx.), delete "con jugate" and insert -- conjugate --.

Column 88, Line 16, delete "Graphpad" and insert -- Graphad --.

Column 88, Lines 21-24 (approx.), delete "was cultured in MEM/EBSS (Hyclone, Logan, Utah, Cat

CERTIFICATE OF CORRECTION (continued)
U.S. Pat. No. 11,084,779 B2

SH30024.01) supplemented with 10% FBS (Hyclone, Logan, Utah Cat #SH30910). HepG2 cells were seeded in 96-well Optilux black plates (BD" and insert -- was cultured in minimal essential medium with Earle's balanced salts (MEM/EBSS) (HYCLONE™, Logan, Utah, Cat# SH30024.01) supplemented with 10% fetal bovine serum (FBS) (HYCLONE™, Logan, Utah Cat# SH30910). HepG2 cells were seeded in 96-well OPTILUX™ black plates (BD --.

Column 88, Lines 27-29, delete "At 48 h post formulation addition, cell viability was determined using CellTiter-Glo Luminescent Cell Viability Assay Kit" and insert -- At 48 hours post formulation addition, cell viability was determined using CELL TITER-GLO® Luminescent Cell Viability Assay Kit --.

Column 88, Line 31, delete "Clarity" and insert -- Clarity™ --.

Column 88, Lines 34-35, delete "formulation treated well normalized against mock treated wells." and insert -- formulation-treated, well-normalized against mock-treated wells. --.

Column 88, Line 36, delete "quatemary" and insert -- quaternary --.

Column 92, Line 43, delete "h post" and insert -- hours post --.

Column 92, Line 53, delete "at" and insert -- at a --.

Column 97, Line 48, delete "azan" and insert -- AZAN --.

Column 98, Lines 47-48, delete "containing"" and insert -- "containing" --.

In the Claims

Column 103, Line 37, Claim 1, delete "-ester-" and insert -- --ester-- --.

Column 104, Line 20 (approx.), Claim 9, delete "8" and insert -- 7 --.

Column 104, Line 42 (approx.), Claim 17, delete "nano sphere" and insert -- nanosphere --.

Column 109, Line 55 (approx.), Claim 26, delete "palmitoyloleyol-phosphatidylglycerol" and insert -- palmitoyloleoyl-phosphatidylglycerol --.

SEQUENCE LISTING

```
<160> NUMBER OF SEQ ID NOS: 5

<210> SEQ ID NO 1
<211> LENGTH: 2208
<212> TYPE: RNA
<213> ORGANISM: Homo sapiens

<400> SEQUENCE: 1
ucuuuggcuu uuuuuggcgg agcuggggcg cccuccggaa gcguuuccaa cuuuccagaa      60
guuucucggg acgggcagga gggggugggg acugccauau auagaucccg ggagcagggg     120
agcgggcuaa gaguagaauc gugucgcggc ucgagagcga gagucacguc ccggcgcuag     180
cccagcccga cccaggccca ccguggugca cgcaaaccac uuccuggcca ugcgcucccu     240
ccugcuucuc agcgccuucu gccuccugga ggcggcccug gccgccgagg ugaagaaacc     300
ugcagccgca gcagcuccug gcacugcgga gaaguugagc cccaaggcgg ccacgcuugc     360
cgagcgcagc gccggccugg ccuucagcuu guaccaggcc auggccaagg accaggcagu     420
ggagaacauc cuggugucac ccguggugu ggccucgucg cuagggcucg ugucgcuggg     480
cggcaaggcg accacggcgu cgcaggccaa ggcagugcug agcgccgagc agcugcgcga     540
cgaggaggug cacgccggcc ugggcgagcu gcugcgcuca cucagcaacu ccacggcgcg     600
caacgugacc uggaagcugg gcagccgacu guacggaccc agcucaguga gcuucgcuga     660
ugacuucgug cgcagcagca agcagcacua caacugcgag cacuccaaga ucaacuuccg     720
cgacaagcgc agcgcgcugc aguccaucaa cgagugggcc gcgcagacca ccgacggcaa     780
gcugcccgag gucaccaagg acguggagcg cacggacggc gcccugcuag ucaacgccau     840
guucuucaag ccacacuggg augagaaauu ccaccacaag augguggaca accguggcuu     900
cauggugacu cgguccuaua ccgugggugu caugaugaug caccggacag gcucucacaa     960
cuacuacgac gacgagaagg aaaagcugca aaucguggag augccccugg cccacaagcu    1020
cuccagccuc aucauccuca ugccccauca cguggagccu cucgagcgcc uugaaaagcu    1080
gcuaaccaaa gagcagcuga agaucuggau ggggaagaug cagaagaagg cuguugccau    1140
cuccuugccc aagggugugg uggaggugac ccaugaccug cagaaacacc uggcugggcu    1200
gggccugacu gaggccauug acaagaacaa ggccgacuug ucacgcaugu caggcaagaa    1260
ggaccuguac cuggccagcg uguuccacgc caccgccuuu gaguuggaca cagauggcaa    1320
ccccuuugac caggacaucu acgggcgcga ggagcugcgc agcccaagc uguucuacgc    1380 cgaccacccc uucaucuucc uagugcggga cacccaaagc ggcucccugc uauucauugg    1440
gcgccugguc cggccuaagg gugacaagau gcgagacgag uuauagggcc ucagggugca    1500
cacaggaugg caggaggcau ccaaaggcuc cugagacaca ugggugcuau uggggguuggg    1560 ggggagguga gguaccagcc uuggauacuc caugggggug ggguggaaaa acagaccggg    1620
guucccgugu gccugagcgg accuucccag cuagaauuca cuccacuugg acaugggccc    1680
```

```
cagauaccau gaugcugagc ccggaaacuc cacauccugu gggaccuggg ccauagucau    1740
ucugccugcc cugaaagucc cagaucaagc cugccucaau caguauucau auuuauagcc    1800
agguaccuuc ucaccuguga gaccaaauug agcuaggggg gucagccagc ccucuucuga    1860
cacuaaaaca ccucagcugc cuccccagcu cuaucccaac cucucccaac uauaaaacua    1920
ggugcugcag ccccugggac caggcacccc cagaaugacc uggccgcagu gaggcggauu    1980
gagaaggagc ucccaggagg ggcuucuggg cagacucugg ucaagaagca ucgugucugg    2040
cguugugggg augaacuuuu uguuuuguuu cuuccuuuuu uaguucuuca aagauaggga    2100 gggaagggg  aacaugagcc uuuguugcua ucaauccaag aacuuauuug ucauuuuuu    2160 uuuucaauaa aacuuuucca augacauuuu guuggagcgu ggaaaaaa                2208

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
ggacaggccu cuacaacuat t                                               21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
uaguuguaga ggccugucct t                                               21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
ggacaggccu guacaacuat t                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 5
uaguuguaca ggccugucct t                                            21
```